(12) United States Patent
Doohan et al.

(10) Patent No.: US 11,111,501 B2
(45) Date of Patent: Sep. 7, 2021

(54) FUSARIUM HEAD BLIGHT DISEASE RESISTANCE

(71) Applicants: UNIVERSITY COLLEGE DUBLIN, NATIONAL UNIVERSITY OF IRELAND, DUBLIN, Dublin (IE); Agriculture and Food Development Authority (TEAGASC), Carlow (IE)

(72) Inventors: Fiona Doohan, Donegal (IE); Ganesh Thapa, Jorhat Assam (IN); Lokandha Rao Gunupuru, Andhra (IN); Gerard Hehir, Carlow (IE); Ewen Mullins, Carlow (IE)

(73) Assignee: UNIVERSITY COLLEGE DUBLIN, NATIONAL UNIVERSITY OF IRELAND, DUBLIN;AGRICULTURE AND FOOD DEVELOPMENT AUTHORITY ("TEAGASC")

( * ) Notice: Subject to any disclaimer, the term of this patent is extended or adjusted under 35 U.S.C. 154(b) by 0 days.

(21) Appl. No.: 16/492,679

(22) PCT Filed: Mar. 9, 2018

(86) PCT No.: PCT/EP2018/055978
§ 371 (c)(1),
(2) Date: Nov. 19, 2019

(87) PCT Pub. No.: WO2018/162750
PCT Pub. Date: Sep. 13, 2018

(65) Prior Publication Data
US 2021/0054400 A1    Feb. 25, 2021

(30) Foreign Application Priority Data
Mar. 10, 2017    (EP) .................................. 17160440

(51) Int. Cl.
*C12N 15/82* (2006.01)
*C12N 9/12* (2006.01)

(52) U.S. Cl.
CPC ........... *C12N 15/8282* (2013.01); *C12N 9/12* (2013.01)

(58) Field of Classification Search
None
See application file for complete search history.

(56) References Cited

U.S. PATENT DOCUMENTS 6,197,518 B1 *  3/2001  Procunier ............ C12Q 1/6895
                                                          435/6.12

FOREIGN PATENT DOCUMENTS

| CN | 102586291 A | 7/2012 |
| WO | 2015184331 A2 | 12/2015 |
| WO | 2016008942 A1 | 1/2016 |

OTHER PUBLICATIONS

Buestmayretal. Theor. Appl. Genet. (1999), vol. 98, pp. 76-85.*
Thapa et al. Frontiers in Plant Science (2018), 9 (687):1-15.*
International Search Report for PCT/EP2018/055978.

* cited by examiner

*Primary Examiner* — Medina A Ibrahim
(74) *Attorney, Agent, or Firm* — Cotman IP Law Group

(57) ABSTRACT

A recombinant construct comprising a nucleotide sequence of SEQUENCE ID NO. 1 or a functional variant or functional fragment thereof is provided. Also provided are plant cells transformed with the gene and plant material, including plant cell cultures, seeds and plants, comprising the transformed plant cells.

15 Claims, 14 Drawing Sheets
Specification includes a Sequence Listing.

Figure 4

AKA-Akashinriki, BUF:FES buffer, BSMV:VIGS control vector, FC: *Fusarium coulmorum*, LRR-1, LRR-2 are two different constructs used to silence the *HvLRRK* gene.

FUSARIUM HEAD BLIGHT DISEASE RESISTANCE

CROSS-REFERENCE TO RELATED APPLICATIONS

The present application is a U.S. National Stage of PCT Patent Application Ser. No. PCT/EP2018/055978, filed on Mar. 9, 2018, specification of which is herein incorporated by reference for completeness of disclosure.

FIELD OF THE INVENTION

The current invention relates to resistance to *Fusarium* head blight disease. In particular, the invention relates to a gene contributing to resistance to *Fusarium* head blight disease and a recombinant construct including said gene. The invention also relates to plant cells transformed with the gene and plant material, including plant cell cultures, seeds and plants, comprising the transformed plant cells.

BACKGROUND OF THE INVENTION

*Fusarium* head blight (FHB) is a fungal disease in plants, in particular, in cereals such as wheat, barley and oats. It is caused by a *Fusarium* fungus, with the species *Fusarium graminearum* is the predominant causal agent of the disease in most areas of the world. In wheat, the fungus infects the head of the plant and causes the kernels to shrivel up. It can also produce a mycotoxin that further reduces the quality of kernel. These toxins can also be harmful to both animals and humans.

FHB in wheat is an economic presage and its post-harvest grain loss and considerable health risk to animals and humans due to accumulation of mycotoxin deoxynivalenol (DON), are well known. Given the economic concern of FHB, several control strategies have been developed to avert FHB epidemics. These include resistance cultivars and systems for the control of FHB and both chemical and biological control.

The use of host resistance is considered to be an efficacious means to control FHB in wheat and several approaches have been described previously. Breeding and selection of crossed lines for durable resistance to disease and yield stability take time and lines behave differently in different environments. There is also the chance of resistance breakdown in lines developed with this approach.

EBI accession no. EMBL: HP612298 describes a sequence from *Triticum aestivum* cultivar Bobwhite. EBI accession no. UNIPROT: W5GU67 describes an uncharacterised protein sequence from Chinese Spring Wheat. EBI accession no. EMBL: GU084176 describes *Triticum aestivum* LRR receptor-like kinase mRNA sequence. This gene is a LRR receptor-like kinase gene. It is responsive to stress and stripe rust disease development. EBI accession no. describes *Triticum aestivum* LRR receptor like kinase sequence. This gene is a LRR receptor-like kinase gene. These publications do not disclose recombinant constructs and are not concerned with FHB resistance. Furthermore, none of the sequences disclosed are equivalent to the sequence of SEQUENCE ID NO. 1 of the current invention nor are they functional variants or functional fragments thereof as defined herein.

CN102586291 discloses a sequence encoding LRR receptor kinase from Chinese wheat cv. Wangshuibai. This sequence is not equivalent to the sequence of SEQUENCE ID NO. 1 of the current invention nor is it a functional variant or functional fragment.

WO2015/184331 discloses a sequence encoding an LRR receptor kinase, present within the fhb1 QTL located in 3B chromosome. This sequence is not equivalent to the sequence of SEQUENCE ID NO. 1 of the current invention nor is it a functional variant or functional fragment.

WO2016008942 discloses a sequence located in wheat chromosome 4A. It is not an LRR receptor like kinase gene nor is it at all related to FHB resistance. This sequence is not equivalent to the sequence of SEQUENCE ID NO. 1 of the current invention nor is it a functional variant or functional fragment.

It is an object of the current invention to provide a gene which provides FHB resistance in plants. No such kinase has been described to date for this disease.

BRIEF SUMMARY OF THE INVENTION

A first aspect of the invention provides a recombinant construct comprising (or consisting of) a nucleotide sequence of SEQUENCE ID NO. 1 or a functional variant or functional fragment thereof.

Preferably, the functional variant has at least 30% sequence identity with SEQUENCE ID NO. 1.

Preferably, the functional variant has at least 70% sequence identity with SEQUENCE ID NO. 1.

Preferably, the functional variant has at least 90% sequence identity with SEQUENCE ID NO. 1.

A recombinant host cell comprising a construct of the invention and as described herein is also provided by a further aspect of the invention.

The invention also provides a transformation platform comprising a recombinant construct of the invention.

The invention also provides plant material genetically transformed or modified with a nucleotide, recombinant construct or transformation platform of the invention. Typically, the plant material comprises a plant cell carrying a transgene, in which the transgene comprises (or consists of) a nucleotide sequence of SEQUENCE ID NO. 1 or a functional variant or a functional fragment thereof.

The invention also provides a method of genetically transforming a plant material comprising the steps of transforming a cell or cells of the plant material with a nucleotide, recombinant construct or transformation platform of the invention.

Preferably, the transformed cell (or cells) is capable of overexpression of the nucleotide sequence of SEQUENCE ID NO. 1 or a functional variant thereof. The invention also provides a method of producing a transgenic plant or plant material comprising the steps of genetically transforming a plant or plant material according to a method of the invention.

Preferably, the transgenic plant or plant material is resistant to FHB or has enhanced resistance to FHB compared to non-modified or non-transgenic plants.

Typically, the plant material is selected from the group comprising a plant cell, plant cell culture, plant tissue, plant or seed for a plant.

Preferably, the plant is a cereal. Typically, said cereal is selected from the group comprising maize, rice, wheat, barley, sorghum, millet, oats, soybean and rye. Preferably, the cereal is wheat.

A further aspect of the invention provides an isolated nucleotide sequence comprising (or consisting of) SEQUENCE ID NO. 1 or a functional variant thereof or functional fragment thereof.

Preferably, the functional variant has at least 55% sequence identity with SEQUENCE ID NO. 1.

Preferably, the functional variant has at least 70% sequence identity with SEQUENCE ID NO. 1.

Preferably, the functional variant has at least 90% sequence identity with SEQUENCE ID NO. 1.

A further aspect of the invention provides an isolated peptide comprising (or consisting of) SEQUENCE ID NO. 2 or a functional variant thereof or a functional fragment thereof.

The invention also provides an isolated protein encoded by the nucleotide of the invention or having a sequence of SEQUENCE ID NO. 2 or a functional variant thereof or a functional fragment thereof.

Preferably, the functional variant has at least 70% sequence identity with SEQUENCE ID NO. 2.

The isolated nucleotide or peptide is for enhancing or providing FHB resistance in plants or plant material.

Definitions

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

In the specification, the terms "comprise, comprises, comprised and comprising" or any variation thereof and the terms "include, includes, included and including" or any variation thereof are considered to be totally interchangeable and they should all be afforded the widest possible interpretation and vice versa.

"TaLRRK-6D" when used here in means a gene that is capable of enhancing or providing resistance to FHB in plants. It is a transmembrane kinase protein belonging to the LRR-RLK family. It has a nucleotide sequence of 3096 nucleotides in length and an amino acid sequence of 1031 amino acids in length and has a signal peptide, leucine rich repeats (LLR) domain, a transmembrane domain and a kinase domain. It has a nucleotide sequence of SEQ ID NO. 1 or a variant thereof.

"FHB resistance" as defined herein is the reduction of FHB growth on or in the plant. FHB resistance may be measured by a decrease, or an absence, of FHB symptoms in plants. This may be determined by the method of Example 2.

The phrase "FHB symptoms" when used herein refers to an effect of infection with FHB and includes, but is not limited to, one or more of damage of spikelets, premature discolouration and/or bleaching of spikelets, deoxynivalenol mycotoxin contamination of grain, and shriveling and/or wrinkling of kernels. Methods of analysing the phenotypic effects are known in the art.

As used herein the term "variant thereof" should be understood to mean a sequence which is substantially identical to a given sequence, but which is altered in respect of one or more amino acid residues or nucleotide residues compared to the given sequence, in such a way so as not to significantly alter the claimed function. Typically, the variant is a (nucleotide or amino acid) sequence having from about 30% to about 99% sequence identity with a given sequence. Generally, the variant is a (nucleotide or amino acid) sequence having from about 70% to about 99% sequence identity, preferably 70, 75, 80, 85, 86, 88, 87, 89, 90, 91, 92, 93, 94, 95, 96, 97, 98 or 99%, sequence identity with a given sequence and which is typically capable of enhancing or providing resistance to FHB in plants, i.e. variant is a functional variant. Such alterations include, insertion, addition, deletion and/or substitution of an amino acid residue(s), or a nucleotide residue(s). There may be 1, 2, 3, 4, or 5 alterations. It will be appreciated that such variants may be naturally occurring variants or may be a non-natural variant. The term variant also includes a fragment of a sequence. In relation to a variant of a peptide, the insertion, addition and substitution with natural and modified amino acids are envisaged. The variant may have conservative amino acid changes, wherein the amino acid being introduced is similar structurally, chemically, or functionally to that being substituted.

The term "functional variant" when used herein is taken to mean a variant of SEQUENCE ID NO. 1 or SEQUENCE ID NO. 2, which is capable of enhancing or providing resistance to FHB in plants.

The term "fragment" means a segment of a given sequence. Typically, the fragment has from about 10 to 1000 contiguous amino acids, preferably about 50, 100, 200, 300, 400, 500, 600, 700, 800, or 900 amino acids. Typically, the fragment has from 10 to 3000 contiguous nucleotides preferably about 100, 250, 500, 750, 1000, 1250, 1500, 1750, 2000, 2250, 2500 or 2750 nucleotides. The fragment is a functional fragment, i.e., it is a segment of SEQUENCE ID NO. 1 or SEQUENCE ID NO. 2 which is capable of enhancing or providing resistance to FHB in plants. Functional fragments of functional variants of the invention are also provided.

In terms of "sequence homology", the term should be understood to mean that a variant (or homolog) which shares a defined percent similarity or identity with a reference sequence when the percentage of aligned residues of the variant (or homolog) are either identical to, or conservative substitutions of, the corresponding residues in the reference sequence and where the variant (or homolog) shares the same function as the reference sequence.

In this specification, "homology", "identity" or "similarity" refers to the relationship between two peptides or two nucleotide sequences based on an alignment of the sequences. The term "identity" when used herein means the percentage of identical, or conservative substitutions of, amino acid or nucleotide residues at corresponding positions in two sequences when the sequences are aligned and is across the entire length of the sequence, i.e. a variant (or homolog) that shares 70% sequence identity with a reference sequence is one in which any 70% of aligned residues of the variant (or homolog) are identical to, or conservative substitutions of, the corresponding residues in the reference sequence across the entire length of the sequence. For sequence comparison, one sequence acts as a reference sequence, to which test sequences are compared.

This alignment and the percent homology, similarity or sequence identity can be determined using software programs known in the art, for example, BLAST, EMBOSS Needle or Clustal Omega, using default parameters. Details of these programs can be found at the following Internet address: www.ncbi.nlm.gov.

As used herein, the term "genetically modified" as applied to a cell, including a microorganism, means genetically engineered using recombinant DNA technology, and generally involves the step of synthesis of a suitable expression vector (see below) and then transfecting (i.e. stably or transiently) the expression vector into a host cell (generally stable transfection).

As used herein, the term "recombinant cell", "transformed cell", "recombinant plant" or "transformed plant" refers to a cell or plant comprising an exogenous nucleic acid stably integrated into the cellular genome that comprises a nucleotide sequence coding for TaLRRK-6D. In another embodiment, it may be a cell comprising a non-integrated (i.e., episomal) exogenous nucleic acid, such as a plasmid, cosmid, phagemid, or linear expression element, which comprises a sequence coding suitable for expression of a gene. In other embodiments, the present invention provides a cell line produced by stably transfecting a host cell, such as a plant host cell, with a plasmid comprising an expression vector of the invention. In one embodiment, the cell is engineered for heterologous expression of a gene.

The term "encode" as it is applied to nucleotide sequences refers to a nucleotide which is said to "encode" a polypeptide or peptide if, in its native state or when manipulated by methods well known to those skilled in the art, it can be transcribed and/or translated to produce the mRNA for the polypeptide and/or a fragment thereof.

The terms "polypeptide", "peptide" and "protein" are used interchangeably herein to refer to a polymer of amino acid residues. The terms also apply to amino acid polymers in which one or more amino acid residues is a modified residue, or a non-naturally occurring residue, such as an artificial chemical mimetic of a corresponding naturally occurring amino acid, as well as to naturally occurring amino acid polymers. The peptide may or may not be "isolated", that is to say removed from the components which exist around it when naturally occurring.

The term "amino acid" as used herein refers to naturally occurring and synthetic amino acids, as well as amino acid analogues and amino acid mimetics that have a function that is similar to naturally occurring amino acids. Naturally occurring amino acids are those encoded by the genetic code, as well as those modified after translation in cells (e.g. hydroxyproline, gammacarboxyglutamate, and O-phosphoserine). The phrase "amino acid analogue" refers to compounds that have the same basic chemical structure (an alpha carbon bound to a hydrogen, a carboxy group, an amino group, and an R group) as a naturally occurring amino acid but have a modified R group or modified backbones (e.g. homoserine, norleucine, methionine sulfoxide, methionine methyl sulphonium). The phrase "amino acid mimetic" refers to chemical compounds that have different structures from, but similar functions to, naturally occurring amino acids. It is to be appreciated that, owing to the degeneracy of the genetic code, nucleic acid molecules encoding a particular polypeptide may have a range of polynucleotide sequences. For example, the codons GCA, GCC, GCG and GCT all encode the amino acid alanine. The term "nucleic acid molecule" when used herein to include unmodified DNA or RNA or modified DNA or RNA. For example, the nucleic acid molecules or polynucleotides of the disclosure can be composed of single- and double stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically double-stranded or a mixture of single- and double-stranded regions. In addition, the nucleic acid molecules can be composed of triplestranded regions comprising RNA or DNA or both RNA and DNA. The nucleic acid molecules of the disclosure may also contain one or more modified bases or DNA or RNA backbones modified for stability or for other reasons. "Modified" bases include, for example, tritiated bases and unusual bases such as inosine. A variety of modifications can be made to DNA and RNA; thus "nucleic acid molecule" embraces chemically, enzymatically, or metabolically modified forms. The term "polynucleotide" shall have a corresponding meaning.

In this specification, the term "plant material" should be understood to mean any constituent of a plant comprising plant cells, including a plant cell, plant cell culture, plant tissue, plant, or seed from a plant.

The term "cell" should be understood to mean a cell from a plant. In a particularly preferred embodiment, the cell is a plant cell selected from the group consisting of: maize, rice, wheat, barley, sorghum, millet, oats, soybean and rye. The term "transgenic cell" should be understood to mean a cell that comprises a transgene incorporated, ideally stably incorporated, into its genome.

The term "transformation platform" should be understood to mean the genetic machinery required to transfer the transgene into a cell, and generally comprises an organism, for example a bacteria, capable of mediating cellular transformation and containing a recombinant construct of the invention. Examples of transformation platforms include *E. coli*, *A. tumefaciens*, *E. adhaerens*, and certain "transbacter" strains of bacteria. Other examples include: biolistic transformation and floral dipping.

The term "transgene" should be understood to mean the nucleotide of the invention, and functional variants thereof.

The term "overexpression" refers to expression of a gene or protein in an increased quantity relative to the wild-type. In one embodiment, the expression may be enhanced by transfection of an expression vector containing the necessary machinery to express TaLRRK-6D into a host cell. The expression may be enhanced by a promoter to produce multiple copies of mRNA and large quantities of the selected product TaLRRK-6D. The host cell may already express endogenous TaLRRK-6D.

The phrase "nucleotide of the invention" when used herein refers to SEQUENCE ID NO. 1 or a functional variant thereof or a functional fragment thereof.

The phrases "amino acid sequence of the invention" or "peptide of the invention" when used herein refer to SEQUENCE ID NO. 2 or a functional variant thereof or a functional fragment thereof.

BRIEF DESCRIPTION OF THE DRAWINGS

The invention will be more clearly understood from the following description of an embodiment thereof, given by way of example only, with reference to the accompanying drawings, in which:

Figure 4:
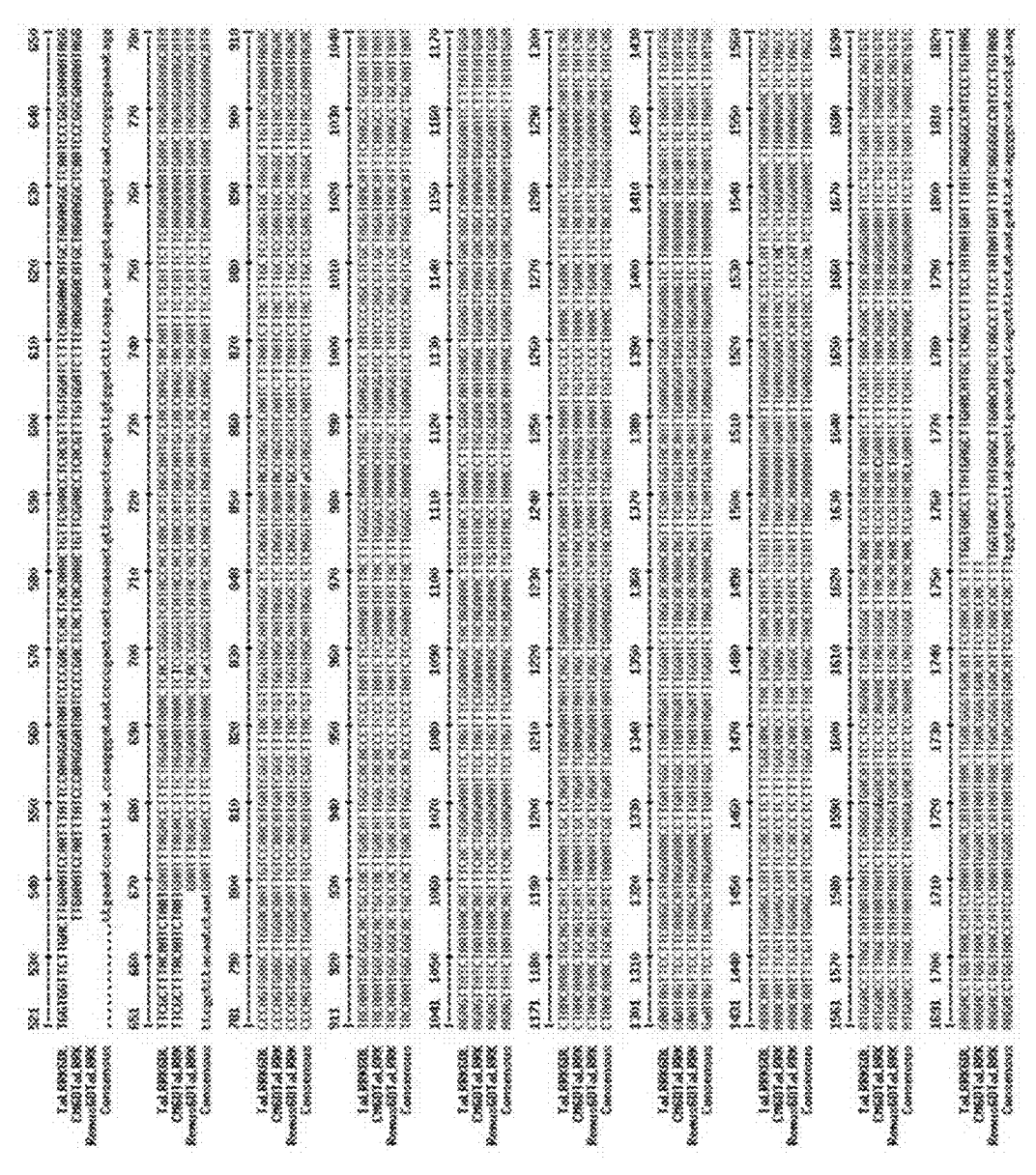

FIG. 4 illustrates the alignment of cloned 1300 bp specific to TaLRRK-6D.

DETAILED DESCRIPTION

The current inventors have surprisingly found that TaLRRK-6D is highly induced in response to FHB in wheat heads of resistant cultivars and that gene silencing leads to an increase in FHB symptoms.

The current invention provides a gene for resistance to *Fusarium* head blight (FHB) in plants.

Figure 1A:
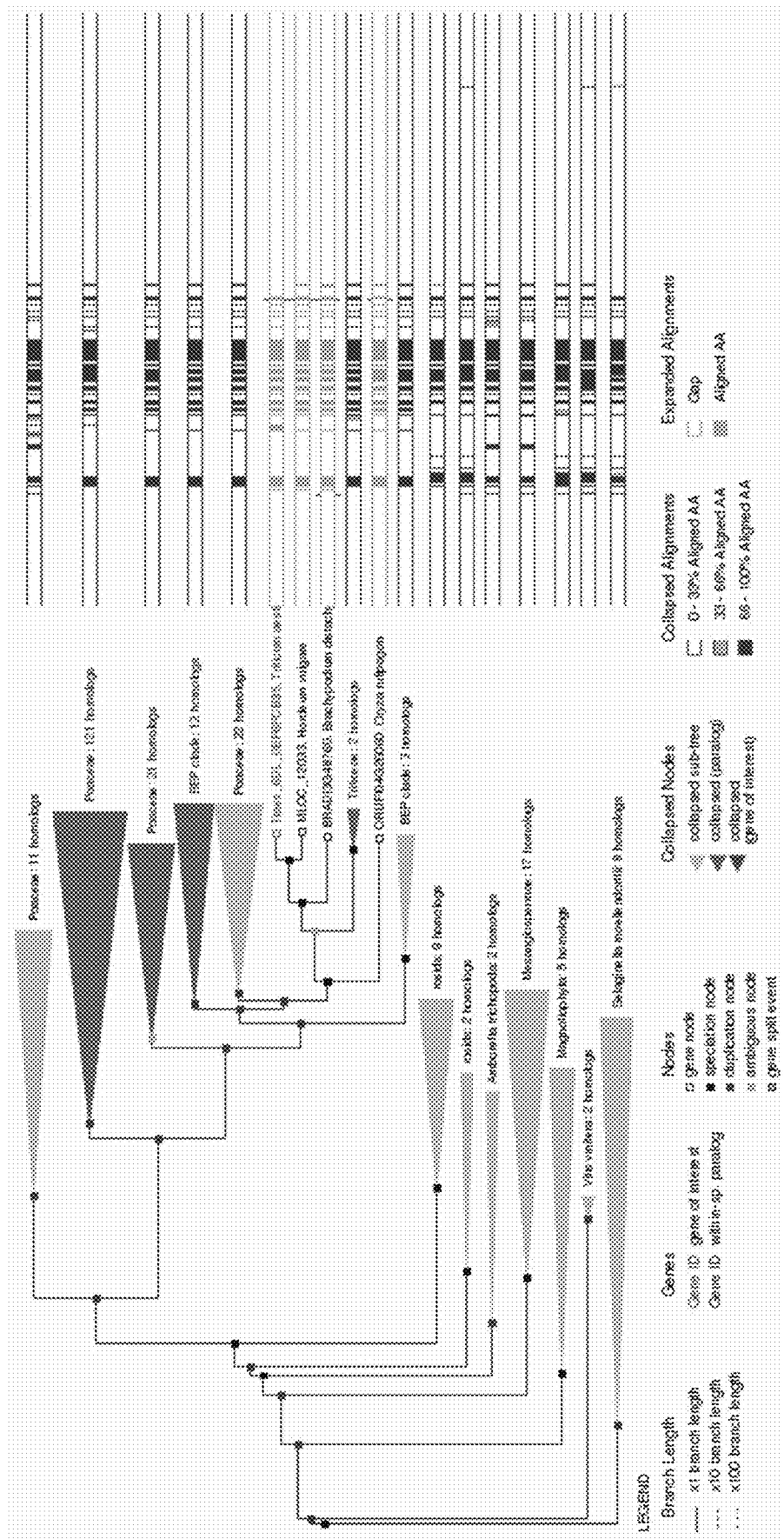
FIG. 1A illustrates a genetic map of the Poeceace Family.
Figure 1B:
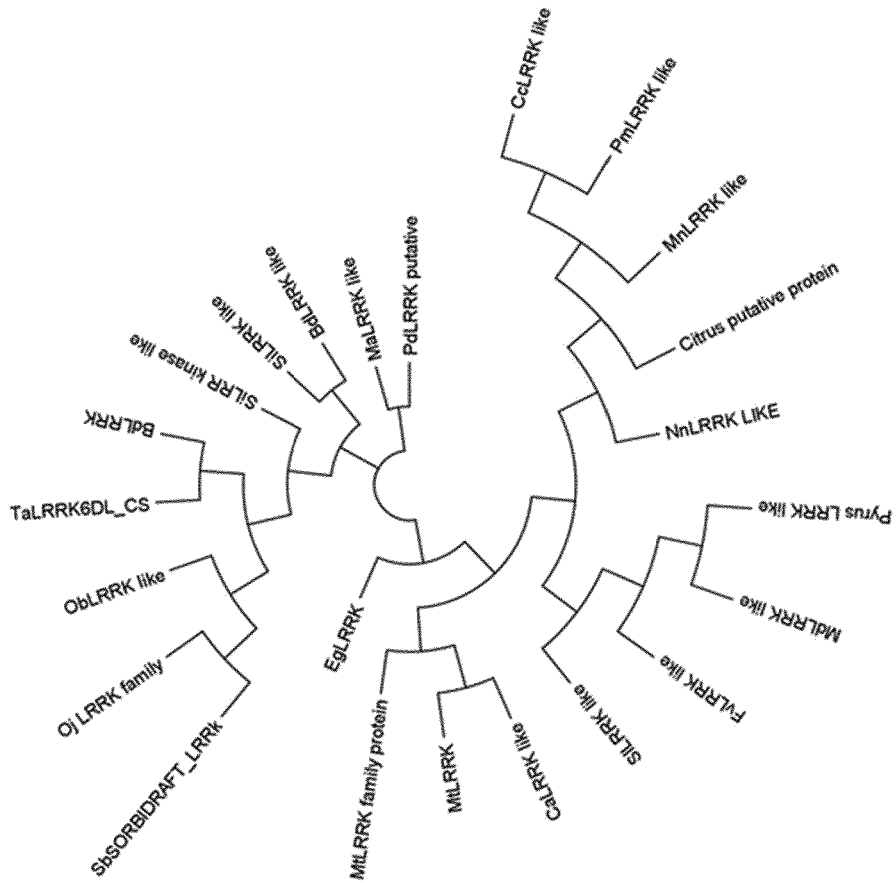
FIG. 1B is a homologue chart across 5 the cereal family.
Figure 2A:
FIG. 2A illustrates the transmembrane kinase protein, TaLRRK-6D.
Figure 2B:
FIG. 2B is a LRR-RLK family chart.

More specifically, the current invention provides a specific wheat (genome D homologue) of a leucine rich receptor kinase gene, TaLRRK-6D and a variant thereof for resistance to FHB in plants. The gene of the invention is termed TaLRRK-6D. TaLRRK-6D is restricted to the Poaceace Family (FIG. 1). It is found across the plant species but is confined to cereal family (FIG. 2).

Advantageously, as TaLRRK-6D is a native gene from the cultivars, the risk of resistance breakdown is greatly reduced. This provides longer and sustainable resistance in all conditions and genetic background.

TaLRRK-6D is a transmembrane kinase protein belonging to the LRR-RLK family. It has an amino acid sequence of 1031 amino acids in length and has a signal peptide, leucine rich repeats (LLR) domain, a transmembrane domain and a kinase domain.

The gene of the invention, TaLRRK-6D, has a nucleotide sequence of SEQUENCE ID NO.1 as follows:

ATGTCTGACCAATCCGTGAAACTCAACATGCTTCTTCTGCTGGCGTTTCT

GCTGCTGTCTTATGGAGCTGGCAATGCCCGTTGCTCAACTGTTCATGCGA

ACATCACAGACATTCTCTCCTTGCTCCGATTCAAAAGGTCCACCCACGAT

CCAACAGGTTCCTTGAGGAACTGGAACCGAAGCATCCATTACTGCAAGTG

GAATGGTGTCTCCTGCAGCTTACTGAATCAGGGCGGGTGGCGGCTTTGG

ATCTCCCTGGCCAAAACTTGTCAGGTCAAGTCAACCCTTCTCTTGGGAAC

TAACGTTCCTTAAGCGCCTGAATTTGTCCTCCAATGGCTTCTCCGGCCAG

TTACCTGACGCTTCTCAGCATGAGCTCCTACTTATTCCAAGGGATAATCC

CCGATTCACTCACACAATTTTCGAACCTACAGCTCCTGAATTTGTCCTAC

AATGGCTTCTCCGGCCAGTTACCTCCTCTGAACCAGCTTCCCGAGCTGGT

GGTTCTCAGCTTGAAATCCAATTTATTCCAAGGGATAATCCCCGACTCAC

TCACAAACTGTTCGAACCTCACGTTTGTGGATCTTTCAAGAAACATGCTA

GAAGGCTCAATCCCGGCGAAAATAGGTTCGCTTTACAATCTAATGAATTT

AGACCTTTCAATGAAATGACTCACCGGGGTCATACCACCAACCATCAGCA

ATGCCACCAAGCTACAATTTCTCATTCTTCAAGAAAACAAACTAGAGGGA

AGCATACCCATGAACTAGACTTGGACAATTGTCCAACATTATCGGCTTTA

CTGTTGGTAGCAATAGGCTCTCAGGTCAAATACCAGCATCAATCTTTAAT

CTTACTTTGCTCCGAGTGCCTGGCTTGTACGCAAATAGACTACAAATGGC

GGCACTGCCACTTGACATTGGCCACACCCTCCCTAATCTCCAAAATATTA

CTTTGGGCCAAAACATGCTTGAAGGTCCTATCCCAGCGTCGCCAAGTAAC

ATTTCAAGCCTGCAATAATCTCAGTTATCTAATAACAGTTTCACTGGAGA

AATTCCTAGTTTCGGAAAGCTACAGAAACTTGTATACCCTCACCTTGCGG

ACAATAAGCTGGAGTCAAGTGACAGCCAAAGATGGGAATCTTTATATGGA

CTGGCAAACTGCAGTCATCCTTAATCGCTCAGATTCAAGAATAATCAGCC

GCAAGGAGTCATACCAAATTCGGGGAGTCATACCAAATTCGGTAGGTAAA

TTGTCCCCTAAACTTGAACTTCTACATCTGGGTGGAAACAATCTATCAGG

AATAGTTCCTTCAAGCATAGGAAACCTTGATGGCTTAATAGATTTGGATC

TTAGCACAAACAGTTTCAATGGTACAATTGAAGGATGGGTAGGAAGTCTT

AAAAAACTACAATCTCTAGATCTTCATGGAAACAATTTCGTTGGAGCCAT

TCCACCCTCTTTTGGCAACCTTACTGAGCTAACATATCTGTATTTAGCAA

AAAATGAATTTGAAGGGACCATACCTCCCATTCTCGGGAAACTTAAAAGA

CTCTCAGCCATGGACCTTAGCTATAATAATCTTCAAGGTGACATTCCTCC

AGAACTCAGTGGGCTTACACAACTCCGTACACTGAATCTTTCATCTAACA

GACTTACAGGAGAAATTCCTGTTGATCTGAGCCAGTGTCAAGACCTGGTA

ACCATCCAAATGGACCATAATAACTTGACGGGTGACATTCCAACCACTTT

TGGTGACCTTATGAGCTTGAACATGCTCAGCCTTTCCTATAATGATTTAT

CAGGGGCCATCCCTGTAAGTCTTCAACATGTCAGCAAGTTGGACTTATCT

CATAATCACCTCCAAGGAGAAATCCCACCAGAAGGAGTGTTTAGGAATGC

CTCAGCCGTTTCGCTTGCTGGCAATTCAGAGCTTTGTGGAGGGGTGTCGG

AACTGCATATGCCTCCATGCCCAGTTGCTTCTCAGAGAACTAAGATACGA

TATTACTTGATCAGGGTATTGATACCATTATTTGGCTTCATGTCGCTCCT

ATTATTGGTCTACTTTCTAGTCCTCGAGAGGAAAATGAGAAGAACAAGAT

ATGAATCACAGGCTCCTTTGGGTGAGCATTTCCCTAAAGTTTCTTACAAT

GATCTGGTTGAAGCAACAAAGAACTTTTCCGAGTCTAACCTGCTTGGGAA

AGGAAGCTATGGTACAGTGTACAAGGGAAACTTGGTGCAGCATAAGTTGG

AAGTGGCAGTGAAGGTTTTTAACCTTGAGATGCAAGGCGCGGAGAGAAGC

TTCATGCCAGAATGTGAAGCGCTGAGAAGCGTTCAACACCGGAATCTTGT

TTCCATCATAACTGCATGTTCTACTGTTGATAGCGACGGTAGAGCTTTCA

-continued
```
GGGCCCTAATTTACGAGTTCATGCCCAAGGGGAACTTGGACACGTGCCTT

CATCACAAGGGGACGGCAAAGCTGATAAGCATCTGACTTTAACTCAAAG

AATCGGCATAGCTGTCAACATAGCAGATGCACTGGACTATTTACATAATG

ACAGCGAAAACCCCATCATCCATTGTGATCTGAAGCCCAGCAATATTCTT

CTTGATGAGGACATGGTTGCTCATTTGGGGGATTTCGGTATTGCAAGGAT

TTTTCTTGATTCTGGGCTAAGACCAGCAAGCTCGACGAGTTCAATTGGTG

TAAAAGGAACGATAGGCTATATCCCACCAGAGTACGGCGGGGGAGGCCGT

ATATCTACTTCTGGGGATGTCTACAGTTTTGGGATAGTGCTGCTGGAGAT

GTTGACTGGCAAAAGGCCAACAGATCCTATGTTTATGGATGGACTGGACA

TCGTCAACTTCGTGGGCAACAAGTTTCCACATCAAATACATGAAGTGATT

GACATTTATCTAAAAGGAGAGTGCGAGTCAGAAGATTCGGTTCATCAGTG

CCTCGTGTCTCTGCTGCAAGTAGCAGTCTCCTGCACACACTCCATCCCCG

GCGAAAGAGCGAACATTAGAGATACAGCTAGCAAGCTCCAGGAAATTAAG

GCGTCATATCTTGGAAGGAAGGCAAAGATAAATCCTTCAGTTTAA
```

TaLRRK-6D has an amino acid sequence of SEQUENCE ID NO.2 as follows:

```
MSDQSVKLNMLLLLAFLLLSYGAGNARCSTVHANITDILSLLRFKRSTHD

PTGSLRNWNRSIHYCKWNGVSCSLLNPGRVAALDLPGQNLSGQVNPSLGN

ITFLKRLNLSSNGFSGQLPDASQHELLLIPRDNPRFTHTIFEPTAPEFVL

QWLLRPVTSSEPASRAGGSQLEIQFIPRDNPRLTHKLFEPHVCGSFKKHA

RRLNPGENRFALQSNEFRPFNEMTHRGHTTNHQQCHQATISHSSRKQTRG

KHTHELDLDNCPTLSALLLVAIGSQVKYQHQSLILLCSECLACTQIDYKW

RHCHLTLATPSLISKILLWAKTCLKVLSQRRQVTFQACNNLSYLITVSLE

KFLVSESYRNLYTLTLRTISWSQVTAKDGNLYMDWQTAVILNRSDSRIIS

RKESYQIRGVIPNSVGKLSPKLELLHLGGNNLSGIVPSSIGNLDGLIDLD

LSTNSFNGTIEGWVGSLKKLQSLDLHGNNFVGAIPPSFGNLTELTYLYLA

KNEFEGTIPPILGKLKRLSAMDLSYNNLQGDIPPELSGLTQLRTLNLSSN

RLTGEIPVDLSQCQDLVTIQMDHNNLTGDIPTTFGDLMSLNMLSLSYNDL

SGAIPVSLQHVSKLDLSHNHLQGEIPPEGVFRNASAVSLAGNSELCGGVS

ELHMPPCPVASQRTKIRYYLIRVLIPLFGFMSLLLLVYFLVLERKMRRTR

YESQAPLGEHFPKVSYNDLVEATKNFSESNLLGKGSYGTVYKGNLVQHKL

EVAVKVFNLEMQGAERSFMPECEALRSVQHRNLVSIITACSTVDSDGRAF

RALIYEFMPKGNLDTCLHHKGDGKADKHLTLTQRIGIAVNIADALDYLHN

DSENPIIHCDLKPSNILLDEDMVAHLGDFGIARIFLDSGLRPASSTSSIG

VKGTIGYIPPEYGGGGRISTSGDVYSFGIVLLEMLTGKRPTDPMFMDGLD

IVNFVGNKFPHQIHEVIDIYLKGECESEDSVHQCLVSLLQVAVSCTHSIP

GERANIRDTASKLQEIKASYLGRKAKINPSV
```

In an embodiment of the invention, a variant of the gene is also provided. Typically, said variant has at least about 30% sequence identity with SEQUENCE ID NO. 1. In an embodiment, the variant has at least about 40%, 50%, 60% or 70% sequence identity to SEQUENCE ID NO. 1. In a preferred embodiment, the variant comprises at least about 70, 75, 80, 81, 82, 83, 84, 85, 86, 87, 88, 89, 90, 91, 92, 93, 94, 95, 96, 97, 98 or 99% sequence identity with SEQUENCE ID NO. 1, typically between from about 91.5% to about 95% sequence identity with SEQUENCE ID NO. 1. Typically, the variant is a functional variant.

The variant may have a sequence comprising (or consisting of) SEQUENCE ID NO. 3, SEQUENCE ID NO. 4, SEQUENCE ID NO. 5, SEQUENCE ID NO. 6, SEQUENCE ID NO. 7, SEQUENCE ID NO. 8, SEQUENCE ID NO. 9 or SEQUENCE ID NO. 10.

Preferably, the variant comprises (or consists of) a sequence of SEQUENCE ID NO. 3,
SEQUENCE ID NO. 4 or SEQUENCE ID NO. 5.
SEQUENCE ID NO. 3 is as follows:

```
ATGTCTGACCAATCCGTGAAACTCAACATGCTTCTTCTGCTGGCGTTTCT

GCTGCTGTCTTATGGAGCTGGCAATGCCCGTTGCTCAACTGTTCATGCGA

ACATCACAGACATTCTCTCCTTGCTCCGATTCAAAAGGTCCACCCACGAT

CCAACAGGTTCCTTGAGGAACTGGAACCGAAGCATCCATTACTGCAAGTG

GAATGGTGTCTCCTGCAGCTTACTGAATCCAGGGCGGGTGGCGGCTTTGG

ATCTCCCTGGCCAAAACTTGTCAGGTCAAGTCAACCCTTCTCTTGGGAAC

ATAACGTTCCTTAAGCGCCTGAATTTGTCCTCCAATGGCTTCTCCGGCCA

GTTACCTCCTCTGAGTCAGCTCCATGAGCTGACGCTTCTTGACATGAGCT

CTAACTTATTCCAAGGGATAATCCCCGATTCACTCACACAATTTTCGAAC

CTACAGCTCCTGAATTTGTCCTACAATGGCTTCTCCGGCCAGTTACCTCC

TCTGAACCAGCTTCCCGAGCTGGTGGTTCTTGACTTGAAATCCAATTTAT

TCCAAGGGATAATCCCCGACTCACTCACAAACTGTTCGAACCTCACGTTT

GTGGATCTTTCAAGAAACATGCTAGAAGGCTCAATCCCGGCGAAAATAGG

TTCGCTTTACAATCTAATGAATTTAGACCTTTCTAGGAATAAACTCACCG

GGGTCATACCACCAACCATCAGCAATGCCACCAAGCTACAATTTCTCATT

CTTCAAGAAATGAACTAGAGGGAAGCATACCCAGTGAGCTTGGACAATT

GTCCAACATGATCGGCTTTACTGTTGGTAGCAATAGGCTCTCAGGTCAAA

TACCAGCATCAATCTTTAATCTTACTTTGCTCCGAGTGCTAGGCTTGTAC

GCAAATAGACTACAAATGGCGGCACTGCCACTTGACATTGGCCACACCCT

CCCTAATCTCCAAAATATTACTTTGGGCCAAAACATGCTTGAAGGTCCTA

TCCCAGCGTCGCTAGGTAACATTTCAAGCCTGCAATTAATAGAGTTATCT

AATAACAGTTTCACTGGAGAAATTCCTAGTTTCGGAAAGCTACAGAAACT

TGTATACCTAAACCTTGCGGACAATAAGCTGGAGTCAAGTGACAGCCAAA

GATGGGAATCTTTATATGGACTAACAAACTGCAGTCATCTAAAATCGCTC

AGATTCAAGAATAATCAGCTGAAAGGAGTCATACCAAATTCGGTAGGTAA

ATTGTCCCCTAAACTTGAACTTCTACATCTGGGTGGAAACAATCTATCAG

GAATAGTTCCTTCAAGCATAGGAAACCTTGATGGCTTAATAGATTTGGAT

CTTAGCACAAACAGTTTCAATGGTACAATTGAAGGATGGGTAGGAAGTCT

TAAAAAACTACAATCTCTAGATCTTCATGGAAACAATTTCGTTGGAGCCA

TTCCACCCTCTTTTGGCAACCTTACTGAGCTAACATATCTGTATTTAGCA

AAAAATGAATTTGAAGGGACCATACCTCCCATTCTCGGGAAACTTAAAAG
```

-continued

```
ACTCTCAGCCATGGACCTTAGCTATAATAATCTTCAAGGTGACATTCCTC
CAGAACTCAGTGGGCTTACACAACTCCGTACACTGAATCTTTCATCTAAC
AGACTTACAGGAGAAATTCCTGTTGATCTGAGCCAGTGTCAAGACCTGGT
AACCATCCAAATGGACCATAATAACTTGACGGGTGACATTCCAACCACTT
TTGGTGACCTTATGAGCTTGAACATGCTCAGCCTTTCCTATAATGATTTA
TCAGGGGCCATCCCTGTAAGTCTTCAACATGTCAGCAAGTTGGACTTATC
TCATAATCACCTCCAAGGAGAAATCCCACCAGAAGGAGTGTTTAGGAATG
CCTCAGCCGTTTCGCTTGCTGGCAATTCAGAGCTTTGTGGAGGGGTGTCG
GAACTGCATATGCCTCCATGCCCAGTTGCTTCTCAGAGAACTAAGATACG
ATATTACTTGATCAGGGTATTGATACCATTATTTGGCTTCATGTCGCTCC
TATTATTGGTCTACTTTCTAGTCCTCGAGAGGAAAATGAGAAGAACAAGA
TATGAATCACAGGCTCCTTTGGGTGAGCATTTCCCTAAAGTTTCTTACAA
TGATCTGGTTGAAGCAACAAAGAACTTTTCCGAGTCTAACCTGCTTGGGA
AAGGAAGCTATGGTACAGTGTACAAGGGAAACTTGGTGCAGCATAAGTTG
GAAGTGGCAGTGAAGGTTTTTAACCTTGAGATGCAAGGCGCGGAGAGAAG
CTTCATGCCAGAATGTGAAGCGCTGAGAAGCGTTCAACACCGGAATCTTG
TTTCCATCATAACTGCATGTTCTACTGTTGATAGCGACGGTAGAGCTTTC
AGGGCCCTAATTTACGAGTTCATGCCCAAGGGGAACTTGGACACGTGCCT
TCATCACAAGGGGACGGCAAAGCTGATAAGCATCTGACTTTAACTCAAA
GAATCGGCATAGCTGTCAACATAGCAGATGCACTGGACTATTTACATAAT
GACAGCGAAAACCCCATCATCCATTGTGATCTGAAGCCCAGCAATATTCT
TCTTGATGAGGACATGGTTGCTCATTTGGGGATTTCGGTATTGCAAGGA
TTTTTCTTGATTCTGGGCTAAGACCAGCAAGCTCGACGAGTTCAATTGGT
GTAAAAGGAACGATAGGCTATATCCCACCAGAGTACGGCGGGGAGGCCG
TATATCTACTTCTGGGGATGTCTACAGTTTTGGGATAGTGCTGCTGGAGA
TGTTGACTGGCAAAAGGCCAACAGATCCTATGTTTATGGATGGACTGGAC
ATCGTCAACTTCGTGGGCAACAAGTTTCCACATCAAATACATGAAGTGAT
TGACATTTATCTAAAAGGAGAGTGCGAGTCAGAAGATTCGGTTCATCAGT
GCCTCGTGTCTCTGCTGCAAGTAGCAGTCTCCTGCACACACTCCATCCCC
GGCGAAAGAGCGAACATTAGAGATACAGCTAGCAAGCTCCAGGAAATTAA
GGCGTCATATCTTGGAAGGAAGGCAAAGATAAATCCTTCAGTT
```

SEQUENCE ID NO. 4 is as follows:
(Cultivar Remus Chromosome 6D Variant—TaLRRK-6D)

```
ATGTCTGACCAATCCGTGAAACTCAACATGCTTCTTCTGCTGGCGTTTCT
GCTGCTGTCTTATGGAGCTGGCAATGCCCGTTGCTCAACTGTTCATGCGA
ACATCACAGACATTCTCTCCTTGCTCCGATTCAAAAGGTCCACCCACGAT
CCAACAGGTTCCTTGAGGAACTGGAACCGAAGCATCCATTACTGCAAGTG
GAATGGTGTCTCCTGCAGCTTACTGAATCCAGGGCGGGTGGCGGCTTTGG
ATCTCCCTGGCCAAAACTTGTCAGGTCAAGTCAACCCTTCTCTTGGGAAC
ATAACGTTCCTTAAGCGCCTGAATTTGTCCTCCAATGGCTTCTCCGGCCA
GTTACCTGACGCTTCTCAACATGAGCTCTTACTTATTCCAAGGGATAATC
CCCGATTCACTCACACAATTTTCGAACCTACAGCTCCTGAATTTGTCCTA
CAATGGCTTCTCCGGCCAGTTACCTCCTCTGAACCAGCTTCCCGAGCTGG
TGGTTCTCAACTTGAAATCCAATTTATTCCAAGGGATAATCCCCGACTCA
CTCACAAACTGTTCGAACCTCACGTTTGTGGATCTTTCAAGAAACATGCT
AGAAGGCTCAATCCCGGCGAAAATAGGTTCGCTTTACAATCTAATGAATT
TAGACCTTTCAACGAAATGACTCACCGGGGTCATACCACCAACCATCAGC
CAATGCCACCAAGCTACAATTTCTCATTCTTCAAGAAAATGCACCTAGAG
GGGAAGCATACCCAGCTAGCTTGGACAATTGTCCAACATGATTCGGCTTT
ACTGGTTGGAAGCAATAAGGCTCTCAGGTCAAATGCCCAGCATGCAATCT
TTAAATCTTACTTTGGATCCAAGTGCTTAGGTTGGTACGCCAACAAAACT
ACCAAATGGCGGGCACTGCCAATTAGAATTGGGCCAAACCCTCCCCTAAT
TTCCAAAAAATTAACTTTGGGCCCAAAAAAGGCTATGAAGGTCCTATCCC
AGCGTCGCTCGGTAACATTTCAAGCCTGCAATCTCCAAAGTTATCCAATT
ACAGTTTCACTGGAGAAATTCCTAGTTTCGGAAAGCTACAGAAACTTGTA
TACCTATACCTTGCGGACAATAAGCTGGAGTCAAGTGACAGCCAAAGATG
GGAATCTTTATATGGACCAGCAAACTGCAGTCATCCACAATCGCTCAGAT
TCAAGAATAATCAGCCAGAAGGAGTCTTACCAAATTCGGAGCGTAAATTG
TCCCCTAAACTTGAACTTCTACATCTGGGGTGGAAACAATCTATCAGGAA
TAGTTCCTTCAAGCTCCGGAAACCTTGATGGCTTAATAGATTTGGATCTT
AGCACAAACAGTTTCAATGGTACAATTGAAGGATGGGTAGGAAGTCTTAA
AAAACTACAATCTCTAGATCTTCATGGAAACAATTTCGTTGGAGCCATTC
CACCCTCTTTTGGCAACCTTACTGAGCTAACATATCTGTATTTAGCAAAA
AATGAATTTGAAGGGACCATACCTCCCATTCTCGGGAAACTTAAAAGACT
CTCAGCCATGGACCTTAGCTATAATAATCTTCAAGGTGACATTCCTCCAG
AACTCAGTGGGCTTACACAACTCCGTACACTGAATCTTTCATCTAACAGA
CTTACAGGAGAAATTCCTGTTGATCTGAGCCAGTGTCAAGACCTGGTAAC
CATCCAAATGGACCATAATAACTTGACGGGTGACATTCCAACCACTTTTG
GTGACCTTATGAGCTTGAACATGCTCAGCCTTTCCTATAATGATTTATCA
GGGGCCATCCCTGTAAGTCTTCAACATGTCAGCAAGTTGGACTTATCTCA
TAATCACCTCCAAGGAGAAATCCCACCAGAAGGAGTGTTTAGGAATGCCT
CAGCCGTTTCGCTTGCTGGCAATTCAGAGCTTTGTGGAGGGGTGTCGGAA
CTGCATATGCCTCCATGCCCAGTTGCTTCTCAGAGAACTAAGATACGATA
TTACTTGATCAGGGTATTGATACCATTATTTGGCTTCATGTCGCTCCTAT
TATTGGTCTACTTTCTAGTCCTCGAGAGGAAAATGAGAAGAACAAGATAT
GAATCACAGGCTCCTTTGGGTGAGCATTTCCCTAAAGTTTCTTACAATGA
TCTGGTTGAAGCAACAAAGAACTTTTCCGAGTCTAACCTGCTTGGGAAAG
GAAGCTATGGTACAGTGTACAAGGGAAACTTGGTGCAGCATAAGTTGGAA
GTGGCAGTGAAGGTTTTTAACCTTGAGATGCAAGGCGCGGAGAGAAGCTT
CATGCCAGAATGTGAAGCGCTGAGAAGCGTTCAACACCGGAATCTTGTTT
```

CCATCATAACTGCATGTTCTACTGTTGATAGCGACGGTAGAGCTTTCAGG

GCCCTAATTTACGAGTTCATGCCCAAGGGGAACTTGGACACGTGCCTTCA

TCACAAGGGGACGGCAAAGCTGATAAGCATCTGACTTTAACTCAAAGAA

TCGGCATAGCTGTCAACATAGCAGATGCACTGGACTATTTACATAATGAC

AGCGAAAACCCCATCATCCATTGTGATCTGAAGCCCAGCAATATTCTTCT

TGATGAGGACATGGTTGCTCATTTGGGGGATTTCGGTATTGCAAGGATTT

TTCTTGATTCTGGGCTAAGACCAGCAAGCTCGACGAGTTCAATTGGTGTA

AAAGGAACGATAGGCTATATCCCACCAGAGTACGGCGGGGGAGGCCGTAT

ATCTACTTCTGGGGATGTCTACAGTTTTGGGATAGTGCTGCTGGAGATGT

TGACTGGCAAAAGGCCAACAGATCCTATGTTTATGGATGGACTGGACATC

GTCAACTTCGTGGGCAACAAGTTTCCACATCAAATACATGAAGTGATTGA

CATTTATCTAAAAGGAGAGTGCGAGTCAGAAGATTCGGTTCATCAGTGCC

TCGTGTCTCTGCTGCAAGTAGCAGTCTCCTGCACACACTCCATCCCCGGC

GAAAGAGCGAACATTAGAGATACAGCTAGCAAGCTCCAGAAAAAGGTCGT

CAACTGCCCCCTAA

SEQUENCE ID NO. 5 is as follows:
2 Cultivar Chinese Spring (CS) Chromosome 6D Variant—
TRIAE_CS42_6 DL_TGACv1_527217_AA1700660.1

ATGTCTGACCAATCCGTGAAACTCAACATGCTTCTTCTGCTGGCGTTTCT

GCTGCTGTCTTATGGAGCTGGCAATGCCCGTTGCTCAACTGTTCATGCGA

ACATCACAGACATTCTCTCCTTGCTCCGATTCAAAAGGTCCACCCACGAT

CCAACAGGTTCCTTGAGGAACTGGAACCGAAGCATCCATTACTGCAAGTG

GAATGGTGTCTCCTGCAGCTTACTGAATCCAGGGCGGGTGGCGGCTTTGG

ATCTCCCTGGCCAAAACTTGTCAGGTCAAGTCAACCCTTCTCTTGGGAAC

ATAACGTTCCTTAAGCGCCTGAATTTGTCCTCCAATGGCTTCTCCGGCCA

GTTACCTCCTCTGAGTCAGCTCCATGAGCTGACGCTTCTTGACATGAGCT

CTAACTTATTCCAAGGGATAATCCCCGATTCACTCACACAATTTTCGAAC

CTACAGCTCCTGAATTTGTCCTACAATGGCTTCTCCGGCCAGTTACCTCC

TCTGAACCAGCTTCCCGAGCTGGTGGTTCTTGACTTGAAATCCAATTTAT

TCCAAGGGATAATCCCCGACTCACTCACAAACTGTTCGAACCTCACGTTT

GTGGATCTTTCAAGAAACATGCTAGAAGGCTCAATCCCGGCGAAAATAGG

TTCGCTTTACAATCTAATGAATTTAGACCTTTCTAGGAATAAACTCACCG

GGGTCATACCACCAACCATCAGCAATGCCACCAAGCTACAATTTCTCATT

CTTCAAGAAAATGAACTAGAGGGAAGCATACCCAGTGAGCTTGGACAATT

GTCCAACATGATCGGCTTTACTGTTGGTAGCAATAGGCTCTCAGGTCAAA

TACCAGCATCAATCTTTAATCTTACTTTGCTCCGAGTGCTAGGCTTGTAC

GCAAATAGACTACAAATGGCGGCACTGCCACTTGACATTGGCCACACCCT

CCCTAATCTCCAAAATATTACTTTGGGCCAAAACATGCTTGAAGGTCCTA

TCCCAGCGTCGCTAGGTAACATTTCAAGCCTGCAATTAATAGAGTTATCT

AATAACAGTTTCACTGGAGAAATTCCTAGTTTCGGAAAGCTACAGAAACT

TGTATACCTAAACCTTGCGGACAATAAGCTGGAGTCAAGTGACAGCCAAA

GATGGGAATCTTTATATGGACTAACAAACTGCAGTCATCTAAAATCGCTC

AGATTCAAGAATAATCAGCTGAAAGGAGTCATACCAAATTCGGTAGGTAA

ATTGTCCCCTAAACTTGAACTTCTACATCTGGGTGGAAACAATCTATCAG

GAATAGTTCCTTCAAGCATAGGAAACCTTGATGGCTTAATAGATTTGGAT

CTTAGCACAAACAGTTTCAATGGTACAATTGAAGGATGGGTAGGAAGTCT

TAAAAAACTACAATCTCTAGATCTTCATGGAAACAATTTCGTTGGAGCCA

TTCCACCCTCTTTTGGCAACCTTACTGAGCTAACATATCTGTATTTAGCA

AAAAATGAATTTGAAGGGACCATACCTCCCATTCTCGGGAAACTTAAAAG

ACTCTCAGCCATGGACCTTAGCTATAATAATCTTCAAGGTGACATTCCTC

CAGAACTCAGTGGGCTTACACAACTCCGTACACTGAATCTTTCATCTAAC

AGACTTACAGGAGAAATTCCTGTTGATCTGAGCCAGTGTCAAGACCTGGT

AACCATCCAAATGGACCATAATAACTTGACGGGTGACATTCCAACCACTT

TTGGTGACCTTATGAGCTTGAACATGCTCAGCCTTTCCTATAATGATTTA

TCAGGGGCCATCCCTGTAAGTCTTCAACATGTCAGCAAGTTGGACTTATC

TCATAATCACCTCCAAGGAGAAATCCCACCAGAAGGAGTGTTTAGGAATG

CCTCAGCCGTTTCGCTTGCTGGCAATTCAGAGCTTTGTGGAGGGGTGTCG

GAACTGCATATGCCTCCATGCCCAGTTGCTTCTCAGAGAACTAAGATACG

ATATTACTTGATCAGGGTATTGATACCATTATTTGGCTTCATGTCGCTCC

TATTATTGGTCTACTTTCTAGTCCTCGAGAGGAAAATGAGAAGAACAAGA

TATGAATCACAGGCTCCTTTGGGTGAGCATTTCCCTAAAGTTTCTTACAA

TGATCTGGTTGAAGCAACAAAGAACTTTTCCGAGTCTAACCTGCTTGGGA

AAGGAAGCTATGGTACAGTGTACAAGGGAAACTTGGTGCAGCATAAGTTG

GAAGTGGCAGTGAAGGTTTTTAACCTTGAGATGCAAGGCGCGGAGAGAAG

CTTCATGCCAGAATGTGAAGCGCTGAGAAGCGTTCAACACCGGAATCTTG

TTTCCATCATAACTGCATGTTCTACTGTTGATAGCGACGGTAGAGCTTTC

AGGGCCCTAATTTACGAGTTCATGCCCAAGGGGAACTTGGACACGTGCCT

TCATCACAAGGGGACGGCAAAGCTGATAAGCATCTGACTTTAACTCAAA

GAATCGGCATAGCTGTCAACATAGCAGATGCACTGGACTATTTACATAAT

GACAGCGAAAACCCCATCATCCATTGTGATCTGAAGCCCAGCAATATTCT

TCTTGATGAGGACATGGTTGCTCATTTGGGGGATTTCGGTATTGCAAGGA

TTTTCTTGATTCTGGGCTAAGACCAGCAAGCTCGACGAGTTCAATTGGT

GTAAAAGGAACGATAGGCTATATCCCACCAGAGTACGGCGGGGGAGGCCG

TATATCTACTTCTGGGGATGTCTACAGTTTTGGGATAGTGCTGCTGGAGA

TGTTGACTGGCAAAAGGCCAACAGATCCTATGTTTATGGATGGACTGGAC

ATCGTCAACTTCGTGGGCAACAAGTTTCCACATCAAATACATGAAGTGAT

TGACATTTATCTAAAAGGAGAGTGCGAGTCAGAAGATTCGGTTCATCAGT

GCCTCGTGTCTCTGCTGCAAGTAGCAGTCTCCTGCACACACTCCATCCCC

GGCGAAAGAGCGAACATTAGAGATACAGCTAGCAAGCTCCAGGAAATTAA

GGCGTCATATCTTGGAAGGAAGGCAAAGATAAATCCTTCAGTTTAA

SEQUENCE ID NO. 6 is as follows:
TRIAE_CS42_2 AL_TGACv1_093509_AA0281510.6

ATGAAGCTCTTCGTGCTCGTAGCATGGGCACTGTTGTTATTGTCTCATGG
ATCTGGAAGCGTCATTTGCGCCGTCCTCCATGGGAACGATACAGATATGC
TGTCGCTTCTTGATTTCAAGCGCGCAATCACCGAAGATCCGAAAGGGCTC
TTGAGCACATGGAACACCAGCATTCATTTCTGCAACTGGCAGGGTGTGAA
GTGCAGCCTCACAGAGCATGAGCGTGTTGCAGAGCTGGACCTGTCTGAGC
AGAGTTTTGTCGGGGAAATCTCTCCTTCCCTTGGAAACATGTCATATCTT
ACTTATCTTAACCTTTCCAGAAGCAAGTTCTCTGGTCAGATACCACATTT
TGGCCGGCTGCGAGAGCTGGAGTTTCTTGACCTGAGTCACAACTCGCTAC
AAGGGATTATTCCAGTGACGCTCACAAACTGCTCCAACTTGAGGGCGTTA
GACCTCTCAAGAAACTTATTGGTGGGTGAAATTCCCGCAGAAATATCCCT
TCTCTCCAACCTGACACGCTTGTGGCTTTCTTATAATGATCTTACCGGGG
TCATTCCACCAGGCCTTGGCAATATCACTTCTCTAGAACATGTTATTCTG
ATGTATAACCGGTTAGAGGGAGGCATTCCTGATGAGTTTGGGAAGTTGTC
CAAGATGTCAAACTTACTCCTTGGTGAAAACAAGCTATCAGGTAGAGTCC
CAAAGGCCATTTTTAATCTGTCTCTGCTAAATCAAATGGCGCTGGAGTTG
AATATGCTAGTTGGTACTCTACCATCTAACATGGGTGATGCTCTCCCTAA
CCTCCGACTTCTTACATTGGGTGGTAACATGCTGGAAGGTCTTATCCCTG
ACTCATTAGGCAATGCATCCGAGCTACAGCTGATAAACTTAGCATATAAT
CACGGGTTTAGAGGACGAGTCCCACCTTCTCTTGGTAAACTTCCGAAGCT
CAGTAAGCTAGGTCTTGACACAAACAGTCTTGAAGCAAATGACAGCTGGG
GCTGGGAATTCTTGGATGCATTGAGCAACTGCACTTCTCTAGAGATGCTT
TCACTCTATGCAAATCGGCTACAAGGAAACTTGCCAAATTCTGTTGGCAA
CCTTTCGTCTAATGTTAACAACCTCGTGTTTGGTAGGAATATGCTATATG
GATTAGTTCCGTCAAGCATAGGAAATCTCCATAGACTAACTAAGCTAGGA
CTGGAGGAGAACAGTTTGACTGGTCCGATTGATGGATGGGTTGGAAATCT
TGCTATTTGCAAGGTTTATATCTTCAACAGAACAATTTCACCGGGCAGAT
TCCAACTTCCATTGGCAATAACTCCAAGCTGTCAGAACTGTTTCTGGCAA
ATAATCAATTCCACGGTCCCATTCCATCAAGTTTCGAAAACCTTCAGCAA
CTCTTGTATTTAGACCTCAGCTATAACAATCTTCAAGAAAATATACCAAA
AGAGCTTTTTAGTATAGCCACAATTGCCCAATGTGCGCTATCCCACAACA
GTCTAGAAGGCCAAATTCCTCACATCAGTAATCTTCAACAACTCAACTAT
CTAGATCTTTCATCCAACAAGCTTACAGGGGAAATTCCACCTACTTTGCG
CACATGCCAGCAATCGCAAGCCATCAAATTGGACCGGAACTTCCTCTCGG
GAAGCATTCCCATGTTTCTAGGGAGTCTGAACAGCTTGATCGAGCTCAAC
CTTTCACATAACAATCTCTCAGGCTCTATCCCAATTGCTCTAAGCAAACT
GCAACTTCTCACCCAGTTGGATCTATCCGACAATCATCTTGAAGGAGAAG
TACCAGTAGAAGGAATATTCAAAAATACAACAGCCATTTCCCTGAAAGGC
AATTGGCGGCTTTGTGGAGGTGTGCTGGACCTACATATGCCTTCATGCCC
CGCTGCTTCTCATAGAAGATCTAGATGGCAATACTATTTGGTGAGAGTAT
TGGTCCCTATATTAGGCATCTTGTTACTCATATTAGTAGTCTGCTTATCC
CTTCTCAGAAAGAGGATGCTGAGGATGCAGTTATCGTTGCCTTCTTCCGA
TGAGCAATTCCCTAAAGTATCTTATAAGGATCTACCACAGGCTACTGAGA
ACTTCACAGTATATAACTTGATTGGGAGAGGAAGCTGCGGTTCAGTGTAC
AGAGCAAAGCTAAACCAAAAACAGATGGTTGTGGCAGTGAAAGTTTTTGA
CCTTGACATGCAAGGCGCGGATAAAAGTTTCATCTCAGAATGTAAAGCAC
TGAGAAACATTCGGCACCGTAATCTTCTTCCAATTCTGACTGCATGCTCA
ACAATTGATAACCAAGGCCGGGATTTCAAAGCTCTAGTCTACCAGTTCAT
GCCCAACGGCAACCTGGACACTTGGCTGCACCCGGCAGGAGATGGAAAAG
CCCCAAAGCAACTGGACCTCTCTCAAAGAATGAAAATAGCTGTTGATATA
GCCGATGCATTGCAATATATACACCATGACTGTGAGAATCCTATTGTTCA
CTGTGATTTGAAGCCCAGCAATATCCTCCTAGATTATGATATGACAGCTC
GTTTGGGGACTTTGGCATCGCAAGGTTGTACATCAAATCCAAATCAGCG
GCAGCTGGAGGTTCGAGTTCAATGGGTACAATAACTCTGAGGGGCACGAT
TGGATATATTGCTCCAGAGTATGCGGGAGGTGGCTACCTATCGACGTCTG
GAGACGCGTACAGTTTTGGGATAGTGCTGCTGGAGATGCTGACAGGAAGA
AGGCCGACCGACCCTATGTTCTGCGAGGGGCTTGACATCGTGAACTTTGT
CAAGAGGAACTTTCCGGATCAGATACTTGATATCCTTGACGTTCTCTCC
GAGAAGAATGTCAAGACTGTTCTCAGGATAATCTGGAAGGAGAAAACGAA
GTCCACCGGTGCCTGCTGTCCTTGCTGAAAGTGGCACTTTCTTGCGCAAG
CCAGGATCCTAACGAACGAATGAACATGAGAGAAGCAGCTACTGAATTGC
ACGCGATCGACACATTGTATGTGTCTTGA

SEQUENCE ID NO. 7 is as follows:
TRIAE_CS42_2 BL_TGACv1_132242_AA0436300.1

ATGTCTGTGACGAGACTCAGCATGGTTAATCTGCTGGCGTTTTTGCTGCT
GCTGTTCTATGGAGCTGGCAACATCAATTGCTCAACAGTCAATCACGAGA
ACAGTAGAGACATGCGCTCGTTGCTGGATTTCAAAGCGGCTACCAACGAC
CCAACAGATGCCTTGAGATCCTGGGACAGAAGCGTCCACTACTGCAACTG
GACGGGTGTCATTTGCAGCTCATTGTGTCCAGGGCGTGTCGCCGCTCTGC
AACTCGCCGGCCAAAGCTTGTCTGGCGAGATCACCCCCTCTCTTGGGAAC
TTAACGTTCCTTAAGGTCCTCAACTTGTCCTCCAATGGCTTCTCAGGCCA
GTTAACTCCCCTAAACCTAAACCAACTCCATGAGCTGGTCCTCCTTGACC
TCAGCTCCAATTCATTCCAGGGGACGATTCCTGACTCACTCATGAATTGT
TCAAAACTACAGTATCTAGTTCTTTCTGGAAACATGCTAGAAGGTCCAAT
CCCCAAGAAATTGGTTCTCTTTATAATCTATTAGGCTTAGGCCTTTCTA
GGAATAATCTTATTGGGGTCATCCCACTAACCATCAGCAACTCCACCCAG
TTAGAACAACTTAGCCTTGAAGAAAATCAACTAGGGGGGAGCATTCCTGA
TGTGTTTGGGCAATGGTCCAAGATGTTGGAATTGTCCGTAGGTGAAAATA
GGCTCTCAGGTCGAATACCACCTTCAATCTTTAATCTGACTTCGCTTCAA
ATATTAGATTTGTATGCAAATAAGCTACAAGGGGAATTGCTGCTTGACAT

-continued

```
TGGCGATACCCTCCCTGAAATCATAATTTTTACGCTGGGCCAGAACATTC

TTGAAGGTCACATCCCAGCTTCCCTAGGAAACGCTTCACGGCTGCAAGTG

ATAGATTTGTCTTCTAACAGTTTCGTTGGAGAAATTCCTACTTTCGGAAA

GCTACTAAACCTTATGAACATGAACCTTGGATATAATATGCTTGAATCAA

GTGAAAGCCAAAGATGGGAATCCTTGTATGGACTAACAAACTGTAGTAAT

CTATATGCGCTAACATTAGATAGTAATCAGCTGCAAGGAGCCATACCAGA

TTTGGTCGGTAGGTTATCCACTAAACTCAGACGTCTACACATGGGTGGAA

ACAATCTGTCGGGAATAGTTCCTTTAAGCCTAGCAAACCTTAGTAGCATA

ATCGATTTGGATCTTAGCAACAACAATTTAACTGGTACAGTCGAAGGATG

GTTAGGGAGTCTCAAAAACTTACAATCTTTAGATCTTCATGGAAATAATT

TCATTGGATCCATTCCACCATCTTTTGGCAACCTTTCAGAACTGACAATA

CTTTCTTTAGCACAAAATGAATTTAAAGGTCACATACCTCCCACATTAGG

AAAACTTTCACAACTCTCAAGGCTGGACCTTAGCTATAATAATCTGCAAG

GTGACATACCTCCAGAAATTAGTGAGCTTAAACAACTCATTGCACTATAC

CTCTCTTCTAGCAGACTCTCGGGAAAAATTCCTGATGATCTGGGCAAGTG

TCAGGGCCTCGTAACCATCCAAATGGACCACAATAATCTCACGGGCGTCA

TTCCAACCTCTTTAGGCAACCTTTTGAGCTTGTACATGCTCAACCTGTCC

TATAATGATTTATCAGGTGCCATCCCAACAGTTCTAAGTGACCTTCAACT

TCTTAGCAAGTTAGACCTATCATATAATCGTCTCCAAGGAGCACTCCCAA

GAAATGGAGTGTTTGAGCACCCTGCAAACGTTTCACTTGATGGCAACCAG

GGACTTTGTGGACGGGCAACCGGTTTCCATGTGCCCTCATGCCCAGATGC

CTCGCCGAGAACAGGAAGACATTATCGTTTGCTTACGGTGTTGATCCCAA

TAATTGGCTTCCTGTCGCTGGCACTGTTGACTTGCTTTATAATCCATGAG

AAGATACCACAAGCAACGTTTTCATTGTTGCCTTCTCTTAGGGAGAAATT

CCCTAGAGTTTCTTACTGGGATCTAGCTCGAGCGACAGGCAACTTCTCTG

AGATTAACTTGATTGGCGAAGGAAGTTACAGTTCAGTGTACAAAGGAAAG

TTGAGACAAGTTAAAACGGAAATAGCAGTCAAGATACTTGACCTTGACAT

TCCAGGTGCCGAAGGAAGTTTTGCATTAGAATGCAAAGCGTTGAGAGGCA

TCCGTCACAGAAACATTGTTCCTCTCATAACTGAATGCTCTGCAATCGAC

AACAAAGGCAATGCTTTCAGAGCTCTAATCTATGCTTTCATGCCCAATGG

CAACTTGGATACTTGGTTGCATCATCAAGGGAATCAGGCAGCTGCAAGGC

ATTTAAGCTTAGCTCAAAGAATAAACATCGCTATTAACATAGCTGATGCA

TTGGACTATCTGCACCATGATACTTGGAGGCCCATCATCCATTGTGATTT

GAAGCCGAGTAACATACTCCTAGACATTCATATGAATGCCTGTCTGGGAG

ACTTTGGCATCGCAAGGTTCTACATTGATTCTAAACTAAGAACGGTCGGA

GATTCAAGTTCAATTGCTGCAAACGGCACTCTGGGATATATGGCTCCAGA

GTATGCTGAAAGCGGTCATGCATCTACTTGTGGGGACGTATATAGTTTCG

GAATAGTACTCTTGGAGATGCTGACAGGAAAAAGACCAACAGATCATATG

TTCAGGAATGAACTCACCATTGTCAGATTTGTGGAAACGAATTTTCCTGA

TCACATATTAAATTTTCTGGATTCCTGTCTGCTAGATGAATGCAATGATG
```

CCATCAACCAAGTAGCAGCAGGACTGGAAAATCCGGCAATCTTTCAGTCC

TTGTTATCTTTGCTACGGATAGCACTTCTTTGTACACGCCAATCCCCAAC

TGAACGGCTTAACATGAGGGAAGTAGCTACCCAAATGCACAAAATCAACG

TGGTGAACACGGGAGGGAGAGTGAGGAGCTCAACTTCTTTTAAGAGACTT

GTCAGCTGGGCTTCTCAATGGAGCTAA

SEQUENCE ID NO. 8 is as follows:
TRIAE_CS42_2 DL_TGACv1_158196_AA0512090.2

```
ATGAAGCTCTTCGTGCTCATAGTATGGGCACTGTTGCTATTGTCTCATGG

ATCTGGAAGCGTCATTTGTGCTGTCCTCCATGGGAACGATACAGATATGC

TGTCGCTTCTTGATTTCAAGCGCGCAATCACCGACGATCCAAAAGGGCTC

TTGAGCTCATGGAACACCAGTGTTCACTTCTGCAACTGGCAGGGTGTGAA

GTGCAGCCTCGAAGAACATGAGCGCGTTGCAGAGCTGGACCTGTCGGAGC

AGAGTTTTGTCGGGGAAATCTCTCCTTCCCTCGGAAACATGTCATATCTT

ACTTATCTTAACCTTTCCAGAAGCAAGTTCTCTGGTCAGATACCACATCT

TGGCCGGCTGCAAGAACTGGAGTTTCTTGACCTGAGTCACAACTCGCTAC

AAGGGATTATTCCAGTGACGCTCGCAAACTGCTCCAACTTGAGGGTGTTA

GACCTCTCAAGAAACTTATTGGTGGGTGAAATTCCAGCAGAAATATCCCT

ACTCTCCAATCTGACACGCTTGTGGCTTTCTTATAATGATCTTACCGGGG

TCATTCCACCAGGCCTTGGCAATATCACTTCTCTAGAACATATTATTCTG

ATGTATAACCGGTTAGAGGGAGGCATTCCTGATGAGTTTGGGAAGTTGTC

CAAAATGTCAAACTTACTCCTTGGTGAAAACAAGCTATCAGGTAGAGTCC

CAGAGGCCATTTTTAATATGTCTCTGCTAAATCAAATGGCACTGGAGTTG

AATATGCTAGTTGGTACTCTACCATCTAACATGGGTGATGCTCTCCCTAA

CCTCCGACTTCTTACGTTGGGTGGTAACATGCTGGAAGGTCTTATCCCAG

ACTCATTAGGCAATGCATCCGAGCTACAACTGATAAACTTAGCATATAAT

CATGGGTTTAGAGGACGGGTCCCACCTTCTCTTGGTAAACTCCCGAAGCT

CCGTAAGCTAGGTCTTGACACAAACAGTCTTGAAGCAAATGACAGTTGGG

GCTGGGAATTCTTGGATGCATTGAGCAACTGCACTTCTCTAGAGATGCTT

TCACTCTATGCAAATCGGCTACAAGGAAACTTGCCAAATTCTGTTGGCAA

CCTTTCGTCTAATGTTAACAACCTCGTGTTTGGTAGGAATATGCTATATG

GATTAGTTCCATCAAGCATAGGAAATCTCCATAGACTAACTAAGCTAGGA

CTGGAGGAGAACAAGTTGACTGGTCCGATTGATGGATGGATTGGAAATCT

TGCTAATTTACAAGGTTTATATCTTCAACAGAACAATTTCACTGGACAGA

TTCCAACTTCCATTGGCAATAACTCCAAGCTGTCAGAACTGTTTCTGGCA

AATAATCAATTCCACGGTCCCATACCATCAAGTTTAGAAAACCTTCAGCA

ACTCTTGTATTTAGACCTCAGCTATAACAATCTTCAAGAAAATATACCCA

AAGAGGTTTTAGTGTAGCACAATTGCCCAATGTGCGTTATCCCACAAC

AGCCTAGAAGGCCAAATTCCTCACATCAGTAATCTTCAACAACTCAACTA

TCTAGATCTTTCATCCAACAAGCTTACTGGGGAAATTCCACCTACTTTGC

GCACATGCCAGCAATTGCAAGCCATCAAAATGGACCGGAACTTTCTCTCG
```

```
GGAAGCATTCCCATATTTCTAGGCAGTCTGAACAGCTTGATCGAGCTCAG
CCTTTCACATAACAATCTCTCAGGCTCTATCCCAATTGCTCTAAGCAAAC
TGCAACTTCTCACCCAGTTGGATCTATCCGACAATCATCTTGAAGGAGAA
GTACCAGTAGAAGGAATATTCAAAAATACAACAGCCATTTCCCTTAAAGG
CAATTGGCGGCTTTGTGGAGGTGTACTGGACCTACATATGCCTTCATGCC
CCGCTGCTTCTCAGAGAAGATCTAGATGGCAACACTATTTGGTCAGAGTA
TTGGTCCCTATATTAGGCATCTTGTTACTCATATTAGTAGTCTGCTTAAC
CCTTCTCAGAAAGAGGATGCTGAGGATGCAGTTATCGCTGCCTTCTTCCG
ATGAGCAATTCCCTAAAGTATCTTATAAGGATCTAGCACAGGCTACTGGG
AACTTCACAGAGTCAAACTTGATTGGGAGAGGAAGCTGCGGTTCAGTGTA
CAGAGCAAAACTAAACCCAAAACAGATGCTTGTGGCAGTGAAAGTTTTTG
ACCTTGACATGCAAGGTGCGGATAAAAGTTTCATCTCAGAATGTAAAGCG
CTCAGAAATATTCGGCATCGGAATCTTCTTCCAATTCTAACTGCATGCTC
AACAATTGATAATCGAGGCAGGGATTTCAAAGCTCTAGTCTACCAGTTCA
TGCCCAATGGCAACTTGGACACTTGGCTGCACCCGACAGGAGATGAAAAA
GGCCCAAAACAATTGGACCTCTCTCAAAGAATGAAAATAGCTCTTGATAT
AGCCGATGCATTGCAATATATACACCATGACTGTGAGAGCCCTATTGTTC
ACTGTGACTTGAAGCCCAGCAACATCCTCCTAGATTATGATATGACAGCT
CGTTTGGGGGACTTCGGCATCGCAAGGTTCTACATCAAATCCAAGTCAGC
AGCAGCTGGGGGTTTGAGTTCAATGGGTACAATGACTCTGAAGGGCACGA
TTGGATATATCGCTCCAGAGTATGCAGGAGGCAGCTACCTATCCACCTCC
GGAGACGTGTACAGTTTTGGGATAGTACTGCTGGAGATGCTGACAGGAAG
AAGGCCGACCGACCCTATGTTCTGCGAGGGGCTTGACATCGTGAACTTTG
TCAGGAGGAACTTTCCGGATCAGATACTTCATATCCTTGACGCTTCTCTC
CGGGAAGAATGCCAAGACTGCTCCCAGGATAATCTGGAAGAAGAGAACGA
AGTCCACCGGTGCCTGTTGTCCTTGCTGAAAGTGGCACTTTCTTGCGCGA
GCCAGGATCCTAACGAGCGAATCAACATGAGAGAAGCAGCTACTGAACTG
CACGCGATCGACGCGTCGTTTGTGTCTTGA
```

SEQUENCE ID NO. 9 is as follows:
TRIAE_CS42_6AL_TGACv1_471249_AA1505410.2

```
ATGCGTTCTCCCAAGCAACCGGCGAAGCTCGTCATGCTTTTACTGTTGGC
ACTGCTGCTGCTCTGTAACGGAGTTGGCAACGTCCATTGCACAAGGATCC
ACGAGAACAGCGTCGATCTGCACGCGCTGCTAGACTTCAAGCAGGGCATC
AACAATCCTCAGGAAGCCTTGAGCAATTGGAGCACCACCACCCACTTCTG
TCGATGGAATGGTGTCATCTGCACCACGACACGGCCGTTTCGTGTCTTGT
CGCTTATACTCACTGAATTGGACTTAGCAGGCCAAATCAGCTCCTCTCTT
GGAAACTTAACCTTCCTTGAAACGCTTGACCTTTCATATAATAACTTCGT
TGGTCCCTTACCTGTCCTTGGCCATCTCCAACAACTCCAGACACTTTCTC
TGAACAACAACAGGTTAAATGGGATGATTCCTGATTCACTTACCAACTGT
TCCAGCTTGGACACTTTAGATCTCTCTGTAAACTTCCTAGTGGGTCCAAT
```

```
TCCTCCGAATTTGGACTTGCTTTCAAATCTTACTTACTTAGATCTCTCTA
GTAACATGCTAGTGGGTCAAATTCCTCCGAAACTAGTTTCTCTATCAAAG
CTGGTCACATTAGATCTCTCCCATAACATGCTAGTTGGTCCAATTCCTCC
GAATCTGGACTTGCTTTCAAATCTGACTTACTTAGATCTATCTAGAAACT
TGCTAGTGGGTCAAATTCCTCTGAAAATAGTTTCTCTACCAAAGCTGGCC
ACATTAGATCTCTCTACTAACATGCTAGTGGGTCAAATTCCTCCGAAGTT
AGGCTTTGTTTCAAGTCTAGAATACTTCAGTTTGGCATCAAACAAACTCG
AGGGAAGCATTCCTAATGAGCTTGGGCAATTGCCTAGTTTACAATACTTG
CTCCTGGGAGAAAATAATCTTTCAGGTGAATTCCCGCATTCCATCTTGAA
CAGAAACCTTTCTGTTTCTCTCCTATATCTAGGCTTGGAGCTGAATATGC
TAGGCAAGGTATTGCCACCTAATATAGGTGACCTTCGGGGTCTCGTACAC
CTTACAATGAGTGGCAACATGTTTGAAGGGCACATCCCAGCTTCCCTAGG
CAACGCCACAGGATTAAAAGTAATAGACTTATCAGCTAACAATTTCACCG
GGCAAATTCCTAACTCTTTTGGAAAGCTCTCAAATCTGACTAATCTAAAC
CTTCAGTATAACCAGCTTGAAACAAGGGACTGGGAATTCTTCAATGCATT
GACGAACTGTCGTTCTCTAAACTCACTCTCACTGGGTTTCAACCAGCTGC
AGGGATCTATACCGCAGTCTGTCGGTAACCTATCCAACAAACTAGAAAAA
CTTACTTTGACTCAAAATAGCTTATCAGGACAAGTACCCCAGAGCATCGG
CAACCTTAGTGCATTAAATCAACTGGCACTAGGTATAAACAACTTAAGCG
GCACAATAGAAGGATGGATTGGAAACCTAAAAGGCCTTGAAGGATTAACT
CTCCGCTCAAACCGCTTCACCGGCCAAATCCCACCCTCTATTAGCAATCT
TACTCGGTTGATAAATCTTTATCTCTATGATAATCAATTCGAGGGCCTCA
TACCCCCCAGCCTGGGAAACCTCCCACTCACACAGCTAGTCCTTAGCTCT
AACAATCTTTACGGGTACATACCACCCAGCTTAGGAAGCCTCCAACAGCT
TACGTCATTGAATCTTAGCCACAATAATCTCCAAGGTGAGATACCTCAGA
TTAGCGCCCTTAAGCAACTCACTACTTTAGATCTTTCTTCAAATAAGCTC
ACAGGGAGTATTCCAGATTCTTTGGGCCAATGTTACGGCTTACGGAGTCT
GCAAATGGACCAAAACTTTCTGTCAGGAAACATCCCAATAGCCTTTGGCA
AACTGTTGTCTCTGAGTATACTAAATCTATCACACAACAACTTGTCAGGC
ACCATCCCGTCGGCTCTAAACAAACTAGAGTTCCTAAACCATCTTGACCT
TTCATATAATCATCTTGAAGGAAAAATACCCAGAGATGGAGCATTCGAAA
ATGCTACGGCTGTTTCACTTGAGAACAATTGGGGGCTCTGCGGAGGCGCC
GTGGATCTTCACATGGCTTCATGCACAACCATTTCCAAGAAAGAAGAGGA
GAGACGATACCGTTTGATTAAAGTATTGATTCCAATATTTGGATTCTTGT
CACTGGTACTGTTGATCTACTTTGTACTCCTTGAGAAGAAGATGCGAAGG
GCAAATGATACATCAGCTTCATTAGGCGAGAATTTTCTGAAGGTTTCTTA
TGCGGATCTAGCACAAGCCACATCAAACTTCTCTGAATCTAACCTGGTTG
GGAGAGGAGGTTATGGCTCTGTCTATCGCGGAAAGTTAAAGGATTCTAAG
GTGGAAGTGGCCGTCAAGGTTTTTGATCTTGAAATGCATGGAGCTGAGAG
AAGCTTTCTGAAAGAATGCGAGGCACTGCGAAGCATTCAGCATAGAAATC
```

-continued

```
TTCTTCCCATCATAACTGCTTGCTCGACGGTAGACAATACAGGCAATGTT

TTCAAAGCTTTAGTTTATGAGTTCATGCCTAATGGGAACCTAGACACATG

GCTGCATCACAGAGAGGACGGGAAGGCTCATAAACATTTAAGCTTAGCTC

AAAGATTAGACATAGCTGTTAACATGGCTGACGCACTGGATTATCTACAC

CATGACTGCGGAAGACCCACCATCCATTGTGACCTGAAGCCCAGCAACAT

TCTTCTGGATGATGATATGACCGCTCTTTTAGGAGACTTTGGTATTGCAA

GTTTTTACCAAGATTCCAGGTCAACATCACCTGGTTCAGTGAGTTCATCA

TCAGTCGGTATGAAGGGTACTATTGGATATATTGGTCCAGAGTACGCGGG

AGGTGGCCGCCATGCATCAACTTGCGGAGATGTTTACGGTTTTGGGATAA

TACTGCTGGAAATGATGACCGGAAAAAGACCAACAGATCCATTGTTCAAG

GATGGAGTTAGCATTGTCGACTTTGTGGAGAGCAACTTTCCACATGAAAT

AGTTCGTGTCATTGATGCTAATCTCAGTGAAGAATGCAAGGACATTGCTC

AATCAAAGAAGATTTCAGAAAATTCAGTTCATCAATGTTTGCTATCTGTG

CTGCAACTAGCACTTTCCTGTACGCACCCAGTACCAGGCGAAAGAATGAA

TATGAAAGTGGTGGCCAGCAAAATGCATGCAATTAAAACATCCTATGGGG

GCTGCAATGCGCAAGAGTGA
```

SEQUENCE ID NO. 10 is as follows:
TRIAE_CS42_6 BS_TGACv1_514259_AA1657570.3

```
ATGATGGATCTCCACATGAAGTTTCTCCTGGCCTCCCTCAGCTGTGTACT

TCTGATACAAGGAGCTTTCTGTGGGGGGACTGGAGCGACAAGCTGGACTT

GTGTGTGCACCGCTCATCCACTTGGCGAAGCAAACTCCAATAGCAGCCTG

TCATCCAGTTGCGACTCCTCGTGCCATTGCATACGAGATGAAAACGGCGG

CACAGGGTCATGGAACTGCTCGTGCCGCTCCGACAAGGACCTTCAGGAAG

AAGAACACGCTGTGGTGCACAGTGGGAGTTGCTTCACTTCCTGTAACTGC

ACATCTGGAAGTTCTGAACAAGAGAGGAAGCATTTCTCTAGCAAAACAGT

CATTGCTACACTCCTGGTATGTGTGGTTCTCACCACTGTTGCTTTCGTCG

GAACAACGGCGTACTACTTCCGCCGCAAGGACGCACTCTCCCCGCGTTCC

CGGATGCACTCTTTCGACAAGTACGCGAGCTGGAGCAGCAGATCGAACCT

CGTTAGCCATCGATCTTCTCCCCTTACCCAACTGAAACCCAAACCCGGGC

TCAGTGTCATCAAAGGGTTTTTGTGTAGCTGCCCACTCGTCTCCCGGAGC

GAAGACGGCCCATTCCCGGCGTGGTTCTCCGGTTCTCCTACGTCGAGCT

GGAGCAGGCAACAGGGAAATTTTCCGACGAACACCTCATCGGCGTCGGCG

GGACCAGCAAGGTGTACCGTGGACAGCTCGCCGACGGCAAAGTCGTCGCC

GTGAAGAAGCTTCGGCCCCTCGGTGGTGCGGACGAAGACTATGAGTTCCT

GTCAGAGATCGAGCTGCTGTCACGGCTGAACCACTGCCATGTGGTGCCAT

TGCTGGGGTACTGCTCGGAGCGGCAGGGGCGGCAGCTGGAGCGGCTGCTG

GTGTTCGAGTGCATGACCAACGGCAACCTGCGGGAGTGCCTGGACGACCT

CAACAGGAAGCCCATGGACTGGGCGACGCGCGTCGGCGTGGCGCTGGGCG

CCGCGAGGGGCCTCGAGTACCTCCACGAGGCGGCGGCGCCGCGCATCCTC

CACCGCGACATCAAGTCCACCAACATCCTGCTCGACGACCGGTTCAGGGC
```

-continued

```
CCGGATCACGGACCTGGGCATGGCCAAGTGCCTGATGAACGACGGCGTGA

CGAGCTGCTCTAGCTCGCCGGCGCGGATGCTGGGCACCTTCGGGTACTTC

GCCCCCGAGTACGCCATCGTCGGCAAGGCGTCGCTCAAGTCGGACGTCTT

CAGCTTCGGCGTGGTGGTGCTCGAGCTCATCACCGGCCGGCAGCCGGTGC

ACAAGAGAGGCGGCGCCGGCGCCGGTGGCGGCGGCACGGACGAGAGCCTG

GTGATGTGGGCGACGTCGCGGCTCCGGGACAGCAGGTTGGTGGTGGCGGA

GCTGCCGGACCCGGCGCTGAAGGGCGCGTTCCCGCCCGAGGAAATGCAGA

TCATGGCGCACCTGGCCAGAGAGTGCCTGCAGTGGGACCCCGAGGCCAGG

CCCACCATGACCGAGGTCGTTCAGATCCTCTCCACCATCGCGCCCCTTGC

CGACAAGCGCCGTCGCCACCACCTGCCCGCCGCCGCCGCCGCCTTCGCCC

CGGGCTTCCGTGCCGAGAAGCCGCAGGAATGCTCAGTGTGGCAGGACGGC

GACGACGGCCGTCGCCGTGATCACCTGCACGGGGGGAACGGTAGCAATGC

AAAGGGCACCGTCTTGTCGGGCGAGGTCGCGGTTAACGTCGGCACGCCGG

CGGCGATGGGCCGGAGCTGGCGGTCGGCGGAGCAGGAGGAGGTGGACCTG

ACGGAGCCGCGGCTGGAGACGTTCACGCAGCCGACAACGACGGCGAGCCT

CTTCAGGTGA
```

A variant of SEQ ID NO. 2 is also provided.

Typically, the variant has at least about 30%, 40%, 50%, 60% or 70% sequence identity with SEQUENCE ID NO. 2.

In a preferred embodiment, the variant has at least about 70% sequence identity with SEQUENCE ID NO. 2. Preferably, the variant comprises (or consists of) a sequence having at least about 70, 75, 76, 77, 78, 79, 80, 81, 82, 83, 84, 85, 86, 87, 88, 89, 90, 91, 92, 93, 94, 95, 96, 97, 98 or 99% sequence identity with SEQUENCE ID NO. 2. Typically, the variant has from about 74% to about 89% sequence identity with SEQUENCE ID NO. 2. Typically, the variant is a functional variant.

95, 96, 97, 98 or 99% sequence identity with SEQUENCE ID NO. 2. Typically, the variant has from about 74% to about 89% sequence identity with SEQUENCE ID NO. 2. Typically, the variant is a functional variant.

In an embodiment, the variant may have a sequence comprising (or consisting of) SEQUENCE ID NO. 11, SEQUENCE ID NO. 12 or SEQUENCE ID NO. 13.

SEQUENCE ID NO. 11 is as follows:

```
MSDQSVKLNMLLLLAFLLLSYGAGNARCSTVHANITDILSLLRFKRSTHD

PTGSLRNWNRSIHYCKWNGVSCSLLNPGRVAALDLPGQNLSGQVNPSLGN

ITFLKRLNLSSNGFSGQLPPLSQLHELTLLDMSSNLFQGIIPDSLTQFSN

LQLLNLSYNGFSGQLPPLNQLPELVVLDLKSNLFQGIIPDSLTNCSNLTF

VDLSRNMLEGSIPAKIGSLYNLMNLDLSRNKLTGVIPPTISNATKLQFLI

LQENELEGSIPSELGQLSNMIGFTVGSNRLSGQIPASIFNLTLLRVLGLY

ANRLQMAALPLDIGHTLPNLQNITLGQNMLEGPIPASLGNISSLQLIELS

NNSFTGEIPSFGKLQKLVYLNLADNKLESSDSQRWESLYGLTNCSHLKSL

RFKNNQLKGVIPNSVGKLSPKLELLHLGGNNLSGIVPSSIGNLDGLIDLD

LSTNSFNGTIEGWVGSLKKLQSLDLHGNNFVGAIPPSFGNLTELTYLYLA

KNEFEGTIPPILGKLKRLSAMDLSYNNLQGDIPPELSGLTQLRTLNLSSN
```

-continued

RLTGEIPVDLSQCQDLVTIQMDHNNLTGDIPTTFGDLMSLNMLSLSYNDL

SGAIPVSLQHVSKLDLSHNHLQGEIPPEGVFRNASAVSLAGNSELCGGVS

ELHMPPCPVASQRTKIRYYLIRVLIPLFGFMSLLLLVYFLVLERKMRRTR

YESQAPLGEHFPKVSYNDLVEATKNFSESNLLGKGSYGTVYKGNLVQHKL

EVAVKVFNLEMQGAERSFMPECEALRSVQHRNLVSIITACSTVDSDGRAF

RALIYEFMPKGNLDTCLHHKGDGKADKHLTLTQRIGIAVNIADALDYLHN

DSENPIIHCDLKPSNILLDEDMVAHLGDFGIARIFLDSGLRPASSTSSIG

VKGTIGYIPPEYGGGGRISTSGDVYSFGIVLLEMLTGKRPTDPMFMDGLD

IVNFVGNKFPHQIHEVIDIYLKGECESEDSVHQCLVSLLQVAVSCTHSIP

GERANIRDTASKLQEIKASYLGRKAKINPSV

SEQUENCE ID NO. 12 is as follows:

MSDQSVKLNMLLLLAFLLLSYGAGNARCSTVHANITDILSLLRFKRSTHD

PTGSLRNWNRSIHYCKWNGVSCSLLNPGRVAALDLPGQNLSGQVNPSLGN

ITFLKRLNLSSNGFSGQLPDASQHELLLIPRDNPRFTHTIFEPTAPEFVL

QWLLRPVTSSEPASRAGGSQLEIQFIPRDNPRLTHKLFEPHVCGSFKKHA

RRLNPGENRFALQSNEFRPFNEMTHRGHTTNHQPMPPSYNFSFFKKMHLE

GKHTQLAWTIVQHDSALLVGSNKALRSNAQHAIFKSYFGSKCLGWYANKT

TKWRALPIRIGPNPPLISKKLTLGPKKAMKVLSQRRSVTFQACNLQSYPI

TVSLEKFLVSESYRNLYTYTLRTISWSQVTAKDGNLYMDQQTAVIHNRSD

SRIISQKESYQIRSVNCPLNLNFYIWGGNNLSGIVPSSSGNLDGLIDLDL

STNSFNGTIEGWVGSLKKLQSLDLHGNNFVGAIPPSFGNLTELTYLYLAK

NEFEGTIPPILGKLKRLSAMDLSYNNLQGDIPPELSGLTQLRTLNLSSNR

LTGEIPVDLSQCQDLVTIQMDHNNLTGDIPTTFGDLMSLNMLSLSYNDLS

GAIPVSLQHVSKLDLSHNHLQGEIPPEGVFRNASAVSLAGNSELCGGVSE

LHMPPCPVASQRTKIRYYLIRVLIPLFGFMSLLLLVYFLVLERKMRRTRY

ESQAPLGEHFPKVSYNDLVEATKNFSESNLLGKGSYGTVYKGNLVQHKLE

VAVKVFNLEMQGAERSFMPECEALRSVQHRNLVSIITACSTVDSDGRAFR

ALIYEFMPKGNLDTCLHHKGDGKADKHLTLTQRIGIAVNIADALDYLHND

SENPIIHCDLKPSNILLDEDMVAHLGDFGIARIFLDSGLRPASSTSSIGV

KGTIGYIPPEYGGGGRISTSGDVYSFGIVLLEMLTGKRPTDPMFMDGLDI

VNFVGNKFPHQIHEVIDIYLKGECESEDSVHQCLVSLLQVAVSCTHSIPG

ERANIRDTASKLQKKVVNCPL

SEQUENCE ID NO. 13 is as follows:

MSDQSVKLNMLLLLAFLLLSYGAGNARCSTVHANITDILSLLRFKRSTHD

PTGSLRNWNRSIHYCKWNGVSCSLLNPGRVAALDLPGQNLSGQVNPSLGN

ITFLKRLNLSSNGFSGQLPPLSQLHELTLLDMSSNLFQGIIPDSLTQFSN

LQLLNLSYNGFSGQLPPLNQLPELVVLDLKSNLFQGIIPDSLTNCSNLTF

VDLSRNMLEGSIPAKIGSLYNLMNLDLSRNKLTGVIPPTISNATKLQFLI

LQENELEGSIPSELGQLSNMIGFTVGSNRLSGQIPASIFNLTLLRVLGLY

ANRLQMAALPLDIGHTLPNLQNITLGQNMLEGPIPASLGNISSLQLIELS

NNSFTGEIPSFGKLQKLVYLNLADNKLESSDSQRWESLYGLTNCSHLKSL

RFKNNQLKGVIPNSVGKLSPKLELLHLGGNNLSGIVPSSIGNLDGLIDLD

LSTNSFNGTIEGWVGSLKKLQSLDLHGNNFVGAIPPSFGNLTELTYLYLA

KNEFEGTIPPILGKLKRLSAMDLSYNNLQGDIPPELSGLTQLRTLNLSSN

RLTGEIPVDLSQCQDLVTIQMDHNNLTGDIPTTFGDLMSLNMLSLSYNDL

SGAIPVSLQHVSKLDLSHNHLQGEIPPEGVFRNASAVSLAGNSELCGGVS

ELHMPPCPVASQRTKIRYYLIRVLIPLFGFMSLLLLVYFLVLERKMRRTR

YESQAPLGEHFPKVSYNDLVEATKNFSESNLLGKGSYGTVYKGNLVQHKL

EVAVKVFNLEMQGAERSFMPECEALRSVQHRNLVSIITACSTVDSDGRAF

RALIYEFMPKGNLDTCLHHKGDGKADKHLTLTQRIGIAVNIADALDYLHN

DSENPIIHCDLKPSNILLDEDMVAHLGDFGIARIFLDSGLRPASSTSSIG

VKGTIGYIPPEYGGGGRISTSGDVYSFGIVLLEMLTGKRPTDPMFMDGLD

IVNFVGNKFPHQIHEVIDIYLKGECESEDSVHQCLVSLLQVAVSCTHSIP

GERANIRDTASKLQEIKASYLGRKAKINPSV

In an embodiment of the invention, a fragment of SEQUENCE ID NO.1 is provided. The fragment is a functional fragment of SEQUENCE ID NO. 1. In an embodiment, the fragment has from 10 to 3000 contiguous nucleotides preferably about 100, 250, 500, 750, 1000, 1250, 1500, 1750, 2000, 2250, 2500 or 2750 nucleotides.

In an embodiment of the invention, a fragment of SEQUENCE ID NO.2 is provided. The fragment is a functional fragment of SEQUENCE ID NO. 2. In an embodiment, the fragment has from about 10 to 1000 contiguous amino acids, preferably about 50, 100, 5 200, 300, 400, 500, 600, 700, 800, or 900 amino acids.

The current invention provides a construct comprising a nucleotide sequence of SEQUENCE ID NO. 1 or a variant thereof or fragment described herein.

The construct may be an expression vector. The vector may comprise regulatory machinery, for example promoters, terminators, and/or enhancers. The nucleotide may be under the control of a promotor region. The promotor may be a constitutive plant cell specific promotor. It will be appreciated that any suitable plant cell specific promotor known in the art may be used. The promotor may be such that multiple copies of TaLRRK-6D are produced. In an embodiment, the vector is a virus, such as a bacteriophage and comprises, in addition to the nucleic acid sequence of the invention, nucleic acid sequences for replication of the bacteriophage, such as structural proteins, promoters, transcription activators and the like.

In an embodiment of the invention, the construct of the invention and described herein may be used to transform plant host cells to produce a recombinant cell in order to express TaLRRK-6D or synthesize the protein. This imparts or enhances FHB resistance in the plant.

In a further embodiment, a recombinant host cell comprising a construct as described herein is also provided by the current invention. The host cell may be any biological plant cell which can be cultured in medium and used for the expression of a recombinant gene.

The invention also provides a transformation platform comprising a recombinant construct of the invention. Typically, the transformation platform comprises a bacterium capable of mediating cellular transformation.

The invention also provides plant material genetically transformed or modified with a nucleotide, recombinant construct or transformation platform of the invention. In an embodiment, the transformed plant material comprises a transformed cell capable of overexpression of TaLRRK-6D or a variant thereof. In other words, the host cell overexpresses TaLRRK-6D or a variant thereof compared to unmodified host cell.

The plant material may be a transgenic plant. The transgenic plant is resistant or has enhanced resistance (compared to a non-transgenic plant) to FHB.

Typically, the plant material comprises a plant cell carrying a transgene, in which the transgene comprises the nucleotide of the invention.

In the current invention, the plant material is selected from but not limited to a plant cell, plant cell culture, plant tissue, plant, or seed for a plant. It will be understood that any suitable plant material known in the art may be used.

In the current invention, the plant is a cereal. Typically, said cereal is selected from but not limited to the group comprising maize, rice, wheat, barley, sorghum, millet, oats, soybean and rye. Preferably, the cereal is wheat.

The invention also provides a method of genetically transforming a plant material comprising the steps transforming a cell or cells of the plant material with a nucleotide, recombinant construct or transformation platform of the invention. The transformed cell may be capable of overexpression of a nucleotide of the invention. In other words, the host cell overexpresses TaLRRK-6D compared to unmodified host cell.

The invention also provides a method of producing a transgenic plant comprising the steps of transforming a plant material according to a method of the invention as described herein and generating or growing a transformed plant from the transformed cell.

The invention also provides a method of producing a plant material having resistance to FHB disease, the method comprising the steps of transforming a plant material with a construct of the invention or a transformation platform according to the invention, and optionally growing the plant material. Preferably, the recombinant construct comprises SEQUENCE ID NO: 1 or a variant thereof. In this manner, a plant which is resistant to FHB may be produced. Typically, the plant shows reduced or an absence of FHB symptoms when infected with *Fusarium* fungus compared to a non-transgenic plant.

The plant or plant material transformed with the construct or transformation platform of the invention may already express endogenous TaLRRK-6D. This may be at a low level. Host cells are transformed using techniques known in the art such as, but not limited to, electroporation; calcium phosphate base methods; a biolistic technique or by use of a viral vector. After transfection, the nucleotide of the invention is transcribed as necessary and translated. In some embodiments, the synthesized protein is allowed to remain in the host cell and cultures of the recombinant host cell are subsequently used.

The current invention also provides a functional marker for FHB resistance. The marker is the TaLRRK-6D. The marker may be the nucleotide or the peptide of the invention. This provides ways to develop FHB wheat cultivars by marker assisted selection and breeding. A method of determining FHB resistance or a method of selecting FHB wheat cultivar, by detecting or measuring TaLRRK-6D expression levels, and optionally growing the FHB wheat cultivar, is also provided.

In another embodiment, the TaLRRK-6D also functions as a selectable marker gene, wherein the traits displayed by the transformed cell function as a selective marker for the successful incorporation of the transgene. It will be appreciated that incorporation of the transgene may be by any method as described herein. A method of using TaLRRK-6D as a selectable marker is provided. The traits may be those of FHB resistance.

The marker may be the nucleotide sequence of the invention or the amino acid sequence of the invention.

Also provided is plant material genetically transformed according to a method of the invention.

A further aspect of the invention provides an isolated sequence comprising (or consisting of) SEQUENCE ID NO. 1 or a functional variant thereof or a functional fragment thereof.

Preferably, the variant has at least 55% sequence identity with SEQUENCE ID No. 1.

Preferably, the variant has at least 60% or 70% sequence identity with SEQUENCE ID NO. 1.

In a preferred embodiment, the variant has at least about 70%, 75%, 80%, 81%, 82%, 83%, 84%, 85%, 86%, 87%, 88%, 89%, 90%, 91%, 92%, 93%, 94%, 95%, 96%, 97%, 98% or 99% sequence identity with SEQUENCE ID NO. 1, typically between about 91.5% to about 95% sequence identity with SEQUENCE ID NO. 1

A further aspect of the invention provides an isolated peptide comprising (or consisting of) SEQUENCE ID NO. 2 or a functional variant thereof or a functional fragment thereof.

The invention also provides an isolated protein encoded by the nucleotide of the invention or having a sequence of SEQUENCE ID NO. 2 or a functional variant thereof or a functional variant thereof.

Typically, the variant has at least about 30%, 40%, 50%, 60% or 70% sequence identity to SEQUENCE ID NO. 2.

In a preferred embodiment, the variant has at least about 70% sequence identity to SEQUENCE ID NO. 2. Preferably, the variant comprises (or consists of) a sequence having at least about 70%, 75%, 76%, 77%, 78%, 79%, 80%, 81%, 82%, 83%, 84%, 85%, 86%, 87%, 30 88%, 89%, 90%, 91%, 92%, 93%, 94%, 95%, 96%, 97%, 98% or 99% sequence identity with SEQUENCE ID NO. 2. Typically, the variant has between about 74% to 89% sequence identity with SEQUENCE ID NO. 2.

EXAMPLES

Example 1

TaLRRK-6D gene expression in wheat heads
Study Description
To confirm that TaLRRK-6D homologue specifically was responsive to the fungus *Fusarium*, a quantitative RT-PCR assay was used to measure the level of gene expression in wheat heads treated with the fungus.
Strains
The deoxynivalenol producer *Fusarium graminearum* (strain GZ3639) was used in this study.
Method
Spikelets were inoculated with the deoxynivalenol producer *Fusarium graminearum* (strain GZ3639). Expression levels were tested up to 7 days (at day 1, 2, 3, 5 and 7) post fungal inoculation. The effect of the DON-non-producing mutant derivative of GZ3639, namely GZT40, on TaLRRK-6D expression was also analysed. The effect of TaLRRK-6D in wheat heads treated with mycotoxin DON was also analysed.

Results

The results showed that the TaLRRK-6D expression was early induced at 1 day post inoculation (dpi); with a peak of induction at 2 dpi, followed by a return to a basic level. This is illustrated by FIG. 3.

Figure 3:
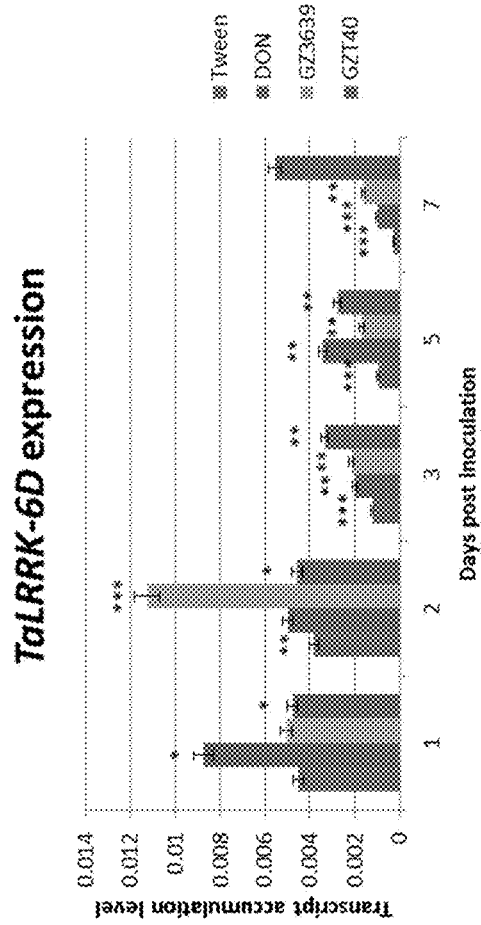
FIG. 3 is a graph of post inoculation expression levels for TaLRRK-6D in wheat heads inoculated with *Fusarium* and treated with mycotoxin DON.

The induction of TaLRRK-6D expression by GZT40 was very low at all the days post inoculation (FIG. 3). The expression results for TaLRRK-6D in wheat heads treated with mycotoxin DON, showed significant increase of TaLRRK-6D transcript accumulation in response to the toxin. This was maximal at 1 dpi, and gradually reduced in the next few days (FIG. 3). From these results, it is evident that TaLRRK-6D is responsive to FHB and it is concluded that TaLRRK-6D is a component of the early host response to *Fusarium* fungi.

Example 2

TaLRRK-6D role in resistance to FHB

Study Description

The virus-induced gene silencing (VIGS) platform was used to validate TaLRRK-6D role in resistance to FHB in two wheat cultivars—the FHB resistant cv. CM82036 and the susceptible cv. Remus.

Strains

Wheat resistant cv. CM82036 and susceptible cv. Remus.

Methodology

Figure 5:
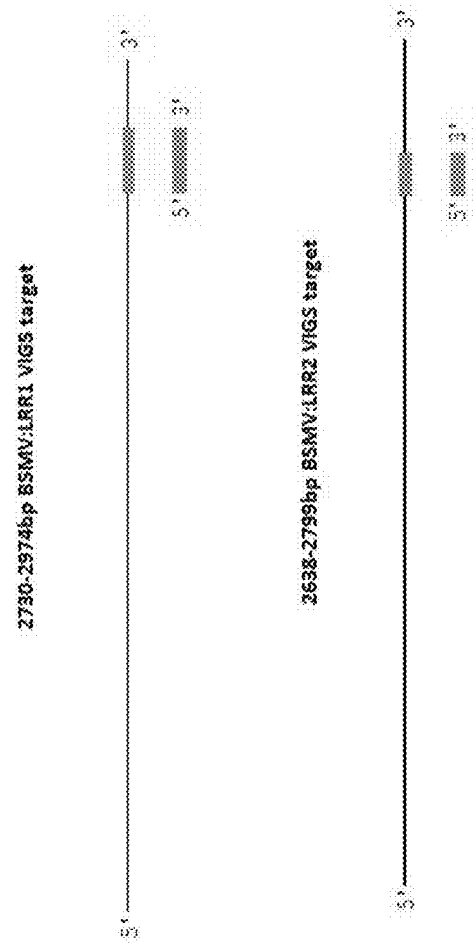
FIG. 5 illustrates the position of the fragments within the mRNA encoding the wheat TaLRRK-6D on wheat chromosomes 6DL targeted for gene silencing and qRT-PCR for virus induced gene silencing (VIGS) studies. Numbers indicate bp positions in the TaLRRK-6D mRNA sequence.
Figure 6:
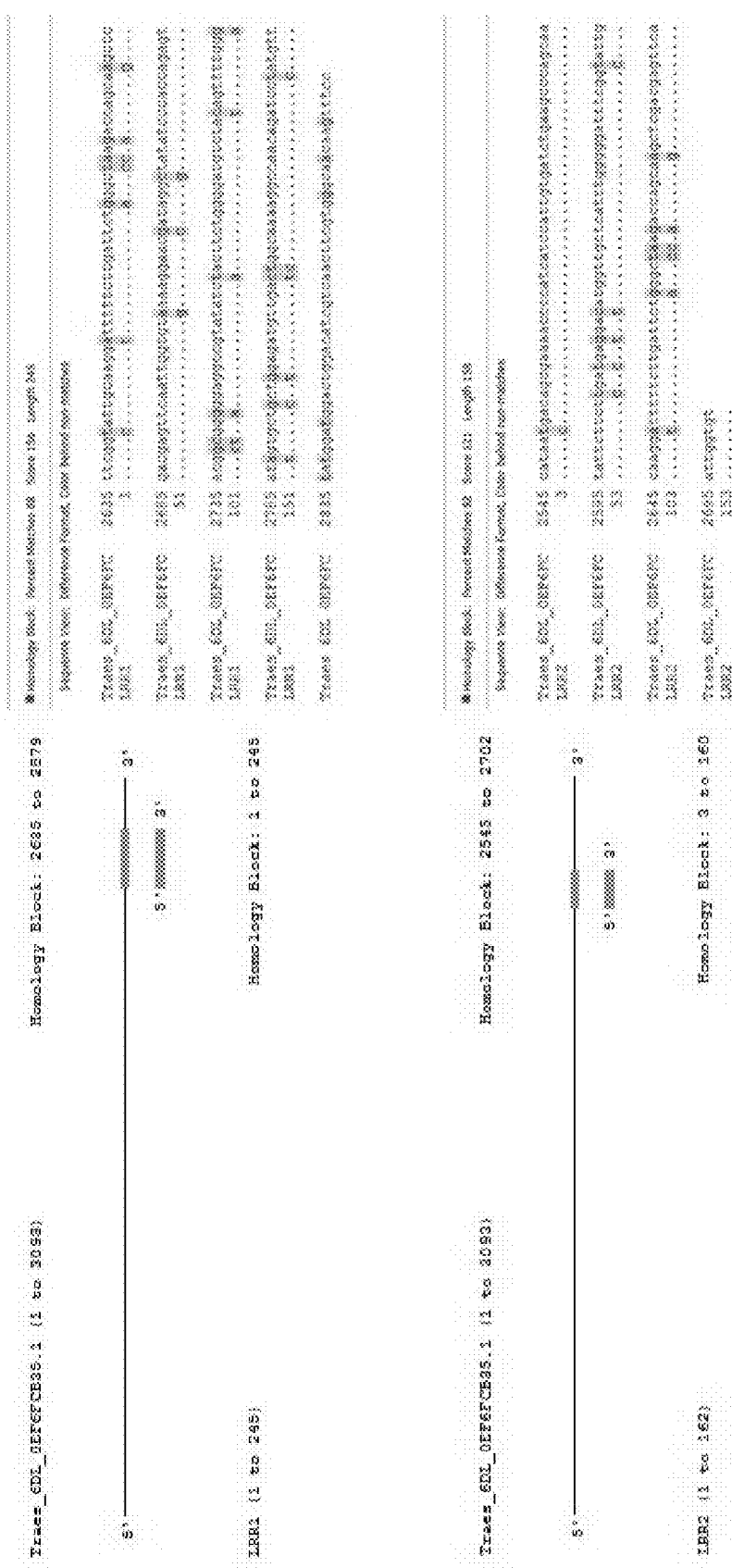
FIG. 6 is a pictorial representation of the two VIGS constructs and specificity to TaLRRK-6D. The two VIGS constructs (BSMV:LRR1 and BSMV:LRR2) were aligned with TaLRRK-6D using clustalW2 multiple alignment in Clonemanager v.9.0 to validate that BSMV:LRR1 and BSMV:LRR2 were specific to silence TaLRRK-6D.

Virus induced gene silencing: Two independent constructs were designed (BSMV:LRR1 and BSMV:LRR2) which target two distinct sequences of the TalRRK-6D gene (FIG. 5). Plants comprising an empty vector (BSMV-00) which serves as a positive control and plants in which no construct was incorporated (negative control) were also included in the experiment. FIG. 6 is a pictorial representation of the two VIGS construct for its specificity to TaLRRK-6D. Constructs were applied to the flag leaves of the wheat cv. CM82036 and cv. Remus before emergence of the primary head. Two weeks later, two central spikelets were treated with FHB (16.9 mM) or mock 0.02% Tween20 treatment at mid anthesis (growth stage Zadoks 65). The phenotypic effect of FHB on plants at 7 and 14 days post-FHB treatment was also analysed by measuring the number of spikelets with FHB symptoms, e.g. discolouration.

Results

Figure 7:
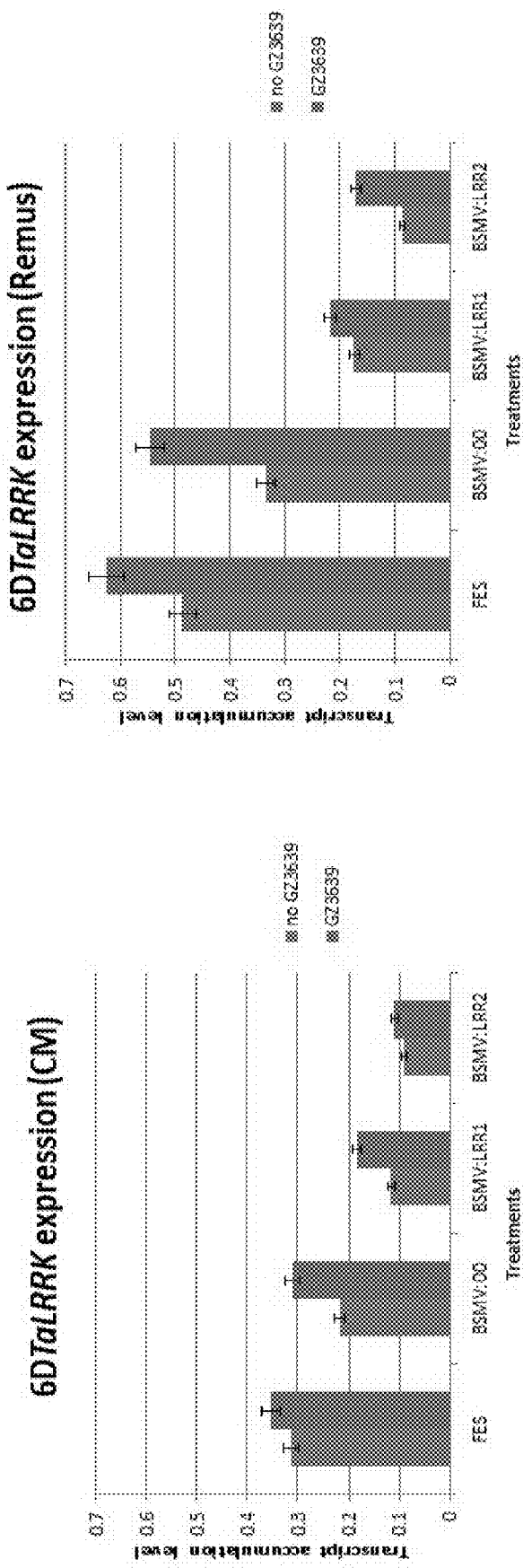
FIG. 7 is a chart illustrating TaLRRK-6D expression in the non-toxin treated plants (mock), whether in the control (BSMV:00) or silenced plants (BSMV:LRR1 and BSMV:LRR2).

At 1 dpi, one spikelet above the one which had been treated was removed and used to measure the expression level of TaLRRK-6D by quantitative RT-PCR. Very low TaLRRK-6D expression was observed in the non-toxin treated plants (mock Tween treated), whether in the controls (FES), (BSMV:00) or silenced plants (BSMV:LRR1 and BSMV:LRR2) (FIG. 7).

Figure 8:
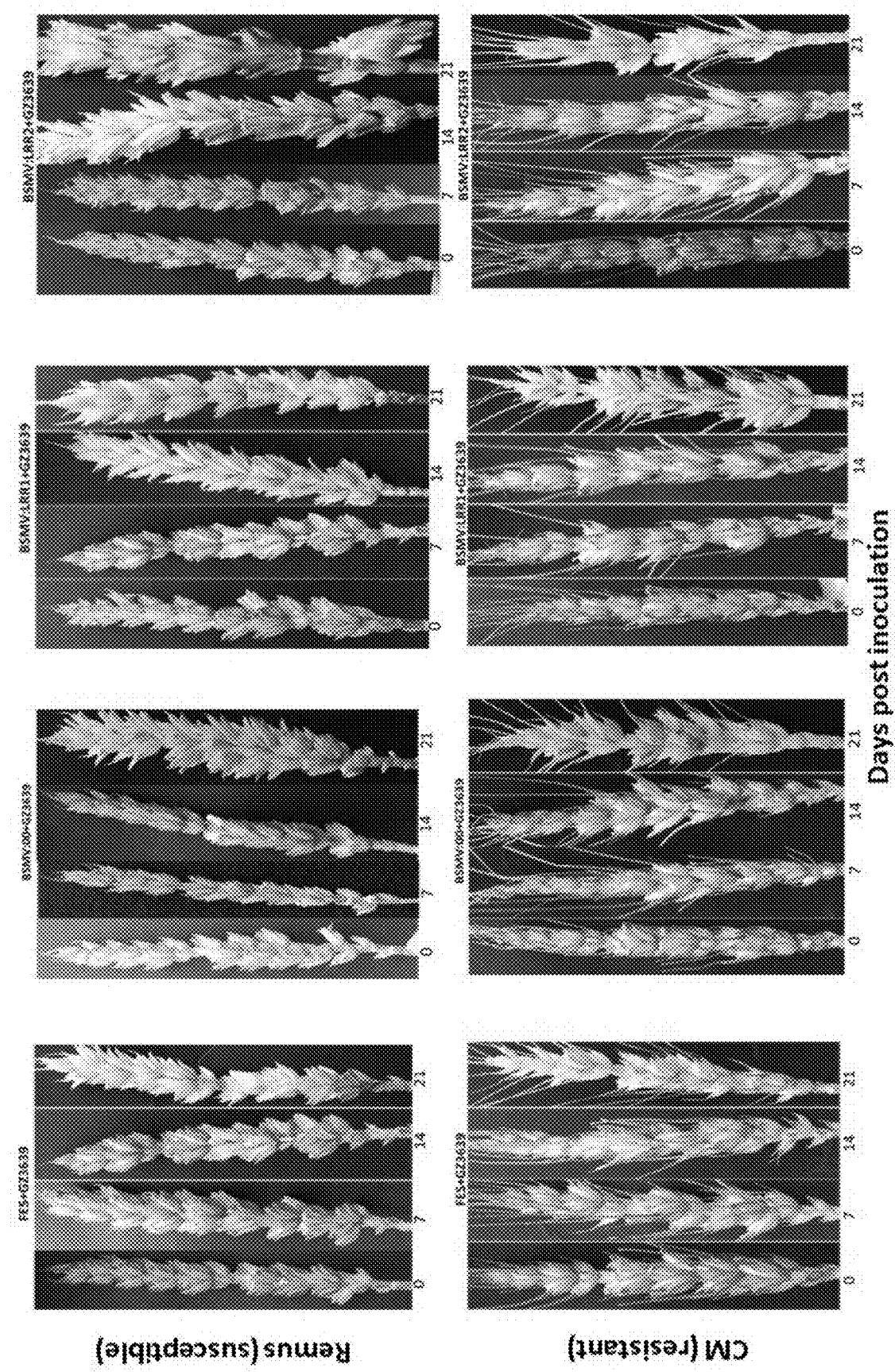
FIG. 8 illustrates FHB symptoms in Remus (susceptible) and CM (resistant) wheat heads 0, 7, 14 and 21 days post inoculation (FHB-treated, BSMV:00-treated plants).

In both cultivars, silencing reduced TaLRR-6D expression for both mock (no GZ3639) and *Fusarium* (GZ3639) treated samples (comparing BSMV:LRR 1 and BSMV:LRR2 versus BSMV:00). Silencing of TaLRRK-6D due to BSMV:LRR1 and BSMV:LRR2 plants treatment increased the FHB severity by 54.5% and 72.7% (as compared to mock and BSMV:00-treated plants) as illustrated in FIG. 8.

Figure 9:
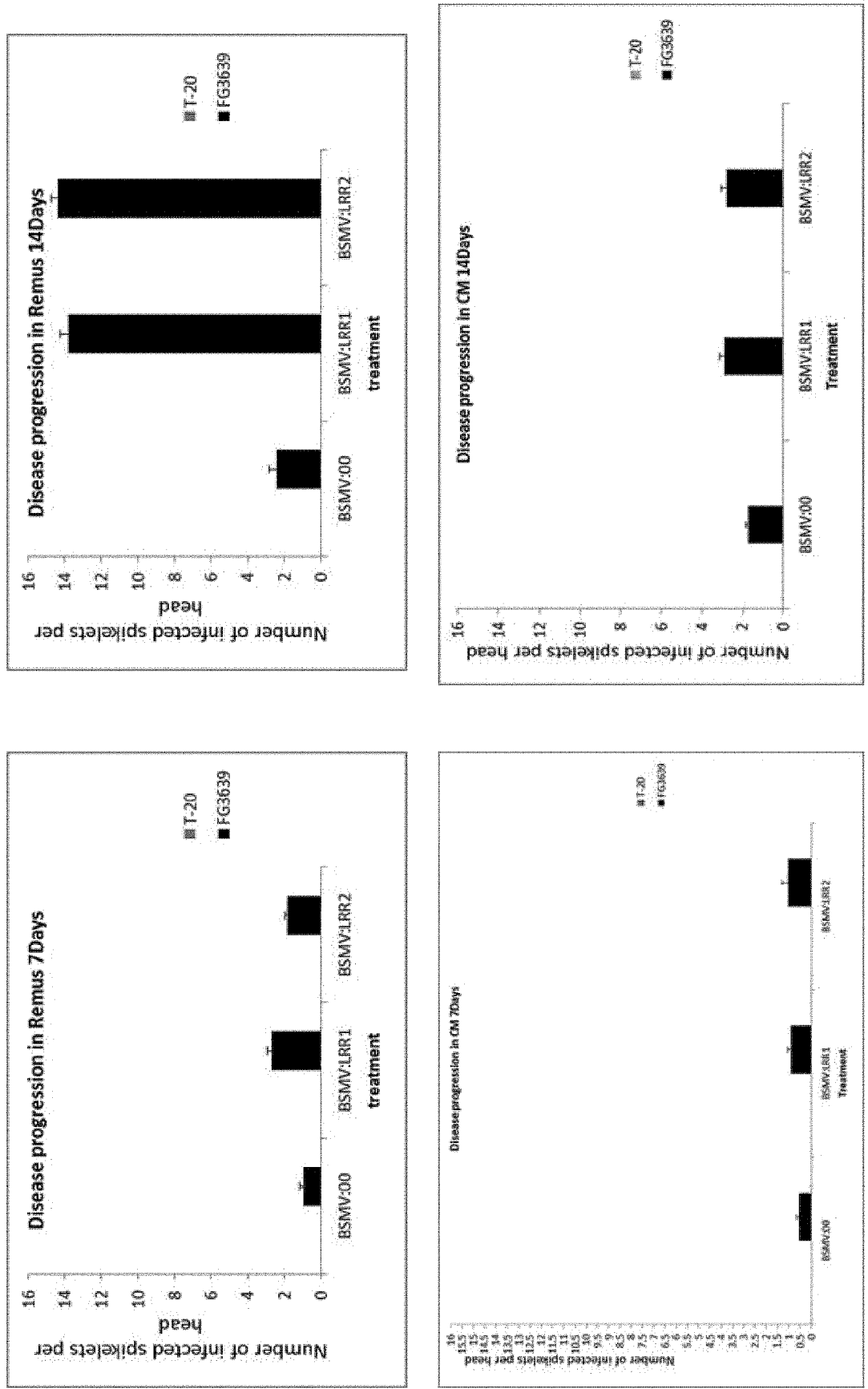
FIG. 9 illustrates FHB induced damage of spikelets in plants treated with BSMV:LRR1 and BSMV:LRR2 and the non-silenced plants BSMV:00.
Figure 10:
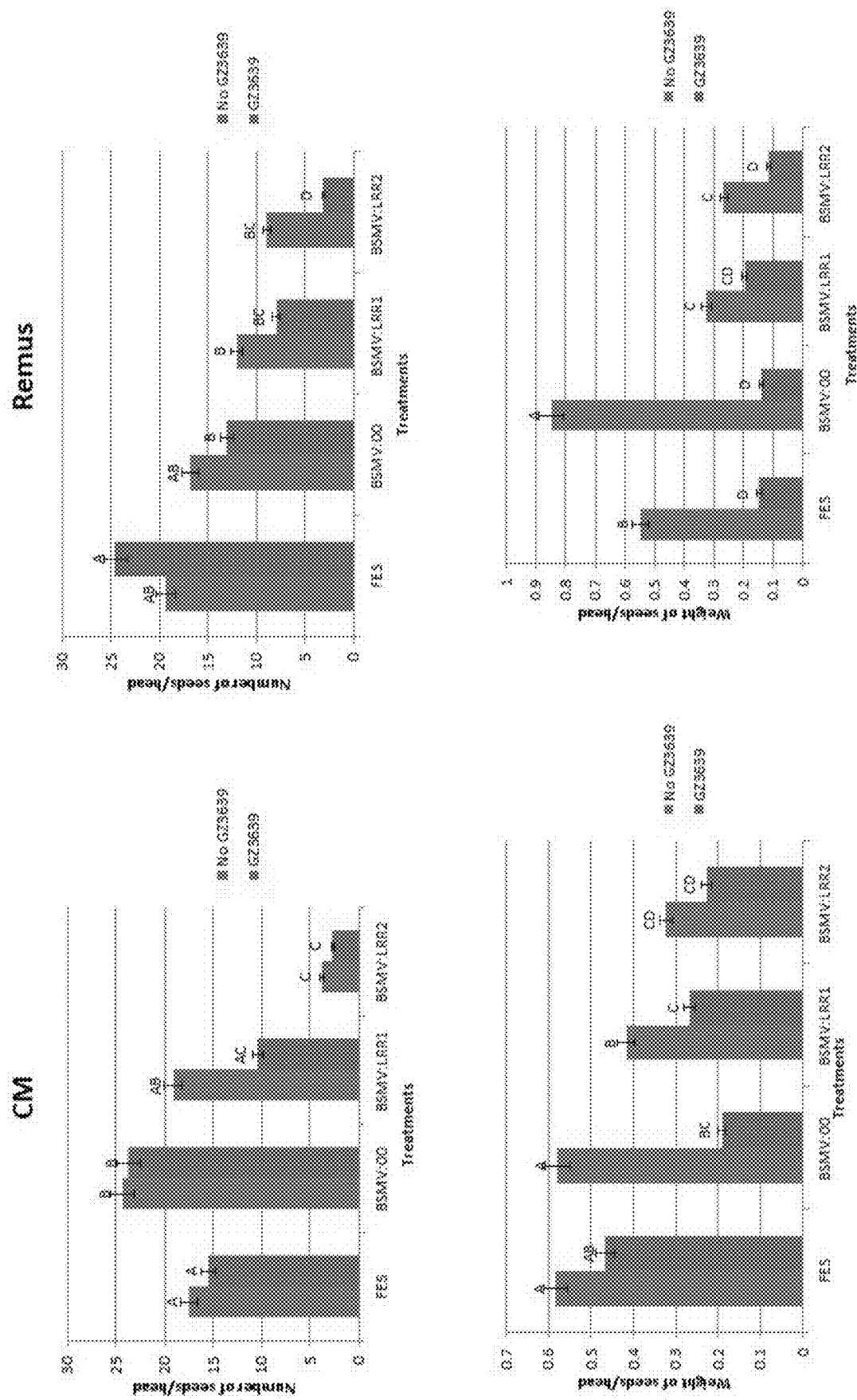
FIG. 10 illustrates FHB-induced damage in TaLRRK-6D silenced and BSMV:00 treated spikelets.

Plants treated with BSMV:LRR1 and BSMV:LRR2 were significantly more sensitive to FHB induced damage of spikelets than the non-silenced plants BSMV:00 (6.5 and 7.3 fold increase), as illustrated by FIG. 9. The TaLRRK-6D silenced spikelets showing FHB-induced damage was significantly reflected in yield reduction as compared to the BSMV:00 treatment (FIG. 10). This indicates a direct role of TaLRRK-6D in FHB resistance in wheat plants.

Example 3

Role of TaLRRK-6D in FHB in Barley

Study Description

In order to understand the role of TaLRRK-6D in *Fusarium* head blight in barley, wild type barley cv. Akashinriki lines were used.

Methodology

VIGS were used to silence LRR-RLK homolog in barley at 2nd leaf stage. Using detached leaf assay described by (Browne & Cooke, 2004), the effect of TaLRRK-6D silencing on the barley in response to *F. culmorum* strain FC200 was assessed. Leaves were point-inoculated with fungal conidia in the wild type cv. Akashinriki and the diseased leaf area monitored at 4 dai.

Results

Figure 11:
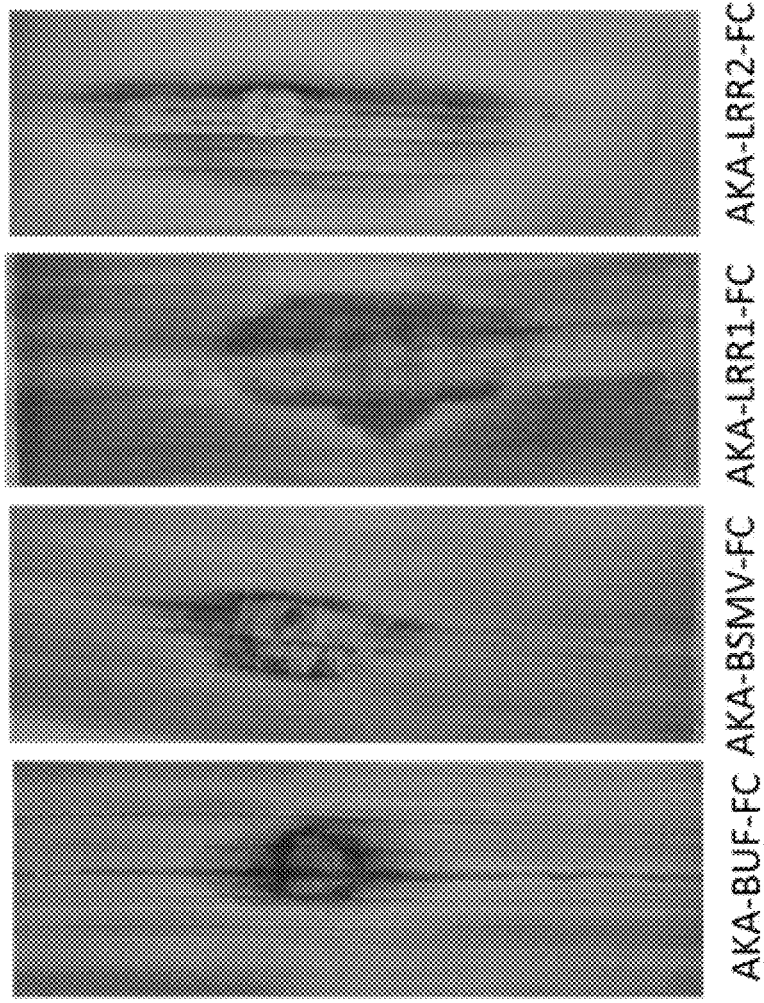
FIG. 11 illustrates lesions in barley cv. Akashinriki silenced lines with constructs BSMV:LRR1 and BSMV:LRR2 and in BSMV:00 treated lines.
Figure 12:
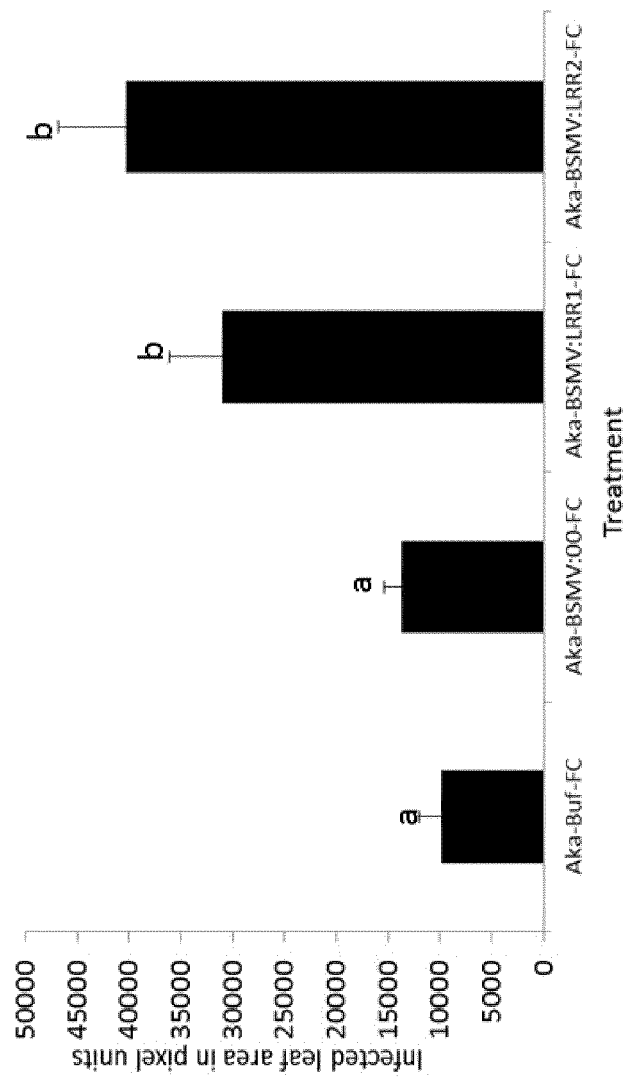
FIG. 12 is a graph illustrating the number of conidia developed on the leaves of BSMV:LRR1 and BSMV:LRR2 silenced lines and on the wild type cv. Akashinriki treated with BSMV:00.

The lines silenced with BSMV:LRR1 and BSMV:LRR2 developed severe lesions, and increased disease symptoms of 2.24 and 3 folds compared to BSMV:00 were observed (P<0.05) for Akashinriki silenced lines with construct BSMV:LRR1 and BSMV:LRR2 respectively as illustrated by FIG. 11. The number of conidia developed on the leaves at 4 dai was also determined and all two BSMV:LRR1 and BSMV:LRR2 silenced lines contained 20 224% and 293% more conidia than the wild type cv. Akashinriki that was treated with BSMV:00 was statistically significant (P<0.05) as illustrated by FIG. 12. The diseased leaf area monitored at 4 dai was found to be 5.8 cm2. Thus, the detached leaf results show that silencing of TaLRRK-6D leads to enhanced wheat leaf susceptibility to *F. colmorum* strain FC200.

The invention claimed is:

1. A method of genetically transforming a plant material comprising the steps of introducing into one or more cells of the plant material with a recombinant construct comprising the nucleotide sequence of SEQ ID NO: 1 or a functional variant of SEQ ID NO: 1 having at least 90% sequence identity with SEQ ID NO: 1, and expressing the nucleotide sequence or the functional variant thereof in the plant material; wherein the expression of the nucleotide sequence or the functional fragment thereof provides *Fusarium* Head Blight (FHB) disease resistance in the plant.

2. The method of claim 1, wherein the one or more cells of the plant material is capable of overexpression of the nucleotide of SEQ ID NO:1 or the functional variant thereof.

3. A method of producing a transformed plant or plant material having resistance to *Fusarium* Head Blight (FHB) disease, the method comprising the step of transforming a plant or plant material with a recombinant construct comprising the nucleotide sequence of SEQ ID NO: 1 or a functional variant of SEQ ID NO: 1 having at least 90% sequence identity with SEQ ID NO: 1, wherein the transformed plant or plant material exhibits FHB resistance.

4. The method of claim 3, wherein the plant material is selected from the group consisting of a plant cell, plant cell culture, plant tissue, and plant seed.

5. The method of claim 4, wherein the plant is a cereal.

6. The method of claim 5, wherein the cereal is selected from the group comprising maize, rice, wheat, barley, sorghum, millet, oats and rye.

7. A transgenic plant or plant material comprising a recombinant construct comprising the nucleotide sequence of SEQ ID NO: 1 or a functional variant of SEQ ID NO: 1 having at least 90% sequence identity with SEQ ID NO: 1, wherein the transformed plant exhibits resistance to *Fusarium* Head Blight (FHB) disease.

8. The transgenic plant or plant material of claim 7, wherein the plant is a cereal.

9. The transgenic plant or plant material of claim 8, wherein the cereal is selected from the group consisting of maize, rice, wheat, barley, sorghum, millet, oats and rye.

10. The transgenic plant or plant material of claim 7, wherein the plant material is selected from the group consisting of a plant cell, plant cell culture, plant tissue and plant seed.

11. The method of claim 1, wherein the construct is an expression vector.

12. The transgenic plant of claim 7, wherein the construct is an expression vector.

13. The method of claim 1, wherein the nucleotide sequence encodes SEQ ID NO: 2 or a functional variant having at least 95% sequence identity with SEQ ID NO: 2.

14. The method of claim 3, wherein the nucleotide sequence encodes SEQ ID NO: 2 or a functional variant having at least 95% sequence identity with SEQ ID NO: 2.

15. The transgenic plant of claim 7, wherein the nucleotide sequence encodes SEQ ID NO: 2 or a functional variant having at least 95% sequence identity with SEQ ID NO: 2.

* * * * *

SEQUENCE LISTING

```
<160> NUMBER OF SEQ ID NOS: 21

<210> SEQ ID NO 1
<211> LENGTH: 3096
<212> TYPE: DNA
<213> ORGANISM: Artificial Sequence
<220> FEATURE:
<223> OTHER INFORMATION: TaLRRK-6D nucleotide sequence

<400> SEQUENCE: 1
atgtctgacc aatccgtgaa actcaacatg cttcttctgc tggcgtttct gctgctgtct    60
```

```
tatggagctg gcaatgcccg ttgctcaact gttcatgcga acatcacaga cattctctcc      120
ttgctccgat tcaaaaggtc cacccacgat ccaacaggtt ccttgaggaa ctggaaccga      180
agcatccatt actgcaagtg gaatggtgtc tcctgcagct tactgaatcc agggcgggtg      240
gcggctttgg atctccctgg ccaaaacttg tcaggtcaag tcaacccttc tcttgggaac      300
ataacgttcc ttaagcgcct gaatttgtcc tccaatggct ctccggcca gttacctgac       360 gcttctcagc atgagctcct acttattcca agggataatc cccgattcac tcacacaatt      420
ttcgaaccta cagctcctga atttgtccta caatggcttc ccggccagt tacctcctct       480 gaaccagctt cccgagctgg tggttctcag cttgaaatcc aatttattcc aagggataat     540
ccccgactca ctcacaaact gttcgaacct cacgtttgtg gatctttcaa gaaacatgct     600
agaaggctca atcccggcga aaataggttc gctttacaat ctaatgaatt tagacctttc     660
aatgaaatga ctcaccgggg tcataccacc aaccatcagc aatgccacca agctacaatt     720
tctcattctt caagaaaaca aactagaggg aagcataccc atgaactaga cttggacaat     780
tgtccaacat tatcggcttt actgttggta gcaataggc tcaggtcaa ataccagcat       840 caatctttaa tcttactttg ctccgagtgc ctggcttgta cgcaaataga ctacaaatgg     900
cggcactgcc acttgacatt ggccacaccc tccctaatct ccaaaatatt actttgggcc    960
aaaacatgct gaaggtcct atcccagcgt cgccaagtaa catttcaagc ctgcaataat     1020
ctcagttatc taataacagt ttcactggag aaattcctag tttcggaaag ctacagaaac    1080
ttgtataccc tcaccttgcg gacaataagc tggagtcaag tgacagccaa agatgggaat    1140
ctttatatgg actggcaaac tgcagtcatc cttaatcgct cagattcaag aataatcagc    1200
cgcaaggagt cataccaaat tcggggagtc ataccaaatt cggtaggtaa attgtcccct    1260
aaacttgaac ttctacatct gggtggaaac aatctatcag gaatagttcc ttcaagcata    1320
ggaaaccttg atggcttaat agatttggat cttagcacaa acagtttcaa tggtacaatt    1380
gaaggatggg taggaagtct taaaaaacta caatctctag atcttcatgg aaacaatttc    1440
gttggagcca ttccacccctc ttttggcaac cttactgagc taacatatct gtatttagca    1500
aaaaatgaat tgaagggac atacctcccc attctcggga acttaaaag actctcagcc      1560 atggacctta gctataataa tcttcaaggt gacattcctc cagaactcag tgggcttaca    1620
caactccgta cactgaatct ttcatctaac agacttacag gagaaattcc tgttgatctg    1680
agccagtgtc aagacctggt aaccatccaa atggaccata taacttgac gggtgacatt    1740 ccaaccactt ttggtgacct tatgagcttg aacatgctca gcctttccta taatgattta    1800 tcagggggcca tccctgtaag tcttcaacat gtcagcaagt tggacttatc tcataatcac    1860
ctccaaggag aaatcccacc agaaggagtg tttaggaatg cctcagccgt ttcgcttgct    1920
ggcaattcag agctttgtgg aggggtgtcg gaactgcata tgcctccatg cccagttgct    1980
tctcagagaa ctaagatacg atattacttg atcagggtat tgataccatt atttggcttc    2040
atgtcgctcc tattattggt ctactttcta gtcctcgaga ggaaaatgag aagaacaaga    2100
tatgaatcac aggctccttt gggtgagcat ttccctaaag tttcttacaa tgatctggtt    2160
gaagcaacaa agaactttc cgagtctaac ctgcttggga aggaagcta tggtacagtg      2220 tacaagggaa acttggtgca gcataagttg gaagtggcag tgaaggtttt taaccttgag    2280
atgcaaggcg cggagagaag cttcatgcca gaatgtgaag cgctgagaag cgttcaacac    2340
cggaatcttt tttccatcat aactgcatgt tctactgttg atagcgacgg tagagctttc    2400
agggccctaa tttacgagtt catgcccaag gggaacttgg acacgtgcct tcatcacaag    2460
```

-continued

```
ggggacggca aagctgataa gcatctgact ttaactcaaa gaatcggcat agctgtcaac    2520
atagcagatg cactggacta tttacataat gacagcgaaa accccatcat ccattgtgat    2580
ctgaagccca gcaatattct tcttgatgag acatggttg ctcatttggg ggatttcggt     2640
attgcaagga ttttcttga ttctgggcta agaccagcaa gctcgacgag ttcaattggt     2700
gtaaaaggaa cgataggcta tatcccacca gagtacggcg ggggaggccg tatatctact    2760
tctggggatg tctacagttt tgggatagtg ctgctggaga tgttgactgg caaaaggcca    2820
acagatccta tgtttatgga tggactggac atcgtcaact tcgtgggcaa caagtttcca    2880
catcaaatac atgaagtgat tgacatttat ctaaaaggag agtgcgagtc agaagattcg    2940
gttcatcagt gcctcgtgtc tctgctgcaa gtagcagtct cctgcacaca ctccatcccc    3000
ggcgaaagag cgaacattag agatacagct agcaagctcc aggaaattaa ggcgtcatat    3060
cttggaagga aggcaaagat aaatccttca gtttaa                              3096
```

<210> SEQ ID NO 2
<211> LENGTH: 1031
<212> TYPE: PRT
<213> ORGANISM: Artificial Sequence
<220> FEATURE:
<223> OTHER INFORMATION: TaLRRK-6D amino acid sequence

<400> SEQUENCE: 2

```
Met Ser Asp Gln Ser Val Lys Leu Asn Met Leu Leu Leu Leu Ala Phe
1               5                   10                  15

Leu Leu Leu Ser Tyr Gly Ala Gly Asn Ala Arg Cys Ser Thr Val His
            20                  25                  30

Ala Asn Ile Thr Asp Ile Leu Ser Leu Leu Arg Phe Lys Arg Ser Thr
        35                  40                  45

His Asp Pro Thr Gly Ser Leu Arg Asn Trp Asn Arg Ser Ile His Tyr
    50                  55                  60

Cys Lys Trp Asn Gly Val Ser Cys Ser Leu Leu Asn Pro Gly Arg Val
65                  70                  75                  80

Ala Ala Leu Asp Leu Pro Gly Gln Asn Leu Ser Gly Gln Val Asn Pro
                85                  90                  95

Ser Leu Gly Asn Ile Thr Phe Leu Lys Arg Leu Asn Leu Ser Ser Asn
            100                 105                 110

Gly Phe Ser Gly Gln Leu Pro Asp Ala Ser Gln His Glu Leu Leu Leu
        115                 120                 125

Ile Pro Arg Asp Asn Pro Arg Phe Thr His Thr Ile Phe Glu Pro Thr
    130                 135                 140

Ala Pro Glu Phe Val Leu Gln Trp Leu Leu Arg Pro Val Thr Ser Ser
145                 150                 155                 160

Glu Pro Ala Ser Arg Ala Gly Gly Ser Gln Leu Glu Ile Gln Phe Ile
                165                 170                 175

Pro Arg Asp Asn Pro Arg Leu Thr His Lys Leu Phe Glu Pro His Val
            180                 185                 190

Cys Gly Ser Phe Lys Lys His Ala Arg Arg Leu Asn Pro Gly Glu Asn
        195                 200                 205

Arg Phe Ala Leu Gln Ser Asn Glu Phe Arg Pro Phe Asn Glu Met Thr
    210                 215                 220

His Arg Gly His Thr Thr Asn His Gln Gln Cys His Gln Ala Thr Ile
225                 230                 235                 240

Ser His Ser Ser Arg Lys Gln Thr Arg Gly Lys His Thr His Glu Leu
```

```
            245                 250                 255
Asp Leu Asp Asn Cys Pro Thr Leu Ser Ala Leu Leu Val Ala Ile
        260                 265                 270
Gly Ser Gln Val Lys Tyr Gln His Gln Ser Leu Ile Leu Leu Cys Ser
    275                 280                 285
Glu Cys Leu Ala Cys Thr Gln Ile Asp Tyr Lys Trp Arg His Cys His
290                 295                 300
Leu Thr Leu Ala Thr Pro Ser Leu Ile Ser Lys Ile Leu Leu Trp Ala
305                 310                 315                 320
Lys Thr Cys Leu Lys Val Leu Ser Gln Arg Arg Gln Val Thr Phe Gln
                325                 330                 335
Ala Cys Asn Asn Leu Ser Tyr Leu Ile Thr Val Ser Leu Glu Lys Phe
                340                 345                 350
Leu Val Ser Glu Ser Tyr Arg Asn Leu Tyr Thr Leu Thr Leu Arg Thr
            355                 360                 365
Ile Ser Trp Ser Gln Val Thr Ala Lys Asp Gly Asn Leu Tyr Met Asp
        370                 375                 380
Trp Gln Thr Ala Val Ile Leu Asn Arg Ser Asp Ser Arg Ile Ile Ser
385                 390                 395                 400
Arg Lys Glu Ser Tyr Gln Ile Arg Gly Val Ile Pro Asn Ser Val Gly
                405                 410                 415
Lys Leu Ser Pro Lys Leu Glu Leu Leu His Leu Gly Asn Asn Leu
                420                 425                 430
Ser Gly Ile Val Pro Ser Ser Ile Gly Asn Leu Asp Gly Leu Ile Asp
            435                 440                 445
Leu Asp Leu Ser Thr Asn Ser Phe Asn Gly Thr Ile Glu Gly Trp Val
        450                 455                 460
Gly Ser Leu Lys Lys Leu Gln Ser Leu Asp Leu His Gly Asn Asn Phe
465                 470                 475                 480
Val Gly Ala Ile Pro Pro Ser Phe Gly Asn Leu Thr Glu Leu Thr Tyr
                485                 490                 495
Leu Tyr Leu Ala Lys Asn Glu Phe Glu Gly Thr Ile Pro Pro Ile Leu
                500                 505                 510
Gly Lys Leu Lys Arg Leu Ser Ala Met Asp Leu Ser Tyr Asn Asn Leu
            515                 520                 525
Gln Gly Asp Ile Pro Pro Glu Leu Ser Gly Leu Thr Gln Leu Arg Thr
        530                 535                 540
Leu Asn Leu Ser Ser Asn Arg Leu Thr Gly Glu Ile Pro Val Asp Leu
545                 550                 555                 560
Ser Gln Cys Gln Asp Leu Val Thr Ile Gln Met Asp His Asn Asn Leu
                565                 570                 575
Thr Gly Asp Ile Pro Thr Thr Phe Gly Asp Leu Met Ser Leu Asn Met
                580                 585                 590
Leu Ser Leu Ser Tyr Asn Asp Leu Ser Gly Ala Ile Pro Val Ser Leu
            595                 600                 605
Gln His Val Ser Lys Leu Asp Leu Ser His Asn His Leu Gln Gly Glu
        610                 615                 620
Ile Pro Pro Glu Gly Val Phe Arg Asn Ala Ser Ala Val Ser Leu Ala
625                 630                 635                 640
Gly Asn Ser Glu Leu Cys Gly Gly Val Ser Glu Leu His Met Pro Pro
                645                 650                 655
Cys Pro Val Ala Ser Gln Arg Thr Lys Ile Arg Tyr Tyr Leu Ile Arg
                660                 665                 670
```

-continued

```
Val Leu Ile Pro Leu Phe Gly Phe Met Ser Leu Leu Leu Val Tyr
            675                 680                 685

Phe Leu Val Leu Glu Arg Lys Met Arg Arg Thr Arg Tyr Glu Ser Gln
690                 695                 700

Ala Pro Leu Gly Glu His Phe Pro Lys Val Ser Tyr Asn Asp Leu Val
705                 710                 715                 720

Glu Ala Thr Lys Asn Phe Ser Glu Ser Asn Leu Leu Gly Lys Gly Ser
            725                 730                 735

Tyr Gly Thr Val Tyr Lys Gly Asn Leu Val Gln His Lys Leu Glu Val
            740                 745                 750

Ala Val Lys Val Phe Asn Leu Glu Met Gln Gly Ala Glu Arg Ser Phe
            755                 760                 765

Met Pro Glu Cys Glu Ala Leu Arg Ser Val His Arg Asn Leu Val
            770                 775                 780

Ser Ile Ile Thr Ala Cys Ser Thr Val Asp Ser Asp Gly Arg Ala Phe
785                 790                 795                 800

Arg Ala Leu Ile Tyr Glu Phe Met Pro Lys Gly Asn Leu Asp Thr Cys
            805                 810                 815

Leu His His Lys Gly Asp Gly Lys Ala Asp Lys His Leu Thr Leu Thr
            820                 825                 830

Gln Arg Ile Gly Ile Ala Val Asn Ile Ala Asp Ala Leu Asp Tyr Leu
            835                 840                 845

His Asn Asp Ser Glu Asn Pro Ile Ile His Cys Asp Leu Lys Pro Ser
850                 855                 860

Asn Ile Leu Leu Asp Glu Asp Met Val Ala His Leu Gly Asp Phe Gly
865                 870                 875                 880

Ile Ala Arg Ile Phe Leu Asp Ser Gly Leu Arg Pro Ala Ser Ser Thr
            885                 890                 895

Ser Ser Ile Gly Val Lys Gly Thr Ile Gly Tyr Ile Pro Pro Glu Tyr
            900                 905                 910

Gly Gly Gly Gly Arg Ile Ser Thr Ser Gly Asp Val Tyr Ser Phe Gly
            915                 920                 925

Ile Val Leu Leu Glu Met Leu Thr Gly Lys Arg Pro Thr Asp Pro Met
            930                 935                 940

Phe Met Asp Gly Leu Asp Ile Val Asn Phe Val Gly Asn Lys Phe Pro
945                 950                 955                 960

His Gln Ile His Glu Val Ile Asp Ile Tyr Leu Lys Gly Glu Cys Glu
            965                 970                 975

Ser Glu Asp Ser Val His Gln Cys Leu Val Ser Leu Leu Gln Val Ala
            980                 985                 990

Val Ser Cys Thr His Ser Ile Pro  Gly Glu Arg Ala Asn  Ile Arg Asp
            995                 1000                1005

Thr Ala  Ser Lys Leu Gln Glu  Ile Lys Ala Ser Tyr  Leu Gly Arg
    1010                 1015                 1020

Lys Ala  Lys Ile Asn Pro Ser  Val
    1025                 1030
```

<210> SEQ ID NO 3
<211> LENGTH: 3093
<212> TYPE: DNA
<213> ORGANISM: Artificial Sequence
<220> FEATURE:
<223> OTHER INFORMATION: TaLRRK-6D variant

<400> SEQUENCE: 3

-continued

```
atgtctgacc aatccgtgaa actcaacatg cttcttctgc tggcgtttct gctgctgtct    60
tatggagctg gcaatgcccg ttgctcaact gttcatgcga acatcacaga cattctctcc   120
ttgctccgat tcaaaaggtc cacccacgat ccaacaggtt ccttgaggaa ctggaaccga   180
agcatccatt actgcaagtg gaatggtgtc tcctgcagct tactgaatcc agggcgggtg   240
gcggctttgg atctccctgg ccaaaacttg tcaggtcaag tcacccttc tcttgggaac    300
ataacgttcc ttaagcgcct gaatttgtcc tccaatggct ctccggcca gttacctcct    360
ctgagtcagc tccatgagct gacgcttctt gacatgagct caacttatt ccaagggata    420
atccccgatt cactcacaca atttcgaac ctacagctcc tgaatttgtc ctacaatggc    480
ttctccggcc agttacctcc tctgaaccag cttcccgagc tggtggttct tgacttgaaa    540
tccaatttat tccaagggat aatcccgac tcactcacaa actgttcgaa cctcacgttt    600
gtggatcttt caagaaacat gctagaaggc tcaatcccgg cgaaaatagg ttcgctttac    660
aatctaatga atttagacct ttctaggaat aaactcaccg gggtcatacc accaaccatc    720
agcaatgcca ccaagctaca atttctcatt cttcaagaaa atgaactaga gggaagcata    780
cccagtgagc ttgacaatt gtccaacatg atcggcttta ctgttggtag caataggctc    840
tcaggtcaaa taccagcatc aatctttaat cttactttgc tccgagtgct aggcttgtac    900
gcaaatagac tacaaatggc ggcactgcca cttgacattg ccacaccct ccctaatctc     960
caaaatatta ctttgggcca aacatgctt gaaggtccta tcccagcgtc gctaggtaac   1020
atttcaagcc tgcaattaat agagttatct aataacagtt tcactggaga aattcctagt   1080
ttcggaaagc tacagaaact tgtataccta aaccttgcgg acaataagct ggagtcaagt   1140
gacagccaaa gatgggaatc tttatatgga ctaacaaact gcagtcatct aaaatcgctc   1200
agattcaaga ataatcagct gaaggagtc ataccaaatt cggtaggtaa attgtcccct   1260
aaacttgaac ttctacatct gggtggaaac aatctatcag gaatagttcc ttcaagcata   1320
ggaaaccttg atggcttaat agatttggat cttagcacaa acagtttcaa tggtacaatt   1380
gaaggatggg taggaagtct taaaaaacta caatctctag atcttcatgg aaacaatttc   1440
gttggagcca ttccaccctc ttttggcaac cttactgagc taacatatct gtatttagca   1500
aaaaatgaat tgaagggac catacctccc attctcggga aacttaaaag actctcagcc   1560
atggacctta gctataataa tcttcaaggt gacattcctc cagaactcag tgggcttaca   1620
caactccgta cactgaatct ttcatctaac agacttacag agaaaattcc tgttgatctg   1680
agccagtgtc aagacctggt aaccatccaa atggaccata ataacttgac gggtgacatt   1740
ccaaccactt tggtgacct tatgagcttg aacatgctca gcctttccta taatgattta   1800
tcaggggcca tccctgtaag tcttcaacat gtcagcaagt tggacttatc tcataatcac   1860
ctccaaggag aaatcccacc agaaggagtg tttaggaatg cctcagccgt ttcgcttgct   1920
ggcaattcag gctttgtgg aggggtgtcg gaactgcata tgcctccatg cccagttgct   1980
tctcagagaa ctaagatacg atattacttg atcagggtat tgataccatt atttggcttc   2040
atgtcgctcc tattattggt ctactttcta gtcctcgaga ggaaaatgag aagaacaaga   2100
tatgaatcac aggctccttt gggtgagcat ttccctaaag tttcttacaa tgatctggtt   2160
gaagcaacaa agaactttc cgagtctaac ctgcttggga aaggaagcta tggtacagtg   2220
tacaagggaa acttggtgca gcataagttg gaagtggcag tgaaggtttt taaccttgag   2280
atgcaaggcg cggagagaag cttcatgcca gaatgtgaag cgctgagaag cgttcaacac   2340
```

-continued

| | |
|---|---|
| cggaatcttg tttccatcat aactgcatgt tctactgttg atagcgacgg tagagctttc | 2400 |
| agggccctaa tttacgagtt catgcccaag gggaacttgg acacgtgcct tcatcacaag | 2460 |
| ggggacggca agctgataa gcatctgact ttaactcaaa gaatcggcat agctgtcaac | 2520 |
| atagcagatg cactggacta tttacataat gacagcgaaa accccatcat ccattgtgat | 2580 |
| ctgaagccca gcaatattct tcttgatgag acatggttg ctcatttggg ggatttcggt | 2640 |
| attgcaagga tttttcttga ttctgggcta agaccagcaa gctcgacgag ttcaattggt | 2700 |
| gtaaaaggaa cgataggcta tatcccacca gagtacggcg ggggaggccg tatatctact | 2760 |
| tctggggatg tctacagttt tgggatagtg ctgctggaga tgttgactgg caaaaggcca | 2820 |
| acagatccta tgtttatgga tggactggac atcgtcaact tcgtgggcaa caagttttcca | 2880 |
| catcaaatac atgaagtgat tgacatttat ctaaaaggag agtgcgagtc agaagattcg | 2940 |
| gttcatcagt gcctcgtgtc tctgctgcaa gtagcagtct cctgcacaca ctccatcccc | 3000 |
| ggcgaaagag cgaacattag agatacagct agcaagctcc aggaaattaa ggcgtcatat | 3060 |
| cttggaagga aggcaaagat aaatccttca gtt | 3093 |

<210> SEQ ID NO 4
<211> LENGTH: 3064
<212> TYPE: DNA
<213> ORGANISM: Artificial Sequence
<220> FEATURE:
<223> OTHER INFORMATION: TaLRRK-6D variant

<400> SEQUENCE: 4

| | |
|---|---|
| atgtctgacc aatccgtgaa actcaacatg cttcttctgc tggcgtttct gctgctgtct | 60 |
| tatggagctg gcaatgcccg ttgctcaact gttcatgcga acatcacaga cattctctcc | 120 |
| ttgctccgat tcaaaaggtc cacccacgat ccaacaggtt ccttgaggaa ctggaaccga | 180 |
| agcatccatt actgcaagtg gaatggtgtc tcctgcagct tactgaatcc agggcgggtg | 240 |
| gcggctttgg atctccctgg ccaaaacttg tcaggtcaag tcaacccttc tcttgggaac | 300 |
| ataacgttcc ttaagcgcct gaatttgtcc tccaatggct ctccggcca gttacctgac | 360 |
| gcttctcaac atgagctctt acttattcca agggataatc cccgattcac tcacacaatt | 420 |
| ttcgaaccta cagctcctga atttgtccta caatggcttc tccggccagt tacctcctct | 480 |
| gaaccagctt cccgagctgg tggttctcaa cttgaaatcc aatttattcc aagggataat | 540 |
| ccccgactca ctcacaaact gttcgaacct cacgtttgtg gatctttcaa gaaacatgct | 600 |
| agaaggctca atcccggcga aaataggttc gctttacaat ctaatgaatt tagacctttc | 660 |
| aacgaaatga ctcaccgggg tcataccacc aaccatcagc caatgccacc aagctacaat | 720 |
| ttctcattct tcaagaaaat gcacctagag gggaagcata cccagctagc ttggacaatt | 780 |
| gtccaacatg attcggcttt actggttgga agcaataagg ctctcaggtc aaatgcccag | 840 |
| catgcaatct ttaaatctta ctttggatcc aagtgcttag gttggtacgc caacaaaact | 900 |
| accaaatggc gggcactgcc aattagaatt gggccaaacc ctcccctaat ttccaaaaaa | 960 |
| ttaactttgg gccaaaaaaa ggctatgaag gtcctatccc agcgtcgctc ggtaacattt | 1020 |
| caagcctgca atctccaaag ttatccaatt acagtttcac tggagaaatt cctagtttcg | 1080 |
| gaaagctaca gaaacttgta tacctatacc ttgcggacaa taagctggag tcaagtgaca | 1140 |
| gccaaagatg ggaatcttta tatggaccag caaactgcag tcatccacaa tcgctcagat | 1200 |
| tcaagaataa tcagccagaa ggagtcttac caaattcgga gcgtaaattg tccccctaaac | 1260 |
| ttgaacttct acatctgggg tggaaacaat ctatcaggaa tagttccttc aagctccgga | 1320 |

```
aaccttgatg gcttaataga tttggatctt agcacaaaca gtttcaatgg tacaattgaa    1380
ggatgggtag gaagtcttaa aaaactacaa tctctagatc ttcatggaaa caatttcgtt    1440
ggagccattc caccctcttt tggcaacctt actgagctaa catatctgta tttagcaaaa    1500
aatgaatttg aagggaccat acctcccatt ctcgggaaac ttaaaagact ctcagccatg    1560
gaccttagct ataataatct tcaaggtgac attcctccag aactcagtgg cttacacaa     1620 ctccgtacac tgaatctttc atctaacaga cttacaggag aaattcctgt tgatctgagc    1680
cagtgtcaag acctggtaac catccaaatg gaccataata acttgacggg tgacattcca    1740 accactttg gtgaccttat gagcttgaac atgctcagcc tttcctataa tgatttatca     1800
ggggccatcc ctgtaagtct tcaacatgtc agcaagttgg acttatctca taatcacctc    1860
caaggagaaa tcccaccaga aggagtgttt aggaatgcct cagccgtttc gcttgctggc    1920
aattcagagc tttgtggagg ggtgtcggaa ctgcatatgc ctccatgccc agttgcttct    1980
cagagaacta agatacgata ttacttgatc agggtattga taccattatt tggcttcatg    2040
tcgctcctat tattggtcta ctttctagtc ctcgagagga aaatgagaag aacaagatat    2100
gaatcacagc ctccttgggg tgagcatttc cctaaagttt cttacaatga tctggttgaa    2160
gcaacaaaga acttttccga gtctaacctg cttgggaaag aagctatgg tacagtgtac     2220 aagggaaact tggtgcagca taagttggaa gtggcagtga aggttttaa ccttgagatg      2280 caaggcgcgg agagaagctt catgccagaa tgtgaagcgc tgagaagcgt tcaacaccgg    2340
aatcttgttt ccatcataac tgcatgttct actgttgata gcgacggtag agctttcagg    2400
gccctaattt acgagttcat gcccaagggg aacttggaca cgtgccttca tcacaagggg    2460
gacggcaaag ctgataagca tctgacttta actcaaagaa tcggcatagc tgtcaacata    2520
gcagatgcac tggactattt acataatgac agcgaaaacc ccatcatcca ttgtgatctg    2580
aagcccagca atattcttct tgatgaggac atggttgctc atttgggga tttcggtatt     2640 gcaaggattt ttcttgattc tgggctaaga ccagcaagct cgacgagttc aattggtgta    2700
aaaggaacga taggctatat cccaccagag tacggcgggg gaggccgtat atctacttct    2760
ggggatgtct acagttttgg gatagtgctg ctggagatgt tgactggcaa aaggccaaca    2820
gatcctatgt ttatggatgg actggacatc gtcaacttcg tgggcaacaa gtttccacat    2880
caaatacatg aagtgattga catttatcta aaaggagagt gcgagtcaga agattcggtt    2940
catcagtgcc tcgtgtctct gctgcaagta gcagtctcct gcacacactc catccccggc    3000
gaaagagcga acattagaga tacagctagc aagctccaga aaaaggtcgt caactgcccc    3060
ctaa                                                                 3064
```

<210> SEQ ID NO 5
<211> LENGTH: 3096
<212> TYPE: DNA
<213> ORGANISM: Artificial Sequence
<220> FEATURE:
<223> OTHER INFORMATION: TaLRRK-6D variant

<400> SEQUENCE: 5

```
atgtctgacc aatccgtgaa actcaacatg cttcttctgc tggcgtttct gctgctgtct      60
tatggagctg gcaatgcccg ttgctcaact gttcatgcga acatcacaga cattctctcc    120
ttgctccgat tcaaaaggtc cacccacgat ccaacaggtt ccttgaggaa ctggaaccga    180
agcatccatt actgcaagtg gaatggtgtc tcctgcagct tactgaatcc agggcgggtg    240
```

-continued

```
gcggctttgg atctccctgg ccaaaacttg tcaggtcaag tcaacccttc tcttgggaac    300
ataacgttcc ttaagcgcct gaatttgtcc tccaatggct tctccggcca gttacctcct    360
ctgagtcagc tccatgagct gacgcttctt gacatgagct ctaacttatt ccaagggata    420
atccccgatt cactcacaca attttcgaac ctacagctcc tgaatttgtc ctacaatggc    480
ttctccggcc agttacctcc tctgaaccag cttcccgagc tggtggttct tgacttgaaa    540
tccaatttat tccaagggat aatcccgac tcactcacaa actgttcgaa cctcacgttt    600
gtggatcttt caagaaacat gctagaaggc tcaatcccgg cgaaaatagg ttcgctttac    660
aatctaatga atttagacct ttctaggaat aaactcaccg gggtcatacc accaaccatc    720
agcaatgcca ccaagctaca atttctcatt cttcaagaaa atgaactaga gggaagcata    780
cccagtgagc ttggacaatt gtccaacatg atcggcttta ctgttggtag caataggctc    840
tcaggtcaaa taccagcatc aatctttaat cttactttgc tccgagtgct aggcttgtac    900
gcaaatagac tacaaatggc ggcactgcca cttgacattg ccacaccct ccctaatctc    960 caaaatatta ctttgggcca aaacatgctt gaaggtccta tcccagcgtc gctaggtaac   1020
atttcaagcc tgcaattaat agagttatct aataacagtt tcactggaga aattcctagt   1080
ttcggaaagc tacagaaact tgtataccta aaccttgcgg acaataagct ggagtcaagt   1140
gacagccaaa gatgggaatc tttatatgga ctaacaaact gcagtcatct aaaatcgctc   1200
agattcaaga taatcagct gaaaggagtc ataccaaatt cggtaggtaa attgtcccct   1260
aaacttgaac ttctacatct gggtggaaac aatctatcag gaatagttcc ttcaagcata   1320
ggaaaccttg atggcttaat agatttggat cttagcacaa acagtttcaa tggtacaatt   1380
gaaggatggg taggaagtct taaaaaacta caatctctag atcttcatgg aaacaatttc   1440
gttggagcca ttccaccctc ttttggcaac cttactgagc taacatatct gtatttagca   1500
aaaaatgaat ttgaagggac catacctccc attctcggga aacttaaaag actctcagcc   1560
atggacctta gctataataa tcttcaaggt gacattcctc cagaactcag tgggcttaca   1620
caactccgta cactgaatct ttcatctaac agacttacag agaaattcc tgttgatctg   1680 agccagtgtc aagacctggt aaccatccaa atggaccata taacttgac gggtgacatt   1740 ccaaccactt ttggtgacct tatgagcttg aacatgctca gccttttccta taatgattta   1800 tcaggggcca tccctgtaag tcttcaacat gtcagcaagt tggacttatc tcataatcac   1860
ctccaaggag aaatcccacc agaaggagtg tttaggaatg cctcagccgt ttcgcttgct   1920
ggcaattcag agctttgtgg aggggtgtcg gaactgcata tgcctccatg cccagttgct   1980
tctcagagaa ctaagatacg atattacttg atcagggtat tgataccatt atttggcttc   2040
atgtcgctcc tattattggt ctactttcta gtcctcgaga ggaaaatgag aagaacaaga   2100
tatgaatcac aggctccttt gggtgagcat ttccctaaag tttcttacaa tgatctggtt   2160
gaagcaacaa agaactttc cgagtctaac ctgcttggga aaggaagcta tggtacagtg   2220
tacaagggaa acttggtgca gcataagttg gaagtggcag tgaaggtttt taacccttgag   2280 atgcaaggcg cggagagaag cttcatgcca gaatgtgaag cgctgagaag cgttcaacac   2340
cggaatcttg tttccatcat aactgcatgt tctactgttg atagcgacgg tagagctttc   2400
agggccctaa tttacgagtt catgcccaag gggaacttgg acacgtgcct tcatcacaag   2460
ggggacggca agctgataaa gcatctgact ttaactcaaa gaatcggcat agctgtcaac   2520
atagcagatg cactggacta tttacataat gacagcgaaa accccatcat ccattgtgat   2580
ctgaagccca gcaatattct tcttgatgag acatggttg ctcatttggg ggatttcggt   2640
```

-continued

```
attgcaagga ttttctcttga ttctgggcta agaccagcaa gctcgacgag ttcaattggt    2700
gtaaaaggaa cgataggcta tatcccacca gagtacggcg ggggaggccg tatatctact    2760
tctggggatg tctacagttt tgggatagtg ctgctggaga tgttgactgg caaaaggcca    2820
acagatccta tgtttatgga tggactggac atcgtcaact tcgtgggcaa caagtttcca    2880
catcaaatac atgaagtgat tgacatttat ctaaaaggag agtgcgagtc agaagattcg    2940
gttcatcagt gcctcgtgtc tctgctgcaa gtagcagtct cctgcacaca ctccatcccc    3000
ggcgaaagag cgaacattag agatacagct agcaagctcc aggaaattaa ggcgtcatat    3060
cttggaagga aggcaaagat aaatccttca gtttaa                              3096
```

<210> SEQ ID NO 6
<211> LENGTH: 3030
<212> TYPE: DNA
<213> ORGANISM: Artificial Sequence
<220> FEATURE:
<223> OTHER INFORMATION: TaLRRK-6D variant

<400> SEQUENCE: 6

```
atgaagctct tcgtgctcgt agcatgggca ctgttgttat tgtctcatgg atctggaagc     60
gtcatttgcg ccgtcctcca tgggaacgat acagatatgc tgtcgcttct tgatttcaag    120
cgcgcaatca ccgaagatcc gaagggctc ttgagcacat ggaacaccag cattcatttc    180
tgcaactggc agggtgtgaa gtgcagcctc acagagcatg agcgtgttgc agagctggac    240
ctgtctgagc agagttttgt cggggaaatc tctccttccc ttggaaacat gtcatatctt    300
acttatctta accttttccag aagcaagttc tctggtcaga taccacattt tggccggctg    360
cgagagctgg agtttcttga cctgagtcac aactcgctac aagggattat tccagtgacg    420
ctcacaaact gctccaactt gagggcgtta gacctctcaa gaaacttatt ggtgggtgaa    480
attcccgcag aaatatccct tctctccaac ctgacacgct tgtggctttc ttataatgat    540
cttaccgggg tcattccacc aggccttggc aatatcactt ctctagaaca tgttattctg    600
atgtataacc ggttagaggg aggcattcct gatgagtttg ggaagttgtc caagatgtca    660
aacttactcc ttggtgaaaa caagctatca ggtagagtcc caaaggccat ttttaatctg    720
tctctgctaa atcaaatggc gctggagttg aatatgctag ttggtactct accatctaac    780
atgggtgatg ctctcccta cctccgactt cttacattgg gtggtaacat gctgaaggt     840 cttatccctg actcattagg caatgcatcc gagctacagc tgataaactt agcatataat    900
cacgggttta gaggacgagt cccaccttct cttggtaaac ttccgaagct cagtaagcta    960
ggtcttgaca caaacagtct tgaagcaaat gacagctggg gctgggaatt cttggatgca   1020
ttgagcaact gcacttctct agagatgctt tcactctatg caaatcggct acaaggaaac   1080
ttgccaaatt ctgttggcaa ccttcgtct aatgttaaca cctcgtgtt tggtaggaat    1140 atgctatatg gattagttcc gtcaagcata ggaaatctcc atagactaac taagctagga   1200
ctggaggaga acagtttgac tggtccgatt gatggatggg ttggaaatct tgctaatttg   1260
caaggtttat atcttcaaca gaacaatttc accgggcaga ttccaacttc cattggcaat   1320
aactccaagc tgtcagaact gtttctggca ataatcaat ccacggtcc cattccatca    1380 agtttcgaaa accttcagca actcttgtat ttagacctca gctataacaa tcttcaagaa   1440
aatataccaa aagagctttt tagtatagcc acaattgccc aatgtgcgct atcccacaac   1500
agtctagaag gccaaattcc tcacatcagt aatcttcaac aactcaacta tctagatctt   1560
```

| | |
|---|---|
| tcatccaaca agcttacagg ggaaattcca cctactttgc gcacatgcca gcaatcgcaa | 1620 |
| gccatcaaat tggaccggaa cttcctctcg ggaagcattc ccatgtttct agggagtctg | 1680 |
| aacagcttga tcgagctcaa ccttttcacat aacaatctct caggctctat cccaattgct | 1740 |
| ctaagcaaac tgcaacttct cacccagttg gatctatccg acaatcatct tgaaggagaa | 1800 |
| gtaccagtag aaggaatatt caaaaataca acagccattt ccctgaaagg caattggcgg | 1860 |
| ctttgtggag gtgtgctgga cctacatatg ccttcatgcc ccgctgcttc tcatagaaga | 1920 |
| tctagatggc aatactattt ggtgagagta ttggtcccta tattaggcat cttgttactc | 1980 |
| atattagtag tctgcttatc ccttctcaga agaggatgc tgaggatgca gttatcgttg | 2040 |
| ccttcttccg atgagcaatt ccctaaagta tcttataagg atctaccaca ggctactgag | 2100 |
| aacttcacag tatataactt gattgggaga ggaagctgcg gttcagtgta cagagcaaag | 2160 |
| ctaaaccaaa aacagatggt tgtggcagtg aaagttttg accttgacat gcaaggcgcg | 2220 |
| gataaaagtt tcatctcaga atgtaaagca ctgagaaaca ttcggcaccg taatcttctt | 2280 |
| ccaattctga ctgcatgctc aacaattgat aaccaaggcc gggatttcaa agctctagtc | 2340 |
| taccagttca tgcccaacgg caacctggac acttggctgc acccggcagg agatggaaaa | 2400 |
| gccccaaagc aactggaccct ctctcaaaga atgaaaatag ctgttgatat agccgatgca | 2460 |
| ttgcaatata taccatga ctgtgagaat cctattgttc actgtgattt gaagcccagc | 2520 |
| aatatcctcc tagattatga tatgacagct cgttggggg actttggcat cgcaaggttg | 2580 |
| tacatcaaat ccaaatcagc ggcagctgga ggttcgagtt caatgggtac aataactctg | 2640 |
| aggggcacga ttggatatat tgctccagag tatgcgggag gtggctacct atcgacgtct | 2700 |
| ggagacgcgt acagttttgg gatagtgctg ctggagatgc tgacaggaag aaggccgacc | 2760 |
| gaccctatgt tctgcgaggg gcttgacatc gtgaactttg tcaagaggaa ctttccggat | 2820 |
| cagatacttg atatccttga cgcttctctc cgagaagaat gtcaagactg ttctcaggat | 2880 |
| aatctggaag gagaaaacga agtccaccgg tgcctgctgt ccttgctgaa agtggcactt | 2940 |
| tcttgcgcaa gccaggatcc taacgaacga atgaacatga gagaagcagc tactgaattg | 3000 |
| cacgcgatcg acacattgta tgtgtcttga | 3030 |

<210> SEQ ID NO 7
<211> LENGTH: 3027
<212> TYPE: DNA
<213> ORGANISM: Artificial Sequence
<220> FEATURE:
<223> OTHER INFORMATION: TaLRRK-6D variant

<400> SEQUENCE: 7

| | |
|---|---|
| atgtctgtga cgagactcag catggttaat ctgctggcgt ttttgctgct gctgttctat | 60 |
| ggagctggca acatcaattg ctcaacagtc aatcacgaga acagtagaga catgcgctcg | 120 |
| ttgctggatt tcaaagcggc taccaacgac ccaacagatg ccttgagatc ctgggacaga | 180 |
| agcgtccact actgcaactg gacgggtgtc atttgcagct cattgtgtcc agggcgtgtc | 240 |
| gccgctctgc aactcgccgg ccaaagcttg tctggcgaga tcaccccctc tcttgggaac | 300 |
| ttaacgttcc ttaaggtcct caacttgtcc tccaatggct ctcaggcca gttaactccc | 360 |
| ctaaacctaa accaactcca tgagctggtc ctccttgacc tcagctccaa ttcattccag | 420 |
| gggacgattc ctgactcact catgaattgt tcaaaactac agtatctagt tcttcttgga | 480 |
| aacatgctag aaggtccaat ccccaagaaa attggttctc tttataatct attaggctta | 540 |
| ggcctttcta ggaataatct tattggggtc atcccactaa ccatcagcaa ctccacccag | 600 |

```
ttagaacaac ttagccttga agaaaatcaa ctagggggga gcattcctga tgtgtttggg     660
caatggtcca agatgttgga attgtccgta ggtgaaaata ggctctcagg tcgaatacca     720
ccttcaatct ttaatctgac ttcgcttcaa atattagatt tgtatgcaaa taagctacaa     780
ggggaattgc tgcttgacat tggcgatacc ctccctgaaa tcataatttt tacgctgggc     840
cagaacattc ttgaaggtca catcccagct tccctaggaa acgcttcacg gctgcaagtg     900
atagatttgt cttctaacag tttcgttgga gaaattccta ctttcggaaa gctactaaac     960
cttatgaaca tgaaccttgg atataatatg cttgaatcaa gtgaaagcca agatgggaa    1020 tccttgtatg gactaacaaa ctgtagtaat ctatatgcgc taacattaga tagtaatcag    1080
ctgcaaggag ccataccaga tttggtcggt aggttatcca ctaaactcag acgtctacac    1140
atgggtggaa acaatctgtc gggaatagtt cctttaagcc tagcaaacct tagtagcata    1200
atcgatttgg atcttagcaa caacaattta actggtacag tcgaaggatg gttagggagt    1260
ctcaaaaact acaatctttt agatcttcat ggaaataatt tcattggatc cattccacca    1320
tcttttggca acctttcaga actgacaata cttttcttta gcacaaaatga atttaaaggt    1380 cacataccct ccacattagg aaaactttca caactctcaa ggctggacct tagctataat    1440
aatctgcaag gtgacatacc tccagaaatt agtgagctta acaactcat tgcactatac     1500 ctctcttcta gcagactctc gggaaaaatt cctgatgatc tgggcaagtg tcagggcctc    1560
gtaaccatcc aaatggacca caataatctc acgggcgtca ttccaacctc tttaggcaac    1620
cttttgagct tgtacatgct caacctgtcc tataatgatt tatcaggtgc catcccaaca    1680
gttctaagtg accttcaact tcttagcaag ttagacctat catataatcg tctccaagga    1740
gcactcccaa gaaatggagt gttttgagcac cctgcaaacg tttcacttga tggcaaccag    1800
ggactttgtg gacgggcaac cggtttccat gtgccctcat gcccagatgc ctcgccgaga    1860
acaggaagac attatcgttt gcttacggtg ttgatcccaa taattggctt cctgtcgctg    1920
gcactgttga cttgctttat aatccatgag aagataccac aagcaacgtt ttcattgttg    1980
ccttctctta gggagaaatt ccctagagtt tcttactggg atctagctcg agcgacaggc    2040
aacttctctg agattaactt gattggcgaa ggaagttaca gttcagtgta caaggaaag    2100 ttgagacaag ttaaaacgga aatagcagtc aagatacttg accttgacat tccaggtgcc    2160
gaaggaagtt tgcattaga atgcaaagcg ttgagaggca tccgtcacag aaacattgtt    2220
cctctcataa ctgaatgctc tgcaatcgac aacaaaggca atgctttcag agctctaatc    2280
tatgctttca tgcccaatgg caacttggat acttggttgc atcatcaagg gaatcaggca    2340
gctgcaaggc atttaagctt agctcaaaga ataaacatcg ctattaacat agctgatgca    2400
ttggactatc tgcaccatga tacttggagg cccatcatcc attgtgattt gaagccgagt    2460
aacatactcc tagacattca tatgaatgcc tgtctgggag actttggcat cgcaaggttc    2520
tacattgatt ctaaactaag aacggtcgga gattcaagtt caattgctgc aaacggcact    2580
ctgggatata tggctccaga gtatgctgaa agcggtcatg catctacttg tggggacgta    2640
tatagtttcg gaatagtact cttggagatg ctgacaggaa aaagaccaac agatcatatg    2700
ttcaggaatg aactcaccat tgtcagattt gtggaacgaa ttttcctga tcacatatta    2760 aattttctgg attcctgtct gctagatgaa tgcaatgatg ccatcaacca agtagcagca    2820
ggactggaaa atccggcaat cttcagtcc ttgttatctt tgctacggat agcacttctt     2880
tgtacacgcc aatccccaac tgaacggctt aacatgaggg aagtagctac ccaaatgcac    2940
```

| | |
|---|---:|
| aaaatcaacg tggtgaacac gggagggaga gtgaggagct caacttcttt taagagactt | 3000 |
| gtcagctggg cttctcaatg gagctaa | 3027 |

<210> SEQ ID NO 8
<211> LENGTH: 3030
<212> TYPE: DNA
<213> ORGANISM: Artificial Sequence
<220> FEATURE:
<223> OTHER INFORMATION: TaLRRK-6D variant

<400> SEQUENCE: 8

| | |
|---|---:|
| atgaagctct tcgtgctcat agtatgggca ctgttgctat tgtctcatgg atctggaagc | 60 |
| gtcatttgtg ctgtcctcca tgggaacgat acagatatgc tgtcgcttct tgatttcaag | 120 |
| cgcgcaatca ccgacgatcc aaaagggctc ttgagctcat ggaacaccag tgttcacttc | 180 |
| tgcaactggc agggtgtgaa gtgcagcctc gaagaacatg agcgcgttgc agagctggac | 240 |
| ctgtcggagc agagttttgt cggggaaatc tctccttccc tcggaaacat gtcatatctt | 300 |
| acttatctta acctttccag aagcaagttc tctggtcaga taccacatct tggccggctg | 360 |
| caagaactgg agtttcttga cctgagtcac aactcgctac aagggattat tccagtgacg | 420 |
| ctcgcaaact gctccaactt gagggtgtta gacctctcaa gaaacttatt ggtgggtgaa | 480 |
| attccagcag aaatatccct actctccaat ctgacacgct gtggctttc ttataatgat | 540 |
| cttaccgggg tcattccacc aggccttggc aatatcactt ctctagaaca tattattctg | 600 |
| atgtataacc ggttagaggg aggcattcct gatgagtttg ggaagttgtc caaaatgtca | 660 |
| aacttactcc ttggtgaaaa caagctatca ggtagagtcc cagaggccat ttttaatatg | 720 |
| tctctgctaa atcaaatggc actggagttg aatatgctag ttggtactct accatctaac | 780 |
| atgggtgatg ctctcccctaa cctccgactt cttacgttgg gtgtaacat gctggaaggt | 840 |
| cttatcccag actcattagg caatgcatcc gagctacaac tgataaactt agcatataat | 900 |
| catgggttta gaggacgggt cccaccttct cttggtaaac tcccgaagct ccgtaagcta | 960 |
| ggtcttgaca caaacagtct tgaagcaaat gacagttggg gctgggaatt cttggatgca | 1020 |
| ttgagcaact gcacttctct agagatgctt tcactctatg caaatcggct acaaggaaac | 1080 |
| ttgccaaatt ctgttggcaa cctttcgtct aatgttaaca acctcgtgtt tggtaggaat | 1140 |
| atgctatatg gattagttcc atcaagcata ggaaatctcc atagactaac taagctagga | 1200 |
| ctggaggaga acaagttgac tggtccgatt gatggatgga ttggaaatct tgctaattta | 1260 |
| caaggtttat atcttcaaca gaacaatttc actggacaga ttccaacttc cattggcaat | 1320 |
| aactccaagc tgtcagaact gtttctggca ataatcaat tccacggtcc cataccatca | 1380 |
| agtttagaaa accttcagca actcttgtat ttagacctca gctataacaa tcttcaagaa | 1440 |
| aatatacccca agaggttttt tagtgtagcc acaattgccc aatgtgcgtt atcccacaac | 1500 |
| agcctagaag gccaaattcc tcacatcagt aatcttcaac aactcaacta tctagatctt | 1560 |
| tcatccaaca agcttactgg ggaaattcca cctactttgc gcacatgcca gcaattgcaa | 1620 |
| gccatcaaaa tggaccggaa ctttctctcg ggaagcattc ccatatttct aggcagtctg | 1680 |
| aacagcttga tcgagctcag cctttcacat aacaatctct caggctctat cccaattgct | 1740 |
| ctaagcaaac tgcaacttct cacccagttg gatctatccg acaatcatct tgaaggagaa | 1800 |
| gtaccagtag aaggaatatt caaaaataca acagccattt cccttaaagg caattggcgg | 1860 |
| cttttgtggag gtgtactgga cctacatatg ccttcatgcc ccgctgcttc tcagagaaga | 1920 |
| tctagatggc aacactattt ggtcagagta ttggtcccta tattaggcat cttgttactc | 1980 |

```
atattagtag tctgcttaac ccttctcaga agaggatgc tgaggatgca gttatcgctg    2040
ccttcttccg atgagcaatt ccctaaagta tcttataagg atctagcaca ggctactggg    2100
aacttcacag agtcaaactt gattgggaga ggaagctgcg gttcagtgta cagagcaaaa    2160
ctaaacccaa aacagatgct tgtggcagtg aaagttttg accttgacat gcaaggtgcg    2220
gataaaagtt tcatctcaga atgtaaagcg ctcagaaata ttcggcatcg aatcttctt    2280 ccaattctaa ctgcatgctc aacaattgat aatcgaggca gggatttcaa agctctagtc    2340
taccagttca tgcccaatgg caacttggac acttggctgc acccgacagg agatgaaaaa    2400
ggcccaaaac aattggacct ctctcaaaga atgaaaatag ctcttgatat agccgatgca    2460
ttgcaatata caccatga ctgtgagagc cctattgttc actgtgactt gaagcccagc      2520
aacatcctcc tagattatga tatgacagct cgtttggggg acttcggcat cgcaaggttc    2580
tacatcaaat ccaagtcagc agcagctggg ggtttgagtt caatgggtac aatgactctg    2640
aagggcacga ttggatatat cgctccagag tatgcaggag gcagctacct atccacctcc    2700
ggagacgtgt acagttttgg gatagtactg ctggagatgc tgacaggaag aaggccgacc    2760
gaccctatgt tctgcgaggg gcttgacatc gtgaactttg tcaggaggaa ctttccggat    2820
cagatacttc atatccttga cgcttctctc cgggaagaat gccaagactg ctcccaggat    2880
aatctggaag aagagaacga agtccaccgg tgcctgttgt ccttgctgaa agtggcactt    2940
tcttgcgcga gccaggatcc taacgagcga atcaacatga gagaagcagc tactgaactg    3000
cacgcgatcg acgcgtcgtt tgtgtcttga                                     3030
```

<210> SEQ ID NO 9  
<211> LENGTH: 3270  
<212> TYPE: DNA  
<213> ORGANISM: Artificial Sequence  
<220> FEATURE:  
<223> OTHER INFORMATION: TaLRRK-6D variant

<400> SEQUENCE: 9

```
atgcgttctc ccaagcaacc ggcgaagctc gtcatgcttt tactgttggc actgctgctg      60
ctctgtaacg gagttggcaa cgtccattgc acaaggatcc acgagaacag cgtcgatctg    120
cacgcgctgc tagacttcaa gcagggcatc aacaatcctc aggaagcctt gagcaattgg    180
agcaccacca cccacttctg tcgatggaat ggtgtcatct gcaccacgac acggccgttt    240
cgtgtcttgt cgcttatact cactgaattg gacttagcag ccaaatcag ctcctctctt     300 ggaaacttaa ccttccttga aacgcttgac ctttcatata ataacttcgt tggtcccttq    360 cctgtccttg gccatctcca caactccag acactttctc tgaacaacaa caggttaaat    420
gggatgattc ctgattcact taccaactgt tccagcttgg acactttaga tctctctgta    480
aacttcctag tgggtccaat tcctccgaat ttggacttgc tttcaaatct tacttactta    540
gatctctcta gtaacatgct agtgggtcaa attcctccga aactagtttc tctatcaaag    600
ctggtcacat tagatctctc ccataacatg ctagttggtc aattcctcc gaatctggac     660 ttgcttttcaa atctgactta cttagatcta tctagaaact tgctagtggg tcaaattcct    720
ctgaaaatag tttctctacc aaagctggcc acattagatc tctctactaa catgctagtg    780
ggtcaaattc ctccgaagtt aggctttgtt tcaagtctag aatacttcag tttggcatca    840
aacaaactcg agggaagcat tcctaatgag cttgggcaat tgcctagttt acaatacttg    900
ctcctgggag aaaataatct ttcaggtgaa ttcccgcatt ccatcttgaa cagaaacctt    960
```

```
tctgtttctc tcctatatct aggcttggag ctgaatatgc taggcaaggt attgccacct    1020
aatataggtg accttcgggg tctcgtacac cttacaatga gtggcaacat gtttgaaggg    1080
cacatcccag cttccctagg caacgccaca ggattaaaag taatagactt atcagctaac    1140
aatttcaccg ggcaaattcc taactctttt ggaaagctct caaatctgac taatctaaac    1200
cttcagtata accagcttga aacaagggac tgggaattct tcaatgcatt gacgaactgt    1260
cgttctctaa actcactctc actgggtttc aaccagctgc agggatctat accgcagtct    1320
gtcggtaacc tatccaacaa actagaaaaa cttactttga ctcaaaatag cttatcagga    1380
caagtacccc agagcatcgg caaccttagt gcattaaatc aactggcact aggtataaac    1440
aacttaagcg gcacaataga aggatggatt ggaaacctaa aaggccttga aggattaact    1500
ctccgctcaa accgcttcac cggccaaatc ccaccctcta ttagcaatct tactcggttg    1560
ataaatcttt atctctatga taatcaattc gagggcctca taccccccag cctgggaaac    1620
ctcccactca cacagctagt ccttagctct aacaatcttt acgggtacat accacccagc    1680
ttaggaagcc tccaacagct tacgtcattg aatcttagcc acaataatct ccaaggtgag    1740
atacctcaga ttagcgccct taagcaactc actactttag atctttcttc aaataagctc    1800
acagggagta ttccagattc tttgggccaa tgttacggct tacggagtct gcaaatggac    1860
caaaactttc tgtcaggaaa catcccaata gcctttggca aactgttgtc tctgagtata    1920
ctaaatctat cacacaacaa cttgtcaggc accatcccgt cggctctaaa caaactagag    1980
ttcctaaacc atcttgacct ttcatataat catcttgaag gaaaaatacc cagagatgga    2040
gcattcgaaa atgctacggc tgtttcactt gagaacaatt gggggctctg cggaggcgcc    2100
gtggatcttc acatggcttc atgcacaacc atttccaaga agaagagga gagacgatac     2160
cgtttgatta aagtattgat tccaatattt ggattcttgt cactggtact gttgatctac    2220
tttgtactcc ttgagaagaa gatgcgaagg gcaaatgata catcagcttc attaggcgag    2280
aattttctga aggtttctta tgcggatcta gcacaagcca catcaaactt ctctgaatct    2340
aacctggttg ggagaggagg ttatggctct gtctatcgcg gaaagttaaa ggattctaag    2400
gtggaagtgg ccgtcaaggt ttttgatctt gaaatgcatg gagctgagag aagctttctg    2460
aaagaatgcg aggcactgcg aagcattcag catagaaatc ttcttcccat cataactgct    2520
tgctcgacgg tagacaatac aggcaatgtt ttcaaagctt tagtttatga gttcatgcct    2580
aatgggaacc tagacacatg gctgcatcac agagaggacg ggaaggctca taaacattta    2640
agcttagctc aaagattaga catagctgtt aacatggctg acgcactgga ttatctacac    2700
catgactgcg gaagacccac catccattgt gacctgaagc ccagcaacat tcttctggat    2760
gatgatatga ccgctctttt aggagacttt ggtattgcaa gtttttacca agattccagg    2820
tcaacatcac ctggttcagt gagttcatca tcagtcggta tgaagggtac tattggatat    2880
attggtccag agtacgcggg aggtggccgc catgcatcaa cttgcggaga tgtttacggt    2940
tttgggataa tactgctgga aatgatgacc ggaaaaagac caacagatcc attgttcaag    3000
gatggagtta gcattgtcga ctttgtggag agcaactttc cacatgaaat agttcgtgtc    3060
attgatgcta atctcagtga agaatgcaag gacattgctc aatcaaagaa gatttcagaa    3120
aattcagttc atcaatgttt gctatctgtg ctgcaactag cactttcctg tacgcaccca    3180
gtaccaggcg aaagaatgaa tatgaaagtg gtggccagca aatgcatgc aattaaaaca     3240
tcctatgggg gctgcaatgc gcaagagtga                                     3270
```

<210> SEQ ID NO 10
<211> LENGTH: 1860
<212> TYPE: DNA
<213> ORGANISM: Artificial Sequence
<220> FEATURE:
<223> OTHER INFORMATION: TaLRRK-6D variant

<400> SEQUENCE: 10

```
atgatggatc tccacatgaa gtttctcctg gcctccctca gctgtgtact tctgatacaa      60
ggagctttct gtgggggggac tggagcgaca agctggactt gtgtgtgcac cgctcatcca     120
cttggcgaag caaactccaa tagcagcctg tcatccagtt gcgactcctc gtgccattgc     180
atacgagatg aaaacggcgg cacagggtca tggaactgct cgtgccgctc cgacaaggac     240
cttcaggaag aagaacacgc tgtggtgcac agtgggagtt gcttcacttc ctgtaactgc     300
acatctggaa gttctgaaca agagaggaag catttctcta gcaaaacagt cattgctaca     360
ctcctggtat gtgtggttct caccactgtt gctttcgtcg aacaacggc gtactacttc      420
cgccgcaagg acgcactctc ccgcgttcc cggatgcact ctttcgacaa gtacgcgagc      480
tggagcagca gatcgaacct cgttagccat cgatcttctc cccttaccca actgaaaccc     540
aaacccgggc tcagtgtcat caaagggttt ttgtgtagct gcccactcgt ctcccggagc     600
gaagacggcc cattccccgg cgtggttctc cggttctcct acgtcgagct ggagcaggca     660
acagggaaat tttccgacga cacctcatc ggcgtcggcg gaccagcaa ggtgtaccgt      720
ggacagctcg ccgacggcaa agtcgtcgcc gtgaagaagc ttcggcccct cggtggtgcg     780
gacgaagact atgagttcct gtcagagatc gagctgctgt cacggctgaa ccactgccat     840
gtggtgccat tgctggggta ctgctcggag cggcaggggc ggcagctgga gcggctgctg     900
gtgttcgagt gcatgaccaa cggcaacctg cgggagtgcc tggacgacct caacaggaag     960
cccatggact gggcgacgcg cgtcggcgtg gcgctgggcg ccgcgagggg cctcgagtac    1020
ctccacgagg cggcggcgcc gcgcatcctc caccgcgaca tcaagtccac caacatcctg    1080
ctcgacgacc ggttcagggc ccggatcacg gacctgggca tggccaagtg cctgatgaac    1140
gacggcgtga cgagctgctc tagctcgccg gcgcggatgc tgggcacctt cgggtacttc    1200
gccccgagt acgccatcgt cggcaaggcg tcgctcaagt cggacgtctt cagcttcggc     1260
gtggtggtgc tcgagctcat caccggccgg cagccggtgc acaagagagg cggcgccggc    1320
gccggtggcg gcggcacgga cgagagcctg tgatgtggg cgacgtcgcg gctccgggac    1380
agcaggttgg tggtggcgga gctgccggac ccggcgctga agggcgcgtt ccgcccgag     1440
gaaatgcaga tcatggcgca cctggccaga gagtgcctgc agtgggaccc cgaggccagg    1500
cccaccatga ccgaggtcgt tcagatcctc tccaccatcg cgcccttgc cgacaagcgc     1560
cgtcgccacc acctgcccgc cgccgccgcc gccttcgccc cgggcttccg tgccgagaag    1620
ccgcaggaat gctcagtgtg caggacggc gacgacggcc gtcgccgtga tcacctgcac     1680
ggggggaacg gtagcaatgc aaagggcacc gtccttgtcg gcgaggtcgc ggttaacgtc    1740
ggcacgccgg cggcgatggg ccggagctgg cggtcggcgg agcaggagga ggtggaccctg   1800
acggagccgc ggctggagac gttcacgcag ccgacaacga cggcgagcct cttcaggtga   1860
```

<210> SEQ ID NO 11
<211> LENGTH: 1031
<212> TYPE: PRT
<213> ORGANISM: Artificial Sequence
<220> FEATURE:
<223> OTHER INFORMATION: TaLRRK-6D variant

<400> SEQUENCE: 11

```
Met Ser Asp Gln Ser Val Lys Leu Asn Met Leu Leu Leu Ala Phe
1               5                   10                  15

Leu Leu Leu Ser Tyr Gly Ala Gly Asn Ala Arg Cys Ser Thr Val His
            20                  25                  30

Ala Asn Ile Thr Asp Ile Leu Ser Leu Leu Arg Phe Lys Arg Ser Thr
            35                  40                  45

His Asp Pro Thr Gly Ser Leu Arg Asn Trp Asn Arg Ser Ile His Tyr
        50                  55                  60

Cys Lys Trp Asn Gly Val Ser Cys Ser Leu Leu Asn Pro Gly Arg Val
65                  70                  75                  80

Ala Ala Leu Asp Leu Pro Gly Gln Asn Leu Ser Gly Gln Val Asn Pro
                85                  90                  95

Ser Leu Gly Asn Ile Thr Phe Leu Lys Arg Leu Asn Leu Ser Ser Asn
                100                 105                 110

Gly Phe Ser Gly Gln Leu Pro Pro Leu Ser Gln Leu His Glu Leu Thr
            115                 120                 125

Leu Leu Asp Met Ser Ser Asn Leu Phe Gln Gly Ile Ile Pro Asp Ser
130                 135                 140

Leu Thr Gln Phe Ser Asn Leu Gln Leu Leu Asn Leu Ser Tyr Asn Gly
145                 150                 155                 160

Phe Ser Gly Gln Leu Pro Pro Leu Asn Gln Leu Pro Glu Leu Val Val
                165                 170                 175

Leu Asp Leu Lys Ser Asn Leu Phe Gln Gly Ile Ile Pro Asp Ser Leu
            180                 185                 190

Thr Asn Cys Ser Asn Leu Thr Phe Val Asp Leu Ser Arg Asn Met Leu
        195                 200                 205

Glu Gly Ser Ile Pro Ala Lys Ile Gly Ser Leu Tyr Asn Leu Met Asn
210                 215                 220

Leu Asp Leu Ser Arg Asn Lys Leu Thr Gly Val Ile Pro Pro Thr Ile
225                 230                 235                 240

Ser Asn Ala Thr Lys Leu Gln Phe Leu Ile Leu Gln Glu Asn Glu Leu
            245                 250                 255

Glu Gly Ser Ile Pro Ser Glu Leu Gly Gln Leu Ser Asn Met Ile Gly
            260                 265                 270

Phe Thr Val Gly Ser Asn Arg Leu Ser Gly Gln Ile Pro Ala Ser Ile
        275                 280                 285

Phe Asn Leu Thr Leu Leu Arg Val Leu Gly Leu Tyr Ala Asn Arg Leu
    290                 295                 300

Gln Met Ala Ala Leu Pro Leu Asp Ile Gly His Thr Leu Pro Asn Leu
305                 310                 315                 320

Gln Asn Ile Thr Leu Gly Gln Asn Met Leu Glu Gly Pro Ile Pro Ala
            325                 330                 335

Ser Leu Gly Asn Ile Ser Ser Leu Gln Leu Ile Glu Leu Ser Asn Asn
            340                 345                 350

Ser Phe Thr Gly Glu Ile Pro Ser Phe Gly Lys Leu Gln Lys Leu Val
        355                 360                 365

Tyr Leu Asn Leu Ala Asp Asn Lys Leu Glu Ser Asp Ser Gln Arg
370                 375                 380

Trp Glu Ser Leu Tyr Gly Leu Thr Asn Cys Ser His Leu Lys Ser Leu
385                 390                 395                 400

Arg Phe Lys Asn Asn Gln Leu Lys Gly Val Ile Pro Asn Ser Val Gly
                405                 410                 415
```

```
Lys Leu Ser Pro Lys Leu Glu Leu Leu His Leu Gly Gly Asn Asn Leu
            420                 425                 430

Ser Gly Ile Val Pro Ser Ser Ile Gly Asn Leu Asp Gly Leu Ile Asp
            435                 440                 445

Leu Asp Leu Ser Thr Asn Ser Phe Asn Gly Thr Ile Glu Gly Trp Val
            450                 455                 460

Gly Ser Leu Lys Lys Leu Gln Ser Leu Asp Leu His Gly Asn Asn Phe
465                 470                 475                 480

Val Gly Ala Ile Pro Pro Ser Phe Gly Asn Leu Thr Glu Leu Thr Tyr
                    485                 490                 495

Leu Tyr Leu Ala Lys Asn Glu Phe Glu Gly Thr Ile Pro Pro Ile Leu
                500                 505                 510

Gly Lys Leu Lys Arg Leu Ser Ala Met Asp Leu Ser Tyr Asn Asn Leu
            515                 520                 525

Gln Gly Asp Ile Pro Pro Glu Leu Ser Gly Leu Thr Gln Leu Arg Thr
            530                 535                 540

Leu Asn Leu Ser Ser Asn Arg Leu Thr Gly Glu Ile Pro Val Asp Leu
545                 550                 555                 560

Ser Gln Cys Gln Asp Leu Val Thr Ile Gln Met Asp His Asn Asn Leu
                565                 570                 575

Thr Gly Asp Ile Pro Thr Thr Phe Gly Asp Leu Met Ser Leu Asn Met
                580                 585                 590

Leu Ser Leu Ser Tyr Asn Asp Leu Ser Gly Ala Ile Pro Val Ser Leu
            595                 600                 605

Gln His Val Ser Lys Leu Asp Leu Ser His Asn His Leu Gln Gly Glu
            610                 615                 620

Ile Pro Pro Glu Gly Val Phe Arg Asn Ala Ser Ala Val Ser Leu Ala
625                 630                 635                 640

Gly Asn Ser Glu Leu Cys Gly Gly Val Ser Glu Leu His Met Pro Pro
                645                 650                 655

Cys Pro Val Ala Ser Gln Arg Thr Lys Ile Arg Tyr Tyr Leu Ile Arg
                660                 665                 670

Val Leu Ile Pro Leu Phe Gly Phe Met Ser Leu Leu Leu Leu Val Tyr
            675                 680                 685

Phe Leu Val Leu Glu Arg Lys Met Arg Arg Thr Arg Tyr Glu Ser Gln
690                 695                 700

Ala Pro Leu Gly Glu His Phe Pro Lys Val Ser Tyr Asn Asp Leu Val
705                 710                 715                 720

Glu Ala Thr Lys Asn Phe Ser Glu Ser Asn Leu Leu Gly Lys Gly Ser
                725                 730                 735

Tyr Gly Thr Val Tyr Lys Gly Asn Leu Val Gln His Lys Leu Glu Val
            740                 745                 750

Ala Val Lys Val Phe Asn Leu Glu Met Gln Gly Ala Glu Arg Ser Phe
            755                 760                 765

Met Pro Glu Cys Glu Ala Leu Arg Ser Val Gln His Arg Asn Leu Val
            770                 775                 780

Ser Ile Ile Thr Ala Cys Ser Thr Val Asp Ser Asp Gly Arg Ala Phe
785                 790                 795                 800

Arg Ala Leu Ile Tyr Glu Phe Met Pro Lys Gly Asn Leu Asp Thr Cys
                805                 810                 815

Leu His His Lys Gly Asp Gly Lys Ala Asp Lys His Leu Thr Leu Thr
            820                 825                 830
```

```
Gln Arg Ile Gly Ile Ala Val Asn Ile Ala Asp Ala Leu Asp Tyr Leu
                835                 840                 845

His Asn Asp Ser Glu Asn Pro Ile Ile His Cys Asp Leu Lys Pro Ser
850                 855                 860

Asn Ile Leu Leu Asp Glu Asp Met Val Ala His Leu Gly Asp Phe Gly
865                 870                 875                 880

Ile Ala Arg Ile Phe Leu Asp Ser Gly Leu Arg Pro Ala Ser Ser Thr
                885                 890                 895

Ser Ser Ile Gly Val Lys Gly Thr Ile Gly Tyr Ile Pro Pro Glu Tyr
                900                 905                 910

Gly Gly Gly Gly Arg Ile Ser Thr Ser Gly Asp Val Tyr Ser Phe Gly
                915                 920                 925

Ile Val Leu Leu Glu Met Leu Thr Gly Lys Arg Pro Thr Asp Pro Met
930                 935                 940

Phe Met Asp Gly Leu Asp Ile Val Asn Phe Val Gly Asn Lys Phe Pro
945                 950                 955                 960

His Gln Ile His Glu Val Ile Asp Ile Tyr Leu Lys Gly Glu Cys Glu
                965                 970                 975

Ser Glu Asp Ser Val His Gln Cys Leu Val Ser Leu Leu Gln Val Ala
                980                 985                 990

Val Ser Cys Thr His Ser Ile Pro  Gly Glu Arg Ala Asn  Ile Arg Asp
                995                1000                1005

Thr Ala  Ser Lys Leu Gln Glu  Ile Lys Ala Ser Tyr  Leu Gly Arg
         1010                1015                1020

Lys Ala  Lys Ile Asn Pro Ser  Val
         1025                1030

<210> SEQ ID NO 12
<211> LENGTH: 1021
<212> TYPE: PRT
<213> ORGANISM: Artificial Sequence
<220> FEATURE:
<223> OTHER INFORMATION: TaLRRK-6D variant

<400> SEQUENCE: 12

Met Ser Asp Gln Ser Val Lys Leu Asn Met Leu Leu Leu Leu Ala Phe
1               5                   10                  15

Leu Leu Leu Ser Tyr Gly Ala Gly Asn Ala Arg Cys Ser Thr Val His
                20                  25                  30

Ala Asn Ile Thr Asp Ile Leu Ser Leu Leu Arg Phe Lys Arg Ser Thr
                35                  40                  45

His Asp Pro Thr Gly Ser Leu Arg Asn Trp Asn Arg Ser Ile His Tyr
        50                  55                  60

Cys Lys Trp Asn Gly Val Ser Cys Ser Leu Leu Asn Pro Gly Arg Val
65                  70                  75                  80

Ala Ala Leu Asp Leu Pro Gly Gln Asn Leu Ser Gly Gln Val Asn Pro
                85                  90                  95

Ser Leu Gly Asn Ile Thr Phe Leu Lys Arg Leu Asn Leu Ser Ser Asn
                100                 105                 110

Gly Phe Ser Gly Gln Leu Pro Asp Ala Ser Gln His Glu Leu Leu Leu
                115                 120                 125

Ile Pro Arg Asp Asn Pro Arg Phe Thr His Thr Ile Phe Glu Pro Thr
        130                 135                 140

Ala Pro Glu Phe Val Leu Gln Trp Leu Leu Arg Pro Val Thr Ser Ser
145                 150                 155                 160
```

-continued

Glu Pro Ala Ser Arg Ala Gly Gly Ser Gln Leu Glu Ile Gln Phe Ile
                165                 170                 175

Pro Arg Asp Asn Pro Arg Leu Thr His Lys Leu Phe Glu Pro His Val
            180                 185                 190

Cys Gly Ser Phe Lys Lys His Ala Arg Arg Leu Asn Pro Gly Glu Asn
        195                 200                 205

Arg Phe Ala Leu Gln Ser Asn Glu Phe Arg Pro Phe Asn Glu Met Thr
    210                 215                 220

His Arg Gly His Thr Thr Asn His Gln Pro Met Pro Pro Ser Tyr Asn
225                 230                 235                 240

Phe Ser Phe Phe Lys Lys Met His Leu Glu Gly Lys His Thr Gln Leu
                245                 250                 255

Ala Trp Thr Ile Val Gln His Asp Ser Ala Leu Leu Val Gly Ser Asn
            260                 265                 270

Lys Ala Leu Arg Ser Asn Ala Gln His Ala Ile Phe Lys Ser Tyr Phe
        275                 280                 285

Gly Ser Lys Cys Leu Gly Trp Tyr Ala Asn Lys Thr Thr Lys Trp Arg
    290                 295                 300

Ala Leu Pro Ile Arg Ile Gly Pro Asn Pro Leu Ile Ser Lys Lys
305                 310                 315                 320

Leu Thr Leu Gly Pro Lys Lys Ala Met Lys Val Leu Ser Gln Arg Arg
                325                 330                 335

Ser Val Thr Phe Gln Ala Cys Asn Leu Gln Ser Tyr Pro Ile Thr Val
            340                 345                 350

Ser Leu Glu Lys Phe Leu Val Ser Glu Ser Tyr Arg Asn Leu Tyr Thr
        355                 360                 365

Tyr Thr Leu Arg Thr Ile Ser Trp Ser Gln Val Thr Ala Lys Asp Gly
    370                 375                 380

Asn Leu Tyr Met Asp Gln Gln Thr Ala Val Ile His Asn Arg Ser Asp
385                 390                 395                 400

Ser Arg Ile Ile Ser Gln Lys Glu Ser Tyr Gln Ile Arg Ser Val Asn
                405                 410                 415

Cys Pro Leu Asn Leu Asn Phe Tyr Ile Trp Gly Gly Asn Asn Leu Ser
            420                 425                 430

Gly Ile Val Pro Ser Ser Gly Asn Leu Asp Gly Leu Ile Asp Leu
        435                 440                 445

Asp Leu Ser Thr Asn Ser Phe Asn Gly Thr Ile Glu Gly Trp Val Gly
    450                 455                 460

Ser Leu Lys Lys Leu Gln Ser Leu Asp Leu His Gly Asn Asn Phe Val
465                 470                 475                 480

Gly Ala Ile Pro Pro Ser Phe Gly Asn Leu Thr Glu Leu Thr Tyr Leu
                485                 490                 495

Tyr Leu Ala Lys Asn Glu Phe Glu Gly Thr Ile Pro Pro Ile Leu Gly
            500                 505                 510

Lys Leu Lys Arg Leu Ser Ala Met Asp Leu Ser Tyr Asn Asn Leu Gln
        515                 520                 525

Gly Asp Ile Pro Pro Glu Leu Ser Gly Leu Thr Gln Leu Arg Thr Leu
    530                 535                 540

Asn Leu Ser Ser Asn Arg Leu Thr Gly Glu Ile Pro Val Asp Leu Ser
545                 550                 555                 560

Gln Cys Gln Asp Leu Val Thr Ile Gln Met Asp His Asn Asn Leu Thr
                565                 570                 575

Gly Asp Ile Pro Thr Thr Phe Gly Asp Leu Met Ser Leu Asn Met Leu

```
                580             585             590
Ser Leu Ser Tyr Asn Asp Leu Ser Gly Ala Ile Pro Val Ser Leu Gln
            595                 600             605

His Val Ser Lys Leu Asp Leu Ser His Asn His Leu Gln Gly Glu Ile
610                 615                 620

Pro Pro Glu Gly Val Phe Arg Asn Ala Ser Ala Val Ser Leu Ala Gly
625                 630                 635                 640

Asn Ser Glu Leu Cys Gly Gly Val Ser Glu Leu His Met Pro Pro Cys
            645                 650                 655

Pro Val Ala Ser Gln Arg Thr Lys Ile Arg Tyr Tyr Leu Ile Arg Val
                660                 665                 670

Leu Ile Pro Leu Phe Gly Phe Met Ser Leu Leu Leu Val Tyr Phe
            675                 680                 685

Leu Val Leu Glu Arg Lys Met Arg Arg Thr Arg Tyr Glu Ser Gln Ala
            690                 695                 700

Pro Leu Gly Glu His Phe Pro Lys Val Ser Tyr Asn Asp Leu Val Glu
705                 710                 715                 720

Ala Thr Lys Asn Phe Ser Glu Ser Asn Leu Leu Gly Lys Gly Ser Tyr
                725                 730                 735

Gly Thr Val Tyr Lys Gly Asn Leu Val Gln His Lys Leu Glu Val Ala
                740                 745                 750

Val Lys Val Phe Asn Leu Glu Met Gln Gly Ala Glu Arg Ser Phe Met
            755                 760                 765

Pro Glu Cys Glu Ala Leu Arg Ser Val Gln His Arg Asn Leu Val Ser
770                 775                 780

Ile Ile Thr Ala Cys Ser Thr Val Asp Ser Asp Gly Arg Ala Phe Arg
785                 790                 795                 800

Ala Leu Ile Tyr Glu Phe Met Pro Lys Gly Asn Leu Asp Thr Cys Leu
                805                 810                 815

His His Lys Gly Asp Gly Lys Ala Asp Lys His Leu Thr Leu Thr Gln
                820                 825                 830

Arg Ile Gly Ile Ala Val Asn Ile Ala Asp Ala Leu Asp Tyr Leu His
            835                 840                 845

Asn Asp Ser Glu Asn Pro Ile Ile His Cys Asp Leu Lys Pro Ser Asn
850                 855                 860

Ile Leu Leu Asp Glu Asp Met Val Ala His Leu Gly Asp Phe Gly Ile
865                 870                 875                 880

Ala Arg Ile Phe Leu Asp Ser Gly Leu Arg Pro Ala Ser Ser Thr Ser
                885                 890                 895

Ser Ile Gly Val Lys Gly Thr Ile Gly Tyr Ile Pro Pro Glu Tyr Gly
            900                 905                 910

Gly Gly Gly Arg Ile Ser Thr Ser Gly Asp Val Tyr Ser Phe Gly Ile
            915                 920                 925

Val Leu Leu Glu Met Leu Thr Gly Lys Arg Pro Thr Asp Pro Met Phe
930                 935                 940

Met Asp Gly Leu Asp Ile Val Asn Phe Val Gly Asn Lys Phe Pro His
945                 950                 955                 960

Gln Ile His Glu Val Ile Asp Ile Tyr Leu Lys Gly Glu Cys Glu Ser
                965                 970                 975

Glu Asp Ser Val His Gln Cys Leu Val Ser Leu Leu Gln Val Ala Val
                980                 985                 990

Ser Cys Thr His Ser Ile Pro Gly  Glu Arg Ala Asn Ile  Arg Asp Thr
            995                 1000                1005
```

Ala Ser Lys Leu Gln Lys Lys Val Val Asn Cys Pro Leu
    1010                1015                1020

<210> SEQ ID NO 13
<211> LENGTH: 1031
<212> TYPE: PRT
<213> ORGANISM: Artificial Sequence
<220> FEATURE:
<223> OTHER INFORMATION: TaLRRK-6D variant

<400> SEQUENCE: 13

Met Ser Asp Gln Ser Val Lys Leu Asn Met Leu Leu Leu Ala Phe
1               5                   10                  15

Leu Leu Leu Ser Tyr Gly Ala Gly Asn Ala Arg Cys Ser Thr Val His
                20                  25                  30

Ala Asn Ile Thr Asp Ile Leu Ser Leu Leu Arg Phe Lys Arg Ser Thr
                35                  40                  45

His Asp Pro Thr Gly Ser Leu Arg Asn Trp Asn Arg Ser Ile His Tyr
            50                  55                  60

Cys Lys Trp Asn Gly Val Ser Cys Ser Leu Leu Asn Pro Gly Arg Val
65                  70                  75                  80

Ala Ala Leu Asp Leu Pro Gly Gln Asn Leu Ser Gly Gln Val Asn Pro
                85                  90                  95

Ser Leu Gly Asn Ile Thr Phe Leu Lys Arg Leu Asn Leu Ser Ser Asn
                100                 105                 110

Gly Phe Ser Gly Gln Leu Pro Pro Leu Ser Gln Leu His Glu Leu Thr
            115                 120                 125

Leu Leu Asp Met Ser Ser Asn Leu Phe Gln Gly Ile Ile Pro Asp Ser
130                 135                 140

Leu Thr Gln Phe Ser Asn Leu Gln Leu Leu Asn Leu Ser Tyr Asn Gly
145                 150                 155                 160

Phe Ser Gly Gln Leu Pro Pro Leu Asn Gln Leu Pro Glu Leu Val Val
                165                 170                 175

Leu Asp Leu Lys Ser Asn Leu Phe Gln Gly Ile Ile Pro Asp Ser Leu
            180                 185                 190

Thr Asn Cys Ser Asn Leu Thr Phe Val Asp Leu Ser Arg Asn Met Leu
            195                 200                 205

Glu Gly Ser Ile Pro Ala Lys Ile Gly Ser Leu Tyr Asn Leu Met Asn
        210                 215                 220

Leu Asp Leu Ser Arg Asn Lys Leu Thr Gly Val Ile Pro Pro Thr Ile
225                 230                 235                 240

Ser Asn Ala Thr Lys Leu Gln Phe Leu Ile Leu Gln Glu Asn Glu Leu
                245                 250                 255

Glu Gly Ser Ile Pro Ser Glu Leu Gly Gln Leu Ser Asn Met Ile Gly
            260                 265                 270

Phe Thr Val Gly Ser Asn Arg Leu Ser Gly Gln Ile Pro Ala Ser Ile
            275                 280                 285

Phe Asn Leu Thr Leu Leu Arg Val Leu Gly Leu Tyr Ala Asn Arg Leu
        290                 295                 300

Gln Met Ala Ala Leu Pro Leu Asp Ile Gly His Thr Leu Pro Asn Leu
305                 310                 315                 320

Gln Asn Ile Thr Leu Gly Gln Asn Met Leu Glu Gly Pro Ile Pro Ala
                325                 330                 335

Ser Leu Gly Asn Ile Ser Ser Leu Gln Leu Ile Glu Leu Ser Asn Asn
            340                 345                 350

-continued

```
Ser Phe Thr Gly Glu Ile Pro Ser Phe Gly Lys Leu Gln Lys Leu Val
        355                 360                 365

Tyr Leu Asn Leu Ala Asp Asn Lys Leu Glu Ser Ser Asp Ser Gln Arg
    370                 375                 380

Trp Glu Ser Leu Tyr Gly Leu Thr Asn Cys Ser His Leu Lys Ser Leu
385                 390                 395                 400

Arg Phe Lys Asn Asn Gln Leu Lys Gly Val Ile Pro Asn Ser Val Gly
                405                 410                 415

Lys Leu Ser Pro Lys Leu Glu Leu Leu His Leu Gly Gly Asn Asn Leu
            420                 425                 430

Ser Gly Ile Val Pro Ser Ile Gly Asn Leu Asp Gly Leu Ile Asp
        435                 440                 445

Leu Asp Leu Ser Thr Asn Ser Phe Asn Gly Thr Ile Glu Gly Trp Val
    450                 455                 460

Gly Ser Leu Lys Lys Leu Gln Ser Leu Asp Leu His Gly Asn Asn Phe
465                 470                 475                 480

Val Gly Ala Ile Pro Pro Ser Phe Gly Asn Leu Thr Glu Leu Thr Tyr
                485                 490                 495

Leu Tyr Leu Ala Lys Asn Glu Phe Glu Gly Thr Ile Pro Pro Ile Leu
            500                 505                 510

Gly Lys Leu Lys Arg Leu Ser Ala Met Asp Leu Ser Tyr Asn Asn Leu
        515                 520                 525

Gln Gly Asp Ile Pro Pro Glu Leu Ser Gly Leu Thr Gln Leu Arg Thr
    530                 535                 540

Leu Asn Leu Ser Ser Asn Arg Leu Thr Gly Glu Ile Pro Val Asp Leu
545                 550                 555                 560

Ser Gln Cys Gln Asp Leu Val Thr Ile Gln Met Asp His Asn Asn Leu
                565                 570                 575

Thr Gly Asp Ile Pro Thr Thr Phe Gly Asp Leu Met Ser Leu Asn Met
            580                 585                 590

Leu Ser Leu Ser Tyr Asn Asp Leu Ser Gly Ala Ile Pro Val Ser Leu
        595                 600                 605

Gln His Val Ser Lys Leu Asp Leu Ser His Asn His Leu Gln Gly Glu
    610                 615                 620

Ile Pro Pro Glu Gly Val Phe Arg Asn Ala Ser Ala Val Ser Leu Ala
625                 630                 635                 640

Gly Asn Ser Glu Leu Cys Gly Gly Val Ser Glu Leu His Met Pro Pro
                645                 650                 655

Cys Pro Val Ala Ser Gln Arg Thr Lys Ile Arg Tyr Tyr Leu Ile Arg
            660                 665                 670

Val Leu Ile Pro Leu Phe Gly Phe Met Ser Leu Leu Leu Leu Val Tyr
        675                 680                 685

Phe Leu Val Leu Glu Arg Lys Met Arg Arg Thr Arg Tyr Glu Ser Gln
    690                 695                 700

Ala Pro Leu Gly Glu His Phe Pro Lys Val Ser Tyr Asn Asp Leu Val
705                 710                 715                 720

Glu Ala Thr Lys Asn Phe Ser Glu Ser Asn Leu Leu Gly Lys Gly Ser
                725                 730                 735

Tyr Gly Thr Val Tyr Lys Gly Asn Leu Val Gln His Lys Leu Glu Val
            740                 745                 750

Ala Val Lys Val Phe Asn Leu Glu Met Gln Gly Ala Glu Arg Ser Phe
        755                 760                 765
```

Met Pro Glu Cys Glu Ala Leu Arg Ser Val Gln His Arg Asn Leu Val
770                 775                 780

Ser Ile Ile Thr Ala Cys Ser Thr Val Asp Ser Asp Gly Arg Ala Phe
785                 790                 795                 800

Arg Ala Leu Ile Tyr Glu Phe Met Pro Lys Gly Asn Leu Asp Thr Cys
                805                 810                 815

Leu His His Lys Gly Asp Gly Lys Ala Asp Lys His Leu Thr Leu Thr
                820                 825                 830

Gln Arg Ile Gly Ile Ala Val Asn Ile Ala Asp Ala Leu Asp Tyr Leu
                835                 840                 845

His Asn Asp Ser Glu Asn Pro Ile Ile His Cys Asp Leu Lys Pro Ser
850                 855                 860

Asn Ile Leu Leu Asp Glu Asp Met Val Ala His Leu Gly Asp Phe Gly
865                 870                 875                 880

Ile Ala Arg Ile Phe Leu Asp Ser Gly Leu Arg Pro Ala Ser Ser Thr
                885                 890                 895

Ser Ser Ile Gly Val Lys Gly Thr Ile Gly Tyr Ile Pro Pro Glu Tyr
                900                 905                 910

Gly Gly Gly Gly Arg Ile Ser Thr Ser Gly Asp Val Tyr Ser Phe Gly
                915                 920                 925

Ile Val Leu Leu Glu Met Leu Thr Gly Lys Arg Pro Thr Asp Pro Met
930                 935                 940

Phe Met Asp Gly Leu Asp Ile Val Asn Phe Val Gly Asn Lys Phe Pro
945                 950                 955                 960

His Gln Ile His Glu Val Ile Asp Ile Tyr Leu Lys Gly Glu Cys Glu
                965                 970                 975

Ser Glu Asp Ser Val His Gln Cys Leu Val Ser Leu Leu Gln Val Ala
                980                 985                 990

Val Ser Cys Thr His Ser Ile Pro  Gly Glu Arg Ala Asn  Ile Arg Asp
        995                 1000                1005

Thr Ala  Ser Lys Leu Gln Glu  Ile Lys Ala Ser Tyr  Leu Gly Arg
    1010                1015                1020

Lys Ala  Lys Ile Asn Pro Ser  Val
    1025                1030

<210> SEQ ID NO 14
<211> LENGTH: 1300
<212> TYPE: DNA
<213> ORGANISM: Artificial Sequence
<220> FEATURE:
<223> OTHER INFORMATION: TaLRRK6D

<400> SEQUENCE: 14
tggtggttct tgacttgaaa tccaatttat tccaagggat aatccccgac tcactcacaa      60
actgttcgaa cctcacgttt gtggatcttt caagaaacat gctagaaggc tcaatcccgg     120
cgaaaatagg ttcgctttac aatctaatga atttagacct ttctaggaat aaactcaccg     180
gggtcatacc accaaccatc agcaatgcca ccaagctaca atttctcatt cttcaagaaa     240
atgaactaga gggaagcata cccagtgagc ttggacaatt gtccaacatg atcggcttta     300
ctgttggtag caataggctc tcaggtcaaa taccagcatc aatctttaat cttactttgc     360
tccgagtgct aggcttgtac gcaaatagac tacaaatggc ggcactgcca cttgacattg     420
gccacaccct ccctaatctc caaaatatta ctttgggcca aaacatgctt gaaggtccta     480
tcccagcgtc gctaggtaac atttcaagcc tgcaattaat agagttatct aataacagtt     540

```
tcactggaga aattcctagt ttcggaaagc tacagaaact tgtatacctα aaccttgcgg      600 acaataagct ggagtcaagt gacagccaaa gatgggaatc tttatatgga ctaacaaact     660
gcagtcatct aaaatcgctc agattcaaga ataatcagct gaaaggagtc ataccaaatt    720
cggtaggtaa attgtcccct aaacttgaac ttctacatct gggtggaaac aatctatcag    780
gaatagttcc ttcaagcata ggaaaccttg atggcttaat agatttggat cttagcacaa    840
acagtttcaa tggtacaatt gaaggatggg taggaagtct taaaaaacta caatctctag    900
atcttcatgg aaacaatttc gttggagcca ttccaccctc ttttggcaac cttactgagc    960
taacatatct gtatttagca aaaaatgaat ttgaagggac catacctccc attctcggga   1020
aacttaaaag actctcagcc atggacctta gctataataa tcttcaaggt gacattcctc   1080
cagaactcag tgggcttaca caactccgta cactgaatct ttcatctaac agacttacag   1140
gagaaattcc tgttgatctg agccagtgtc aagacctggt aaccatccaa atggaccata   1200
ataacttgac gggtgacatt ccaaccactt tggtgaccct tatgagcttg aacatgctca   1260
gcctttccta taatgattta tcaggggcca tccctgtaag                          1300

<210> SEQ ID NO 15
<211> LENGTH: 1217
<212> TYPE: DNA
<213> ORGANISM: Artificial Sequence
<220> FEATURE:
<223> OTHER INFORMATION: CM6DTaLRRK

<400> SEQUENCE: 15
ttgaaatcca atttatccca agggataatc cccgactcac tcacaaactg ttcgaacctc      60
acgtttgtgg atcttttcaag agacatgcta gaaggctcaa tcccggcgaa aataggttcg    120
ctttacaatc taatgaattt agacctttct aggaataaac tctccggggt cataccacca     180
accatcagca atgccaccaa gctacaattt ctcattcttc aagaaaatga actagaggga    240 agcatacccα gtgagcttgg acaattgtcc aacatgatcg gctttactgt tggtagcaat    300
aggctctcag gtcaaatacc agcatcaatc tttaatctta ctttgctccg agtgctaggc    360
ttgtacgcaa atagactaca aatggcggca ctgccacttg acattggcca cccctccct    420 aatctccaaa atattacttt gggccaaaac atgcttgaag gtcctatccc agcgtcgcta    480
ggtaacattt caagcctgca attaatagag ttatctaata acagtttcac tggagaaatt    540
cctagtttcg gaaagctaca gaaacttgta tacctaaacc ttgcggacaa taagctggag    600
tcaagtgaca gccaaagatg ggaatctttα tatggactaa caaactgcag tcatctaaaa    660
tcgctcagat tcaagaataa tcagctgaaa ggagtcatac caaattcggt aggtaaattg    720
tcccctaaac ttgaacttct acatctgggt ggaacaatc tatcagggat agttccttca    780
agcataggaa accttgatgg cttaatagat ttggatctta gcacaaacag tttcaatggt    840
acaattgaag gatgggtagg aagtcttaaa aaactacaat ctctagatct tcatggaaac    900
aatttcgttg gagccattcc accctctttt ggcaaccttα ctgagctaac atatctgtat    960
ttagcaaaaa atgaatttga agggaccata cctcccactc tcgggaaact taaaagactc   1020
tcagccatgg accttagcta taataatctt caagggagaca ttcctccaga actcagtggg   1080
cttacacaac tccgtacacc gaatctttca tctaacagac ttacaggaga aattcctgtt   1140
gatctgagcc agtgtcaaga cctggtaacc atccaaatgg accataataa cttgacgggt   1200
gacattccaa ccacttt                                                   1217
```

<210> SEQ ID NO 16
<211> LENGTH: 1152
<212> TYPE: DNA
<213> ORGANISM: Artificial Sequence
<220> FEATURE:
<223> OTHER INFORMATION: Remus6DTaRRK

<400> SEQUENCE: 16

```
gaatttagac ctttctagga ataaactcac cggggtcata ccaccaacca tcagcaatgc      60
caccaagcta caatttctca ttcttcaaga aaatgaacta gagggaagca tacccagtga     120
gcttggacaa ttgtccaaca tgatcggctt tactgttggt agcaataggc tctcaggtca     180
aatgccagca tcaatcttta atcttacttt gctccgagtg ctaggcttgt acgcaaatag     240
actacaaatg gcggcactgc cacttgacat tggccacacc ctccctaatc tccaaaatat     300
tactttgggc caaaacatgc ttgaaggtcc tatcccagcg tcgctaggta acatttcaag     360
cctgcaatta atagagttat ctaataacag tttcactgga gaaattccta gtttcggaaa     420
gctacagaaa cttgtatacc taaaccttgc ggacaataag ctggagtcaa gtgacagcca     480
aagatgggaa tctttatatg gactaacaaa ctgcagtcat ctaaaatcgc tcagattcaa     540
gaataatcag ctgaaaggag tcataccaaa ttcggtaggt aaattgtccc ctaaacttga     600
acttctacat ctgggtggaa acaatctatc aggaatagtt ccttcaagca taggaaacct     660
tgatggctta atagatttgg atcttagcac aaacagtttc aatggtacaa ttgaaggatg     720
ggtaggaagt cttaaaaaac tacaatctct agatcttcat ggaaacaatt cgttggagc     780
cattccaccc tcttttggca accttactga gctaacatat ctgtatttag caaaaaatga     840
atttgaaggg accataccct ccattctcgg gaaacttaaa agactctcag ccatggacct     900
tagctataat aatcttcaag gtgacattcc tccagaactc agtgggctta cacaactccg     960
tacactgaat ctttcatcta acagacttac aggagaaatt cctgttgatc tgagccagtg    1020
tcaagacctg gtaaccatcc aaatggacca taataacttg acgggtgaca ttccaaccac    1080
ttttggtgac cttatgagct tgaacatgct cagccttttcc tataatgatt tatcaggggc    1140
catccctgta ag                                                        1152
```

<210> SEQ ID NO 17
<211> LENGTH: 1285
<212> TYPE: DNA
<213> ORGANISM: Artificial Sequence
<220> FEATURE:
<223> OTHER INFORMATION: Consensus sequence

<400> SEQUENCE: 17

```
ttgaaatcca atttatccaa gggataatcc ccgactcact cacaaactgt tcgaacctca      60
cgtttgtgga tctttcaaga acatgctag aaggctcaat cccggcgaaa ataggttcgc     120
tttacaatct aatgaattta gacctttcta ggaataaact caccggggtc ataccaccaa     180
ccatcagcaa tgccaccaag ctacaatttc tcattcttca agaaaatgaa ctagagggaa     240
gcatacccag tgagcttgga caattgtcca acatgatcgg ctttactgtt ggtagcaata     300
ggctctcagg tcaaatacca gcatcaatct ttaatcttac tttgctccga gtgctaggct     360
tgtacgcaaa tagactacaa atggcggcac tgccacttga cattggccac accctcccta     420
atctccaaaa tattactttg ggccaaaaca tgcttgaagg tcctatccca gcgtcgctag     480
gtaacatttc aagcctgcaa ttaatagagt tatctaataa cagtttcact ggagaaattc     540
ctagtttcgg aaagctacag aaacttgtat acctaaacct tgcggacaat aagctggagt     600
```

```
caagtgacag ccaaagatgg gaatctttat atggactaac aaactgcagt catctaaaat      660
cgctcagatt caagaataat cagctgaaag gagtcatacc aaattcggta ggtaaattgt      720
cccctaaact tgaacttcta catctgggtg gaaacaatct atcaggaata gttccttcaa      780
gcataggaaa ccttgatggc ttaatagatt tggatcttag cacaaacagt ttcaatggta      840
caattgaagg atgggtagga agtcttaaaa aactacaatc tctagatctt catggaaaca      900
atttcgttgg agccattcca ccctcttttg gcaaccttac tgagctaaca tatctgtatt      960
tagcaaaaaa tgaatttgaa gggaccatac ctcccattct cgggaaactt aaaagactct     1020
cagccatgga ccttagctat aataatcttc aaggtgacat tcctccagaa ctcagtgggc     1080
ttacacaact ccgtacactg aatctttcat ctaacagact tacaggagaa attcctgttg     1140
atctgagcca gtgtcaagac ctggtaacca tccaaatgga ccataataac ttgacgggtg     1200
acattccaac cacttttggt gaccttatga gcttgaacat gctcagcctt tcctataatg     1260
atttatcagg ggccatccct gtaag                                           1285

<210> SEQ ID NO 18
<211> LENGTH: 245
<212> TYPE: DNA
<213> ORGANISM: Artificial Sequence
<220> FEATURE:
<223> OTHER INFORMATION: Traes_6DL_0EF6FC

<400> SEQUENCE: 18
ttcggtattg caaggatttt tcttgattct gggctaagac cagcaagctc gacgagttca       60
attggtgtaa aaggaacgat aggctatatc ccaccagagt acggcggggg aggccgtata      120
tctacttctg gggatgtcta cagttttggg atagtgctgc tggagatgtt gactggcaaa      180
aggccaacag atcctatgtt tatggatgga ctggacatcg tcaacttcgt gggcaacaag      240
tttcc                                                                  245

<210> SEQ ID NO 19
<211> LENGTH: 22
<212> TYPE: DNA
<213> ORGANISM: Artificial Sequence
<220> FEATURE:
<223> OTHER INFORMATION: LRR1

<400> SEQUENCE: 19
ctaccaggcg ctaatatctt cc                                               22

<210> SEQ ID NO 20
<211> LENGTH: 158
<212> TYPE: DNA
<213> ORGANISM: Artificial Sequence
<220> FEATURE:
<223> OTHER INFORMATION: Traes_6DL_0EF6FC

<400> SEQUENCE: 20
cataatgaca gcgaaaaccc catcatccat tgtgatctga agcccagcaa tattcttctt       60
gatgaggaca tggttgctca tttgggggat ttcggtattg caaggatttt tcttgattct      120
gggctaagac cagcaagctc gacgagttca attggtgt                              158

<210> SEQ ID NO 21
<211> LENGTH: 12
<212> TYPE: DNA
<213> ORGANISM: Artificial Sequence
<220> FEATURE:
<223> OTHER INFORMATION: LRR2
```

-continued

<400> SEQUENCE: 21

```
cccttctacc ag                                                         12
```